US007074793B2

(12) United States Patent
Hudkins et al.

(10) Patent No.: US 7,074,793 B2
(45) Date of Patent: Jul. 11, 2006

(54) CYCLIC SUBSTITUTED FUSED PYRROLOCARBAZOLES AND ISOINDOLONES

(75) Inventors: Robert L. Hudkins, Chester Springs, PA (US); Dandu R. Reddy, Downingtown, PA (US); Jasbir Singh, Gilbertsville, PA (US); Rabindranath Tripathy, Landenberg, PA (US); Ted Underiner, Malvern, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 10/755,505

(22) Filed: Jan. 12, 2004

(65) Prior Publication Data
US 2004/0186157 A1 Sep. 23, 2004

Related U.S. Application Data

(63) Continuation of application No. 09/500,849, filed on Feb. 10, 2000.

(60) Provisional application No. 60/119,834, filed on Feb. 12, 1999.

(51) Int. Cl.
A61K 31/501 (2006.01)
C07D 403/14 (2006.01)
(52) U.S. Cl. .................. 514/252.01; 544/224; 544/235; 544/238; 546/268.1; 548/146; 548/200; 548/417; 514/252.06; 514/410
(58) Field of Classification Search ................ 548/417, 548/200, 146; 514/410, 252.01, 252.06; 544/224, 235, 238
See application file for complete search history.

(56) References Cited

U.S. PATENT DOCUMENTS

| | | | |
|---|---|---|---|
| 4,735,939 A | 4/1988 | McCoy et al. ............... 514/211 |
| 4,816,450 A | 3/1989 | Bell et al. ....................... 514/25 |
| 4,877,776 A | 10/1989 | Murakata et al. ............. 514/43 |
| 4,923,986 A | 5/1990 | Murakata et al. ............ 540/545 |
| 5,063,330 A | 11/1991 | Leprince et al. ......... 315/111.21 |
| 5,461,146 A | 10/1995 | Lewis et al. .................. 540/545 |
| 5,475,110 A | 12/1995 | Hudkins et al. .............. 546/256 |
| 5,516,771 A | 5/1996 | Dionne et al. ............... 514/211 |
| 5,545,636 A | 8/1996 | Heath, Jr. et al. ............ 514/214 |
| 5,552,396 A | 9/1996 | Heath, Jr. et al. ............ 514/183 |
| 5,591,855 A | 1/1997 | Hudkins et al. .............. 546/256 |
| 5,594,009 A | 1/1997 | Hudkins et al. .............. 514/338 |
| 5,616,724 A | 4/1997 | Hudkins et al. .............. 548/417 |
| 5,621,100 A | 4/1997 | Lewis et al. .................. 540/545 |
| 5,621,101 A | 4/1997 | Lewis et al. .................. 540/545 |
| 5,654,427 A | 8/1997 | Dionne et al. ............... 540/545 |
| 5,672,618 A | 9/1997 | Heath, Jr. et al. ............ 514/414 |
| 5,705,511 A | 1/1998 | Hudkins et al. .............. 514/338 |
| 5,710,145 A | 1/1998 | Engel et al. .................. 514/183 |
| 5,808,060 A | 9/1998 | Hudkins et al. .............. 540/577 |
| 6,127,401 A * | 10/2000 | Singh et al. .................. 514/410 |
| 6,359,130 B1 * | 3/2002 | Singh et al. .................. 540/546 |
| 6,841,567 B1 * | 1/2005 | Hudkins et al. .............. 514/410 |

FOREIGN PATENT DOCUMENTS

| | | |
|---|---|---|
| EP | 238011 | 9/1987 |
| WO | WO 94/02488 | 2/1994 |
| WO | WO 96/11933 | 4/1996 |
| WO | WO 97/07081 | 2/1997 |
| WO | WO 97/21677 | 6/1997 |
| WO | WO 98/07433 | 2/1998 |
| WO | WO 99/47522 | 9/1999 |
| WO | WO 99/62523 | 12/1999 |
| WO | WO 00/13015 | 3/2000 |

OTHER PUBLICATIONS

Angeles, T.S., et al., "Enzyme-linked immunosorbent assay for trkA tyrosine kinase activity," *Anal. Biochem.*, 1996, 236(0130), 49-55.

Avruch, J., et al., "Raf meets ras: completing the framework of a signal transduction pathway," *TIBS*, 1994, 19, 279-283.

Bottenstein, J.E., et al., "Growth of a rat neuroblastoma cell line in serum-free supplemented medium," *PNAS USA*, 1979, 76(1), 514-517.

Corey, E.J., et al., "Synthesis of new lipoxygenase inhibitors 13-THIA- and 10-THIAARACHIDONIC acids," *Tett. Letters*, 1985, 26(33), 3919-3922.

Denhardt, D.T., "Signal-transducing protein phosphorylation cascades mediated by Ras/Rho proteins in the mammalian cell: the potential for multiplex signalling," *Biochem. J.*, 1996, 318, 729.

Fearon, E.R., "Genetic lesions in human cancer", *Molecular Oncology*, 1996, 143-178.

Flannery, et al., "Alkylation of disodioacetylacetone with halo ketals," *J. Org. Chem.*, 1972, 37(18), 2806-2810.

Fonnum, F., "A rapid radiochemical method for the determination of choline acetyltransferase," *J. Neurochem*, 1975, 24, 407-409.

Glicksman, et al., "K-252a and staurosporine promote choline acetyltransferase activity in rat spinal cord cultures," *J. Neurochem*, 1993, 61, 210-221.

Grant & Hackh's Chemical Dictionary, 5th Ed., 1969.

Greene, T.W., et al., "Protective groups in organic synthesis," *Wiley & Sons*, 2nd ed., 1991.

Grove, D.S., et al., "Differential activation and inhibition of lymphocyte proliferation by modulators of protein kinase c: diacylglycerols, "rationally designed" activators and inhibitors of protein kinase C," *Experimental Cell Research*, 1991, 193, 175-182.

(Continued)

Primary Examiner—Golam M. M. Shameem
(74) Attorney, Agent, or Firm—Woodcock Washburn LLP

(57) ABSTRACT

The present invention is directed to cyclic substituted fused pyrrolocarbazoles and isoindolones. The invention also is directed to methods for making and using the cyclic substituted fused pyrrolocarbazoles and isoindolones.

25 Claims, 21 Drawing Sheets

OTHER PUBLICATIONS

Hart, L., et al., "Cyclopropane chemistry. VI. Acylation of some substituted cyclopropanes [1,2]," *J. Org. Chem.*, 1959, 24, 1261-1267.

Hawkins, et al., "Reactions of 1 : 2-dichloro-3 : 4-epoxybutane and related compounds," *J. Chem. Soc.*, 1959, 248-256.

Hershburg, R.N., et al., "ORSYAT," *Org. Syn.*, 1955, vol. III, 626-631.

Kase, H., et al., "K-252a, a potent inhibitor of protein kinase C from microbial origin," *J. Antibiotics*, 1986, 39(8), 1059-1065.

Knochel, P., et al., "Preparation and reactivity of highly functionalized organometallics at the α position of oxygen or nitrogen," *J. Org. Chem.*, 1993, 58, 588-599.

Kuehene, M.E., et al., "Studies in biomimetic alkaloid syntheses. 6. Alternative pathways to secodines and their acyclic enamino acrylate analogues. Total syntheses of desethylibophyllidine, D-norvincadifformine, desethylvincadifformine, 20-methyldesethylvincadifformine, and 3-oxovincadifformine," *J. Org. Chem.*, 1981, 46, 2002-2009.

Lehningerm A.L., "The molecular basis of cell structure and function," Chapter 4, *Biochemistry*, Second Edition, Worth Publishers, Inc., 1975, 73-75.

Makara, G.M., et al., "An efficient synthesis of 5,7-dimethoxy-4-methylphthalide, a key intermediate in the synthesis of mycophenolic acid," *J. Org. Chem.*, 1995, 60, 5717-5718.

Martin-Zanca, D., et al., "Moecular and biochemical characterization of the human *trk* proto-oncogene," *Mol. Cell. Biol.*, 1989, 9, 24-33.

McManaman, J.L., et al., "Developmental discord among markers for cholinergic differentiation: *In Vitro* time courses for early expression and responses to skeletal muscle extract," *Developmental Biology*, 125, 311-320.

Monia, B.P., et al., "Antitumor activity of a phosphorothioate antisense oligodeoxynucleotide targeted against C-*raf* kinase," *Nature Medicine*, 1996, 2(6), 668-674.

Paquette, L.A., et al., "First synthesis of cytotoxic 8,9-secokaurene diterpenoids. An enantioselective route to (—)-O-methylshikoccin and (+)-O-methylepoxyshikoccin," *J. Am. Chemm. So.*, 1997, 119, 9662-9671.

Phelps, P.E., et al., "Generation patterns of four groups of cholinergic neurons in rat cervical spinal cord: a combined tritiated thymidine autoradiographic and choline acetyltransferase immunocytochemical study," *J. Comp. Neurol.*, 1988, 273, 459-472.

Pitt, A.M., et al., "High throughput screening protein kinase assays optimized for reaction, binding, and detection totally within a 96-well plate," *J. Biomol. Screening*, 1996, 1(1), 47-51.

Reich, H.J., et al., "Organoselenium chemistry. Conversion of ketones to enones by selenoxide syn elimination," *J. Am. Chem. Soc.*, 1975, 97(19), 5434-5447.

Remington's Pharmaceutical Sciences, *Mack Pub. Co.*, 1980.

Rotin, D., et al., "SH2 domains prevent tyrosine dephosphorylation of the EGF receptor: identification of Tyr992 as the high-affinity binding site for SH2 domains of phospholipase $C_\gamma$," *EMBO J.*, 1992, 11, 559-567.

Smith, R.G., et al., "Trophic effects of skeletal muscle extracts on ventral spinal cord neurons in vitro: separation of a protein with morphologic activity from proteins with cholinergic activity," *J. Cell Biology*, 1985, 101, 1608-1621.

Wood, J.L., et al., "Total synthesis of (+)- and (—)-K252a," *J. Am. Chem. Soc.*, 1995, 117, 10413-10414.

Xia, Z., et al., "Opposing effects of ERK and JNK-p38 MAP kinases on apoptosis," *Science*, 1995, 270, 1326-1331.

Zirkle, C.L., et al., The isomeric 3-Oxa- and 3-thiagranatanin-7-ols and their derivatives; reduction of bicyclic amino ketones related to tropinone[1,2], *J. Org. Chem.*, 1961, 26, 395-407.

Zha, Jiping, et al., "Serine phosphorylation of death agonist BAD in response to survival factor results in binding to 14-3-3 Not $BCL-X_L$," *Cell*, 1996, 87, 619-628.

Copy of the Danish Search Report (01/2338).

Hudkins, R.L., et al., "Fused pyrrolo[2,3-*c*]carbazol-6-ones: novel immunostumulants that enhance human interferon-γ activity," *J. Med. Chem.*, 1997, 40, 2994-2996.

* cited by examiner

PG = Protecting Group
or
Polymeric Support

Preparation of Cyclic Substituents via Intra-Molecular Dipolar Cycloaddition

Preparation of Cyclic Substituents via Intra-Molecular Dipolar Cycloaddition

FIG. 8
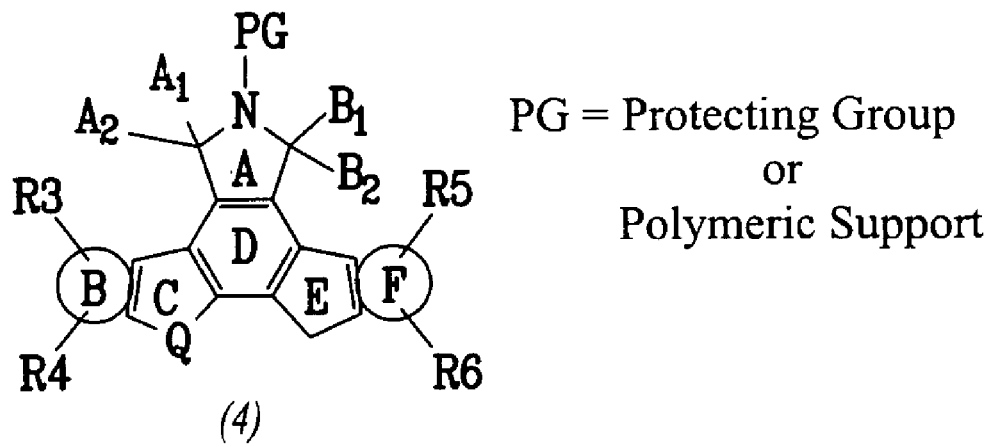
(4)
PG = Protecting Group
or
Polymeric Support
for Q =NH  1) Base
2) 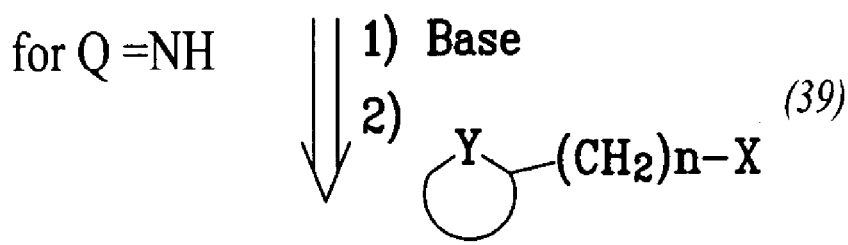 (39)
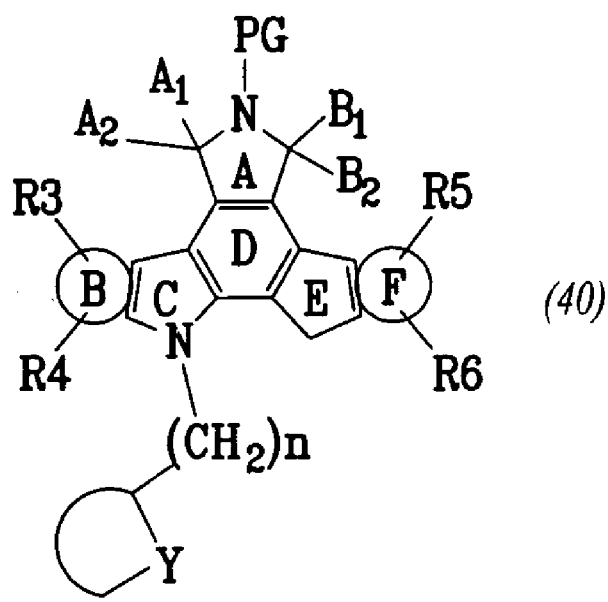
(40)

PG = Protecting Group
or
Polymeric Support

FIG. 11

Preparation of Soluble and Resin-bound N-lactam protected Fused Pyrrolocarbazoles (FP)

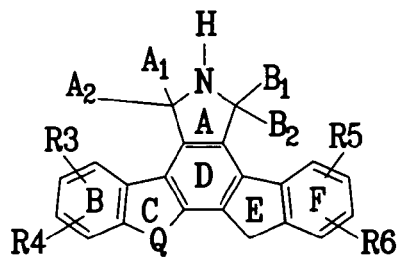

(47)

TsOH, Toluene, NMP, 140°C

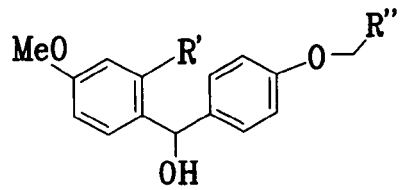

(51a) R'=H, R''= H (51b) R'=OMe, R''= Polymer (R'''')2R'''Si-X
Base
THF, DMF or NMP

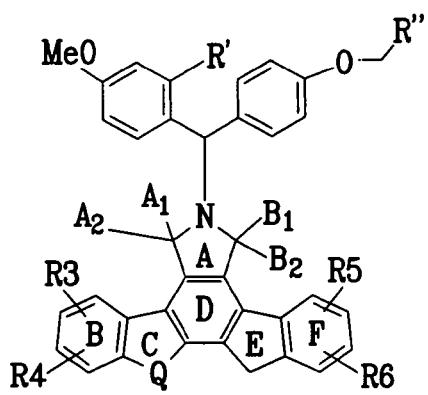

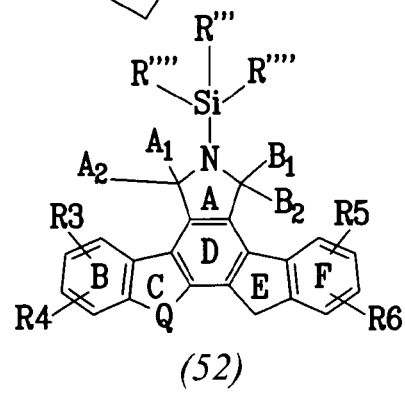

(52)

R'''' =Me, R''' = tBu (TBS)
R'''' =Ph, R''' = tBu (TBS)

(49) R' =H, R'' =H >> soluble protected FP
(N-protecting group abbreviated as DMB)

(50) R' =OMe, R'' = Polymer >> solid-bound PG
(the resin reagent reffered to as Rink-acid resin)
This is reffered to in the text as "Resin"

(e.g. Polymer = copolystyrene-1%divinylbenzene)

Preparation of Cyclic Substituents via Intra-molecular Dipolar Cycloaddition

Preparation of Cyclic Substituents via Intra-molecular Dipolar Cycloaddition

PG = Soluble or Polymer-bound Protecting Group (M = metal, e.g. Li, Mg etc.)

$R_{23}$ = F, $SR_{24}$, H etc.

FIG. 17
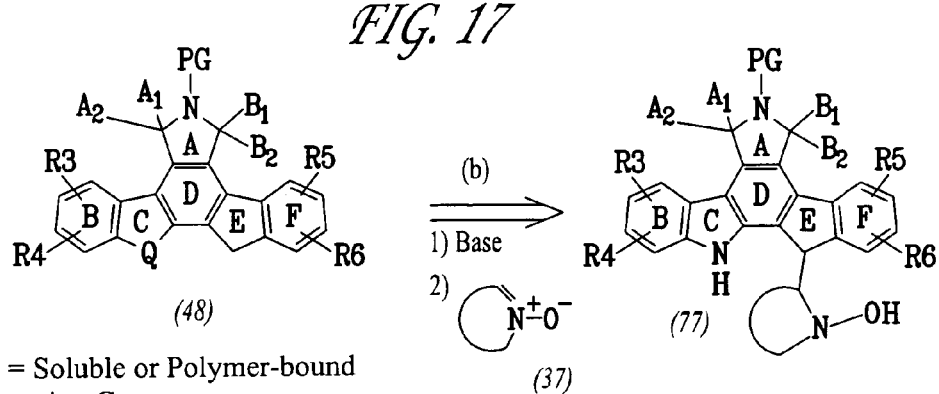
PG = Soluble or Polymer-bound
Protecting Group
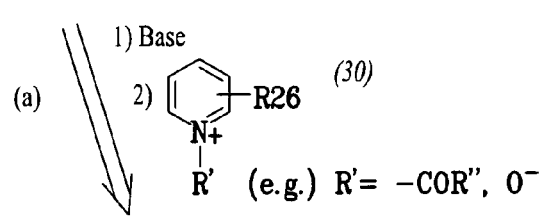
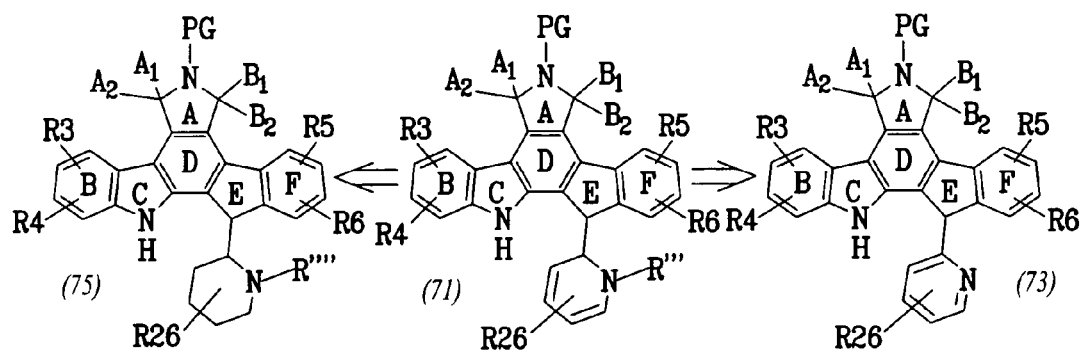
and/or R''''= H, COR''      and/or R'''= OH, COR''
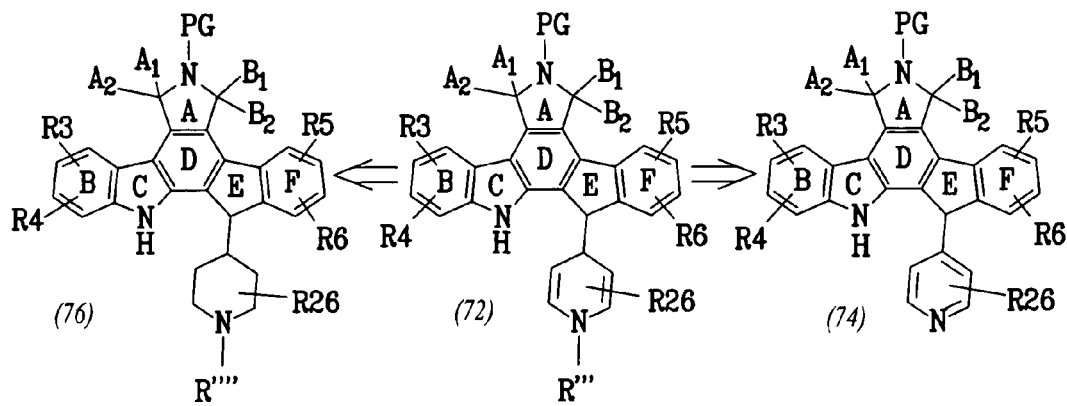

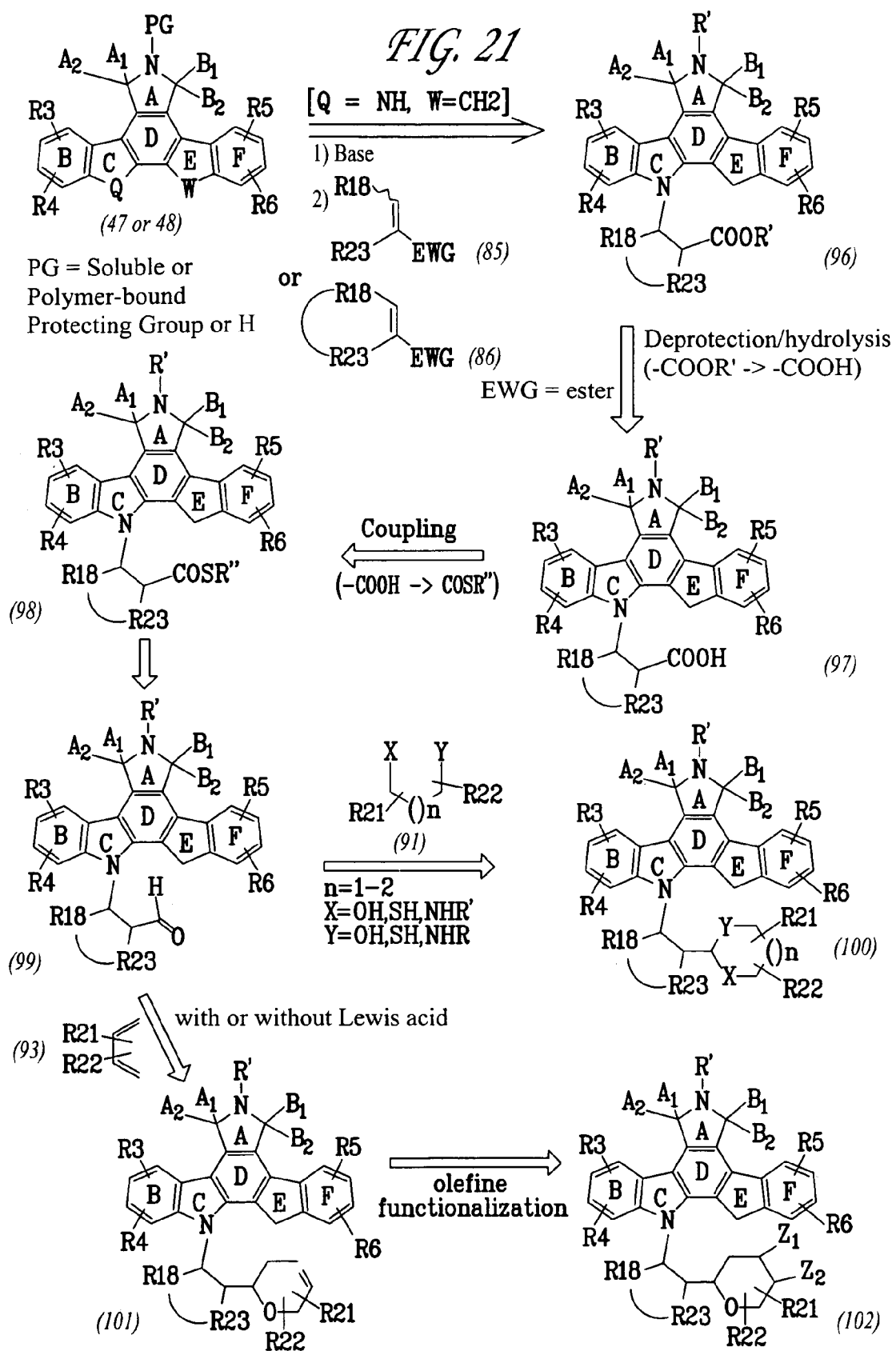

CYCLIC SUBSTITUTED FUSED PYRROLOCARBAZOLES AND ISOINDOLONES

CROSS REFERENCE TO RELATED APPLICATIONS

This application is a continuation of U.S. patent application Ser. No. 09/500,849, filed Feb. 10, 2000, which claims the benefit of U.S. Provisional Application Ser. No. 60/119, 834, filed Feb. 12, 1999, the content of each of which is incorporated herein by reference in its entirety.

FIELD OF INVENTION

The present invention is directed to cyclic substituted aryl and heteroaryl-fused pyrrolocarbazoles and isoindolones, which are referred to herein as "cyclic substituted fused pyrrolocarbazoles and isoindolones." The invention also is directed to methods for making and using cyclic substituted fused pyrrolocarbazoles and isoindolones.

BACKGROUND OF THE INVENTION

Protein kinases play a critical role in the control of cell growth and differentiation. Aberrant expression or mutations in protein kinases have been shown to lead to uncontrolled cell proliferation, such as malignant tumour growth, and various defects in developmental processes, including cell migration and invasion, and angiogenesis. Protein kinases are therefore critical to the control, regulation, and modulation of cell proliferation in diseases and disorders associated with abnormal cell proliferation. Protein kinases have also been implicated as targets in central nervous system disorders such as Alzheimer's disease, inflammatory disorders such as psoriasis, bone diseases such as osteoporosis, atheroscleroses, restenosis, thrombosis, metabolic disorders such as diabetes, and infectious diseases such as viral and fungal infections.

One of the most commonly studied pathways involving kinase regulation is cellular signaling from receptors at the cell surface to the nucleus. Generally, the function of each receptor is determined by its pattern of expression, ligand availability, and the array of downstream signal transduction pathways that are activated by a particular receptor. One example of this pathway includes a cascade of kinases in which members of the Growth Factor receptor Tyrosine Kinases deliver signals via phosphorylation to other kinases such as Src Tyrosine kinase, and the Raf, Mek and Erk serine/threonine kinase families. Each of these kinases is represented by several family members which play related, but functionally distinct roles. The loss of regulation of the growth factor signaling pathway is a frequent occurrence in cancer as well as other disease states. Fearon, *Genetic Lesions in Human Cancer, Molecular Oncology*, 1996, 143–178.

The raf1 serine/threonine kinase can be activated by the known oncogene product ras. The raf kinase enzyme positively regulates cell division through the Raf/MEK/ERK protein kinase cascade. This activation is the result of cRaf1 catalyzed phosphorylation of the protein kinase, MEK1, which phosphorylates and activates the protein kinase. ERK phosphorylates and regulates transcription factors required for cell division. Avruch et al., *TIBS*, 1994 (19) 279–283. cRaf1 negatively regulates cell death by modulation of the activity of Bcl-2, a critical regulator of apoptosis. This regulation involves direct phosphorylation of Bcl-2 family members. Gajewski and Thompson, *Cell*, 1996 (87) 619–628.

These aspects of cRaf1-mediated regulation of cell proliferation require the kinase activity of cRaf1. It has also been reported that the reduction of Raf protein levels correlates with a reduction in tumor growth rate in vivo tumor mouse models. Monia, Johnston, Geiger, Muller, and Fubro, *Nature Medicine, Vol. 2*, No. 6, June 1996, 668–674. Inhibitors of the kinase activity of cRaf1 should therefore provide effective treatment for a wide variety of human cancers.

Activation of the MAP kinase signaling pathways represents an attractive target for tumor therapy by inhibiting one or more of the kinases involved. An additional member of the MAP kinase family of proteins is the p38 kinase, alternatively known as the cytokine suppressive drug binding protein or reactivation kinase, RK. Activation of this kinase has been implicated in the production of proinflammatory cytokines such as IL-1 and TNF. Inhibition of this kinase could therefore offer a treatment for disease states in which disregulated cytokine production is involved.

The signals mediated by kinases have also been shown to control cell growth, cell death and differentiation in the cell by regulating the processes of the cell cycle. Progression through the eukaryotic cell cycle is controlled by a family of kinases called cyclin dependent kinases (CDKs). The loss of control of CDK regulation is a frequent event in hyperproliferative diseases and cancer.

Inhibitors of kinases involved in mediating or maintaining particular disease states represent novel therapies for these disorders. Examples of such kinases include inhibition of Src, raf, and the cyclin-dependent kinases (CDK) 1, 2, and 4 in cancer, CDK2 or PDGF-R kinase in restenosis, CDK5 and GSK3 kinases in Alzheimers, c-Src kinase in osteoporosis, GSK-3 kinase in type-2 diabetes, p38 kinase in inflammation, VEGF-R 1–3 and TIE-1 and -2 kinases in angiogenesis, UL97 kinase in viral infections, CSF-1R kinase in bone and hematopoetic diseases, and Lck kinase in autoimmune diseases and transplant rejection.

The microbial-derived material referred to as "K-252a" is a unique compound which has gained significant attention over the past several years due to the variety of functional activities which it possesses. K-252a is an indolocarbazole alkaloid that was originally isolated from a Nocardiosis sp. culture (Kase, H et al. 39 J. Antibiotics 1059, 1986). K-252a is an inhibitor of several enzymes, including protein kinase C (PKC) which plays a central role in regulating cell functions, and trk tyrosine kinase. The reported functional activities of K-252a and its derivatives are numerous and diverse: tumor inhibition (See U.S. Pat. Nos. 4,877,776, 4,923,986, and 5,063,330; European Publication 238,011 in the name of Nomato); antiI-insecticidal activity (See U.S. Pat. No. 4,735,939); inhibition of inflammation (See U.S. Pat. No. 4,816,450); treatment of diseases associated with neuronal cells (See U.S. Pat. Nos. 5,461,146; 5,621,100; 5,621,101; and WIPO Publication WO 94/02488, published Feb. 3, 1994 in the names of Cephalon, Inc. and Kyowa Hakko Kogyo Co., Ltd.); and treatment of prostate disease (See U.S. Pat. Nos. 5,516,771; and 5,654,427). K-252a also has been reported to inhibit IL-2 production (See Grove, D. S. et al., Experimental Cell Research 193: 175–182, 1991).

The reported indolocarbazoles share several common attributes. In particular, each comprises three five member rings which all include a nitrogen moiety; staurosporine (derived from Streptomyces sp.) and K-252a each further comprise a sugar moiety linked via two N-glycosidic bonds. Both K-252a and staurosporine have been extensively studied with respect to their utility as therapeutic agents. The indolocarbazoles are generally lypophilic, which allows for their comparative ease in crossing biological membranes, and, unlike proteinaceous materials, they manifest a longer in vivo half-life.

Although K-252a is normally derived from culture media via a fermentation process, the total synthesis of the natural (+) isomer and the unnatural (−) isomer, in which the three chiral carbons of the sugar have the opposite configurations, has been achieved (See Wood et al., J. Am. Chem. Soc. 117: 10413, 1995, and WIPO Publication WO 97/07081). However, this synthesis is not practical for commercial use.

In addition to the indolocarbazole alkaloids represented by K-252a and staurosporine, synthetic small organic molecules which are biologically active and known as fused pyrrolocarbazoles have been prepared (See U.S. Pat. Nos. 5,475,110; 5,591,855; 5,594,009; 5,705,511; and 5,616,724).

Fused isoindolones which are non-indole-containing molecules that can be chemically synthesized de novo are also known (See U.S. Pat. No. 5,808,060 and WIPO Publication WO 97/21677).

Certain bis-indolylmaleimide macrocyclic derivatives have also been reported (See for example U.S. Pat. Nos. 5,710,145; 5,672,618; 5,552,396 and 5,545,636).

Sugar derivatives of indolopyrrolocarbazoles also have been reported (see WIPO Publication WO98/07433).

Thus, there is a need for novel classes of compounds which demonstrate activity toward receptor and non-receptor types of protein kinases. It has been discovered that a class of compounds, referred to herein as cyclic substituted fused pyrrolocarbazoles and isoindolones, are useful as agents for the regulation of protein kinase. The present invention is therefore directed to, inter alia, their use as therapeutic agents for the treatment of the foregoing disorders, as well as other important ends.

SUMMARY OF THE INVENTION

The present invention is directed to cyclic substituted aryl and heteroaryl-fused pyrrolocarbazoles and isoindolones. Exemplary compounds of the invention have the general Formula I:

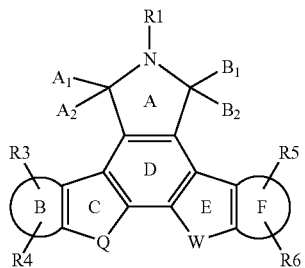

I wherein:
  ring B and ring F, independently, and each together with the carbon atoms to which they are attached, are selected from the group consisting of:
    a) an unsaturated 6-membered carbocyclic aromatic ring in which from 1 to 3 carbon atoms may be replaced by nitrogen atoms;
    b) an unsaturated 5-membered carbocyclic aromatic ring; and
    c) an unsaturated 5-membered carbocyclic aromatic ring in which either
      1) one carbon atom is replaced with an oxygen, nitrogen, or sulfur atom;
      2) two carbon atoms are replaced with a sulfur and a nitrogen atom, an oxygen and a nitrogen atom, or two nitrogen atoms; or
      3) three carbon atoms are replaced with three nitrogen atoms;
  $R^1$ is selected from the group consisting of:
    a) H, substituted or unsubstituted alkyl having from 1 to 4 carbons, substituted or unsubstituted aryl, substituted or unsubstituted arylalkyl, substituted or unsubstituted heteroaryl, or substituted or unsubstituted heteroarylalkyl;
    b) —C(=O)$R^9$, where $R^9$ is selected from the group consisting of alkyl, aryl and heteroaryl;
    c) —O$R^{10}$, where $R^{10}$ is selected from the group consisting of H and alkyl having from 1 to 4 carbons;
    d) —C(=O)NH$_2$, —N$R^{11}R^{12}$, —(CH$_2$)$_p$N$R^{11}R^{12}$, —(CH$_2$)$_p$O$R^{10}$, —O(CH$_2$)$_p$O$R^{10}$ and —O(CH$_2$)$_p$N$R^{11}R^{12}$, wherein p is from 1 to 4; and wherein either
      1) $R^{11}$ and $R^{12}$ are each independently selected from the group consisting of H and alkyl having from 1 to 4 carbons; or
      2) $R^{11}$ and $R^{12}$ together form a linking group of the formula —(CH$_2$)$_2$—$X^1$—(CH$_2$)$_2$—, wherein $X^1$ is selected from the group consisting of —O—, —S—, and —CH$_2$—;
  $R^2$ is selected from the group consisting of H, alkyl having from 1 to 4 carbons, —OH, alkoxy having from 1 to 4 carbons, —OC(=O)$R^9$, —OC(=O)N$R^{11}R^{12}$, —O(CH$_2$)$_p$N$R^{11}R^{12}$, —O(CH$_2$)$_p$O$R^{10}$, substituted or unsubstituted arylalkyl having from 6 to 10 carbons, and substituted or unsubstituted heteroarylalkyl;
  $R^3$, $R^4$, $R^5$ and $R^6$ are each independently selected from the group consisting of:
    a) H, aryl, heteroaryl, F, Cl, Br, I, —CN, CF$_3$, —NO$_2$, —OH, —O$R^9$, —O(CH$_2$)$_p$N$R^{11}R^{12}$, —OC(=O)$R^9$, —OC(=O)N$R^{11}R^{12}$, —O(CH$_2$)$_p$O$R^{10}$, —CH$_2$O$R^{10}$, —N$R^{11}R^{12}$, —N$R^{10}$S(=O)$_2R^9$, —N$R^{10}$C(=O)$R^9$,
    b) —CH$_2$O$R^{14}$, wherein $R^{14}$ is the residue of an amino acid after the hydroxyl group of the carboxyl group is removed;
    c) —N$R^{10}$C(=O)N$R^{11}R^{12}$, —CO$_2R^2$, —C(=O)$R^2$, —C(=O)N$R^{11}R^{12}$, —CH=NO$R^2$, —CH=N$R^9$, —(CH$_2$)$_p$N$R^{11}R^{12}$, —(CH$_2$)$_p$NH$R^{14}$, or —CH=NN$R^2R^{24}$ wherein $R^{24}$ is the same as $R^2$;
    d) —S(O)$_yR^2$, —(CH$_2$)$_p$S(O)$_yR^9$, —CH$_2$S(O)$_yR^{14}$ wherein y is 0, 1 or 2;
    e) alkyl having from 1 to 8 carbons, alkenyl having from 2 to 8 carbons, and alkynyl having 2 to 8 carbons, wherein
      1) each alkyl, alkenyl, or alkynyl group is unsubstituted; or
      2) each alkyl, alkenyl or alkynyl group is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, —CN, —NO$_2$, —OH, —O$R^9$, —X$^2$(CH$_2$)$_p$N$R^{11}R^{12}$, —X$^2$(CH$_2$)$_p$ C(=O)N$R^{11}R^{12}$, —X$^2$(CH$_2$)$_p$OC(=O) N$R^{11}R^{12}$, —X$^2$(CH$_2$)$_p$CO$_2R^9$, X$^2$(CH$_2$)$_p$S(O)$_yR^9$, —X$^2$(CH$_2$)$_p$N$R^{10}$C(=O)N$R^{11}R^{12}$, —OC(=O)

$R^9$, —OCONR$^2$, —O-tetrahydropyranyl, —NR$^{11}$R$^{12}$, —NR$^{10}$CO$_2$R$^9$, —NR$^{10}$C(=O) NR$^{11}$R$^{12}$, —NHC(=NH)NH$_2$, NR$^{10}$C(=O)R$^9$, —NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, CH=NNR$^2$R$^{2A}$, —CH=NOR$^2$, —CH=NR$^9$, —CH=NNHCH(N=NH)NH$_2$, —S(=O)$_2$ NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

$X^2$ is O, S, or NR$^{10}$;

$R^7$ is

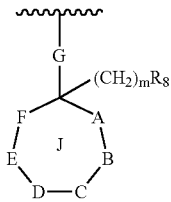

wherein:

m is 0–4;

G is a bond; or alkylene having 1 to 4 carbons, wherein the alkylene group is unsubstituted, or substituted with NR$^{11A}$R$^{12A}$ or OR$^{19}$;

R$^{11A}$ and R$^{12A}$ are the same as R$^{11}$ and R$^{12}$;

R$^{19}$ is selected from the group consisting of H, alkyl, acyl, and C(=O)NR$^{11A}$R$^{12A}$;

R$^8$ is selected from the group consisting of O(C=O) NR$^{11}$R$^{12}$, —CN, acyloxy, alkenyl, —O—CH$_2$— O—(CH$_2$)$_2$—O—CH$_3$, halogen and R$^{14}$ wherein R$^{14}$ is the same as R$^1$;

A and B are independently selected from the group consisting of O, N, S, CHR$^{17}$, C(OH)R$^{17}$, C(=O), and CH$_2$=C; or A and B together can form —CH=CH—;

C and D are independently selected from the group consisting of a bond, O, N, S, CHR$^{17}$, C(OH)R$^{17}$, C(=O) and CH$_2$=C;

E and F are independently selected from the group consisting of a bond, O, N, S, C(=O), and CH(R$^{17}$);

R$^{17}$ is selected from the group consisting of H, substituted or unsubstituted alkyl, alkoxycarbonyl, and substituted or unsubstituted alkoxy;

wherein:

1) ring J contains 0 to 3 ring heteroatoms;
2) any two adjacent hydroxyl groups of ring J can be joined in a dioxolane ring;
3) any two adjacent ring carbon atoms of ring J can be joined to form a fused aryl or heteroaryl ring;
4) any two adjacent ring nitrogen atoms of ring J can be joined to form a fused heterocyclic ring which can be substituted with 1 to 3 alkyl or aryl groups;

provided that:

1) ring J contain at least one carbon atom that is saturated;
2) ring J not contain two adjacent ring O atoms;
3) ring J contains a maximum of two ring C(=O) groups;
4) when G is a bond, ring J can be heteroaryl;

Q is selected from the group consisting of O, S, NR$^{13}$, NR$^{7A}$ wherein R$^{7A}$ is the same as R$^7$, CHR$^{15}$, X$^3$CH (R$^{15}$), and CH(R$^{15}$)X$^3$, wherein X$^3$ is selected from the group consisting of —O—, —S—, —CH$_2$—, NR$^{7A}$, and NR$^{13}$;

W is selected from the group consisting of CR$^{18}$R$^7$ and CHR$^2$;

R$^3$ is selected from the group consisting of H, —SO$_2$R$^9$, —CO$_2$R$^9$, —C(=O)R$^9$, —C(=O) NR$^{11}$R$^{12}$, alkyl of 1–8 carbons, alkenyl having 2–8 carbons, and alkynyl having 2–8 carbons; and either 1) the alkyl, alkenyl, or alkynyl group is unsubstituted; or
2) the alkyl, alkenyl, or alkynyl group independently is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$ NR$^{11}$R$^{12}$, —X$^2$(CH$_2$)$_p$C(=O)NR$^{11}$R$^{12}$, —X$^2$ (CH$_2$)$_p$OC(=O)NR$^{11}$R$^{12}$, —X$^2$(CH$_2$)$_p$CO$_2$R$^9$, X$^2$(CH$_2$)$_p$S(O)$_y$R$^9$, —X$^2$(CH$_2$)$_p$NR$^{10}$C(=O) NR$^{11}$R$^{12}$, —OC(=O)R$^9$, —OCONHR$^2$, —O-tetrahydropyranyl, —NR$^{11}$R$^{12}$, —NR$^{10}$CO$_2$R$^9$, —NR$^{10}$C(=O)NR$^{11}$R$^{12}$, —NHC(=NH)NH$_2$, NR$^{10}$C(=O)R$^9$, —NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{2A}$, —CH=NOR$^2$, —CH=NR$^9$, —CH=NNHCH(N=NH)NH$_2$, —S(=O)$_2$NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

R$^{15}$ is selected from the group consisting of H, OR$^{10}$, SR$^{10}$, R$^{7A}$, and R$^{16}$;

R$^{16}$ is selected from the group consisting of alkyl of 1 to 4 carbons; phenyl; naphthyl; arylalkyl having 7 to 15 carbons, —SO$_2$R$^9$, —CO$_2$R$^9$, —C(=O)R$^9$, alkyl having 1–8 carbons; alkenyl having 2 to 8 carbons, and alkynyl having 2 to 8 carbons, wherein 1) each alkyl, alkenyl, or alkynyl group is unsubstituted; or
2) each alkyl, alkenyl, or alkynyl group is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$NR$^{11}$R$^{12}$, —X$^2$(CH$_2$)$_p$C(=O) NR$^{11}$R$^{12}$, —X$^2$(CH$_2$)$_p$OC(=O)NR$^{11}$R$^{12}$, —X$^2$ (CH$_2$)$_p$CO$_2$R$^9$, X$^2$(CH$_2$)$_p$S(O)$_y$R$^9$, —X$^2$(CH$_2$)$_p$ NR$^{10}$C(=O)NR$^{11}$R$^{12}$, —OC(=O)R$^9$, —OCONHR$^2$, —O-tetrahydropyranyl, —NR$^{11}$R$^{12}$, —NR$^{10}$CO$_2$R$^9$, —NR$^{10}$C(=O)NR$^{11}$R$^{12}$, —NHC (=NH)NH$_2$, NR$^{10}$C(=O)R$^9$, —NR$^{10}$S(O)$_2$ R$^9$, —S(O)$_y$R$^9$, —CO$_2$R$^2$, —C(=O)NR$^{11}$ R$^{12}$, —C(=O)R$^2$, —CH$_2$OR$^{10}$, —CH=NNR$^2$ R$^{2A}$, —CH=NOR$^2$, —CH=NR$^9$, —CH=NN HCH(N=NH)NH$_2$, —S(=O)$_2$NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

R$^{18}$ is selected from the group consisting of R$^2$, thioalkyl of 1–4 carbons, and halogen;

A$^1$ and A$^2$ are selected from the group consisting of H, H; H, OR$^2$; H, —SR$^2$; H, —N(R$^2$)$_2$; and a group wherein A$^1$ and A$^2$ together form a moiety selected from the group consisting of =O, =S, and =NR$^2$;

B$^1$ and B$^2$ are selected from the group consisting of H, H; H, —OR$^2$; H, —SR$^2$; H, —N(R$^2$)$_2$; and a group wherein B$^1$ and B$^2$ together form a moiety selected from the group consisting of =O, =S, and =NR$^2$; with the proviso that at least one of the pairs A$^1$ and A$^2$, or B$^1$ and B$^2$, form =O;

with the proviso that when Q is NH or NR$^{7A}$, and in any R$^7$ or R$^{7A}$ group m is 0 and G is a bond, R$^8$ is H, and R$^7$ or R$^{7A}$ contains one ring hetero oxygen atom at position A in a 5- or 6-membered ring, then B cannot be CHR$^{17}$ where R$^{17}$ is substituted or unsubstituted alkyl; and with the further proviso that the compound of Formula I contains one R$^7$ or R$^{7A}$ group or both an R$^7$ and R$^{7A}$ group.

In some preferred embodiments of the compounds of Formula I, A and B are independently selected from the group consisting of O, N, S, CHR$^{17}$, C(OH)R$^{17}$, C(=O), and CH$_2$=C;

R$^{17}$ is selected from the group consisting of H, substituted or unsubstituted alkyl, and substituted or unsubstituted alkoxy; wherein:

1) ring J contains 0 to 3 ring heteroatoms;
2) any two adjacent hydroxyl groups of ring J can be joined in a dioxolane ring;
3) any two adjacent ring carbon atoms of ring J can be joined to form a fused aryl or heteroaryl ring;

provided that:
1) ring J contain at least one carbon atom that is saturated;
2) ring J not contain two adjacent ring O atoms;
3) ring J contains a maximum of two ring C(=O) groups;
4) when G is a bond, ring J can be heteroaryl; and R$^8$ is selected from the group consisting of O(C=O) NR$^{11}$R$^{12}$, acyloxy, alkenyl, —O—CH$_2$—O—(CH$_2$)$_2$—O—CH$_3$, halogen and R$^{14}$ wherein R$^{14}$ is the same as R$^1$.

In some preferred embodiments of the compounds of the invention, R$^1$, R$^4$ and R$^6$ are H. In further preferred embodiments of the compounds of the invention, one of A$_1$,A$_2$ or B$_1$,B$_2$ is H,H and the other is =O. Preferably, R$^1$, R$^4$ and R$^6$ are H and one of A$_1$,A$_2$ or B$_1$,B$_2$ is H,H and the other is =O.

In further preferred embodiments, R$^1$, R$^4$, R$^5$, R$^6$ and R$^8$ are H.

In some preferred embodiments, R3 and R5 are independently selected from the group consisting of H, alkoxy, halogen, alkoxyalkyl, alkoxy-alkoxyalkyl and alkoxy-alkoxycarbonyl.

In some preferred embodiments, Q is NR$^{13}$, preferably wherein R$^{13}$ is H or R$^{7A}$, with H being especially preferred.

In some preferred embodiments of the compounds of the invention, W is CH$_2$ or CR$^{18}$R$^7$ with CR$^{18}$R$^7$ being preferred. Preferably, R$^{18}$ is H or lower alkyl. In some preferred embodiments, R$^7$ is a 3-, 4-, 5- or 6-membered carbocyclic ring, or a 5- or 6-membered heterocyclic ring which contains one or two ring O, N, or S atoms. More preferably, R$^7$ is a heterocyclic ring having one ring O, N, or S hetero atom. In some especially preferred embodiments, R$^7$ is a 3-, 4-, 5- or 6-membered heterocyclic ring which contains one ring O atom.

In some preferred embodiments, G is a bond or CH$_2$. In further preferred embodiments, m is 0 or 1.

In some preferred embodiments, R$^8$ is H, OH, halogen, ethenyl, acyloxy, alkoxy, substituted or unsubstituted phenyl, substituted or unsubstituted heteroaryl, or hydroxyalkyl, with H or OH being preferred.

In some preferred embodiments, the compounds of the invention have the Formula II:

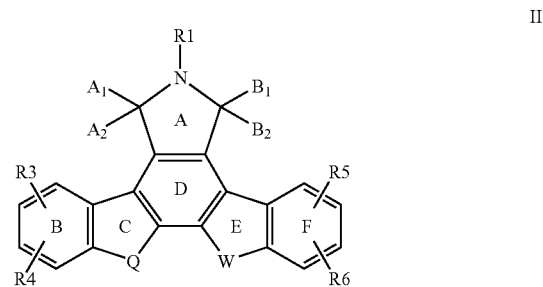

II

In some preferred embodiments of the compounds of Formula II, R$^1$, R$^4$ and R$^6$ are H. In further preferred embodiments of the compounds of Formula II, one of A$_1$,A$_2$ or B$_1$,B$_2$ is H,H and the other is =O. In further preferred embodiments of the compounds of Formula II, R3 and R5 are, independently selected from the group consisting of H, alkoxy, halogen, alkoxyalkyl, alkoxy-alkoxyalkyl and alkoxy-alkoxycarbonyl. In still further preferred embodiments of the compounds of Formula II, G is a bond or CH$_2$.

In further preferred embodiments of the compounds of Formula II, W is CH$_2$ or CR$^{18}$R$^7$. In still further preferred embodiments of the compounds of Formula II, Q is NR$^{13}$ or NR$^{7A}$. In further preferred embodiments of the compounds of Formula II, R$^8$ is H, OH, halogen, ethenyl, acyloxy, alkoxy, substituted or unsubstituted phenyl, substituted or unsubstituted heteroaryl, or hydroxyalkyl.

In more preferred embodiments of the compounds of Formula II, R$^1$, R$^4$ and R$^6$ are H; one of A$_1$,A$_2$ or B$_1$,B$_2$ is H,H and the other is =O; R3 and R5 are, independently selected from the group consisting of H, alkoxy, halogen, alkoxyalkyl, alkoxy-alkoxyalkyl and alkoxy-alkoxycarbonyl; G is a bond or CH$_2$; and W is CH$_2$ or CR$^{18}$R$^7$; R$^8$ is selected from the group consisting of H, OH, halogen, ethenyl, acyloxy, alkoxy, substituted or unsubstituted phenyl, substituted or unsubstituted heteroaryl, and hydroxyalkyl; and Q is NR$^{13}$ or NR$^{7A}$. Preferably, R$^8$ is H or OH.

In some even more preferred embodiments of the compounds of Formula II, Q is NR$^{13}$ where R$^{13}$ is H, G is a bond; and W is CR$^{18}$R$^7$ where R$^{18}$ is H or lower alkyl; and R$^3$ and R$^5$ are independently selected from the group consisting of H, alkoxy, and alkoxy-alkoxycarbonyl. Preferably, R$^7$ is a 3-, 4-, 5- or 6-membered carbocyclic ring, or a 5- or 6-membered heterocyclic ring which contains one or two ring O, N, or S atoms. Also preferred are embodiments wherein R$^7$ is a heterocyclic ring having one ring O, N, or S hetero atom, with a 3-, 4, 5- or 6-membered heterocyclic ring which contains one ring O atom being preferred.

In some particularly preferred embodiments, the constituent variables of the compounds of Formula II are selected in accordance with Table 7, infra.

In further more preferred embodiments of the compounds of Formula II, Q is $NR^{74}$; R5 and $R^8$ are H; W is $CH_2$; m is 0; G is a bond or $CH_2$; and R3 is independently selected from the group consisting of H, halogen, alkoxyalkyl, and alkoxyalkyl. Preferably, $R^{74}$ is a 3-, 4-, 5- or 6-membered carbocyclic ring, or a 5- or 6-membered heterocyclic ring which contains one or two ring O, N, or S atoms. Also preferred are embodiments wherein $R^{74}$ is a heterocyclic ring having one ring O, N, or S hetero atom, with a 3-, 4, 5- or 6-membered heterocyclic ring which contains one ring O atom being preferred.

In some particularly preferred embodiments, the constituent variables of the compounds of Formula II are selected in accordance with Table 8, infra.

In some preferred embodiments of the compounds of Formula II, $R^1$, $R^3$, $R^4$ and $R^6$ are each H; $A_1,A_2$ is H,H; $B_1,B_2$ is =O; Q is NH; $R^5$ is H or alkoxy; W is $CR^{18}R^7$ where $R^{18}$ is H; G is a bond; m is 1; $R^8$ is OH or —C(=O)$R^9$ where $R^9$ is alkyl; A is O; B, C and D are each $CHR^{17}$ where $R^{17}$ is H; and E and F are each a bond. In particularly preferred embodiments, $R^5$ is attached to the 10-position. In some especially preferred embodiments, $R^5$ is alkoxy, with —O—$CH_3$ being preferred. In further especially preferred embodiments, $R^8$ is —OH.

In further preferred embodiments of the compounds of Formula II, $R^1$, $R^3$, $R^4$ and $R^6$ are each H; $A_1,A_2$ is H,H; $B_1,B_2$ is =O; Q is NH; $R^5$ is H and is attached at the 10-position; W is $CR^{18}R^7$ where $R^{18}$ is H; G is a bond; m is 1; $R^8$ is OH or —C(=O)$R^9$ where $R^9$ is alkyl, with —OH being preferred; A is O; B, C and D are each $CHR^{17}$ where $R^{17}$ is H; and E and F are each a bond.

In further preferred embodiments, of the compounds of Formula II, $R^1$, $R^3$, $R^4$ and $R^6$ are each H; $A_1,A_2$ is H,H; $B_1,B_2$ is =O; Q is NH; $R^5$ is H and is attached at the 10-position; W is $CR^{18}R^7$ where $R^{18}$ is H; G is a bond; m is 1; $R^8$ acyloxy with —O—(C=O)—$CH_3$ being preferred; A is O; B, C and D are each $CHR^{17}$ where $R^{17}$ is H; and E and F are each a bond.

In further preferred embodiments of the compounds of Formula II, $R^1$, $R^3$, $R^4$ $R^5$ and $R^6$ are each H; $A_1,A_2$ is H,H; and $B_1,B_2$ is =O. In further preferred embodiments, Q is $NR^{74}$ and W is $CHR^{17}$, preferably where $R^{74}$ and $R^{17}$ are each cyclopropylmethyl.

In some preferred embodiments of the compounds of Formula I, $R^1$, $R^3$, $R^4$ $R^5$ and $R^6$ are each H; $A_1,A_2$ is H,H; $B_1,B_2$ is =O, W is $CH_2$, and Q is $NR^{74}$. In further preferred embodiments, G is $CH_2$, m is 0, $R^8$ is —CN, and ring J is cyclopropyl.

In further preferred embodiments of the compounds of Formula I, $R^1$, $R^3$, $R^4$ $R^5$ and $R^6$ are each H; $A_1,A_2$ is H,H; $B_1,B_2$ is =O, Q is NH, and W is $CR^{18}R^7$ where $R^{18}$ is H. In further preferred embodiments, G is CHOH, m is 0, $R^8$ is H, A and B form —CH=CH—, C is $CHR^{17}$ where $R^{17}$ is —$CH_3$, D is a bond, E and F are each N. In still further preferred embodiments, E and F are joined to form a fused heterocyclic ring which is substituted with 1 aryl group. Preferably, $R^7$ has the formula:

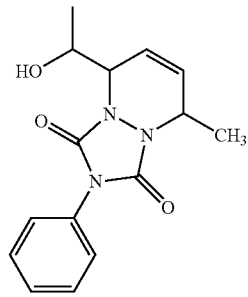

In further preferred embodiments of the compounds of Formula I, $R^1$, $R^3$, $R^4$ $R^5$ and $R^6$ are each H; $A_1,A_2$ is H,H; $B_1,B_2$ is =O, W is $CH_2$, and Q is $NR^{74}$, G is ethylene, m is 0, $R^8$ is H, A is NH, B is $CHR^{17}$, C and D are each a bond, E is $CH_2$ and F is S, preferably wherein $R^{17}$ is alkoxycarbonyl, with methoxycarbonyl being more preferred.

The compounds of the invention are useful, inter alia, for enhancing trophic factor-induced activities of trophic factor responsive cells, e.g., cholinergic neurons, and may also function as survival-promoting agents for other neuronal cell types, e.g., dopaminergic and glutamatergic, and are thus beneficial pharmacological and therapeutic agents. The present compounds are also useful in the treatment of disorders associated with decreased ChAT activity or the death or injury to spinal cord motoneurons, and also have utility in diseases associated with apoptotic cell death of the central and peripheral nervous system, immune system, and in inflammatory diseases.

The cyclic substituted fused pyrrolocarbazoles and isoindolone compounds described herein may also find utility in the treatment of disease states involving malignant cell proliferation, such as cancer.

Thus, also provided in accordance with the present invention are method for inhibiting a kinase comprising providing a compound of claim 1 in an amount sufficient to result in effective inhibition. Preferably, the kinase is selected from trk kinase, particularly trk A, VEGFR, MLK, and FGFR.

In some preferred embodiments, methods of the invention are provided to treat inflammation. In further preferred embodiments, methods are provided for treating or preventing prostate disorders which comprises administering to a host in need of such treatment or prevention a therapeutically effective amount of a compound of the invention. In some preferred embodiments, the prostate disorder is prostate cancer or benign prostate hyperplasia.

In further preferred embodiments of the methods of the invention, method are provided for treating or preventing disorders where VEGFR activity contributes to pathological conditions comprising providing a compound of the invention in an amount sufficient to result in the platelet derived growth factor receptor being contacted with an effective inhibitory amount of the compound, preferably wherein the disorder is cancer, endometriosis, psoriasis, hemangioblastoma, or an ocular disease, and more preferably wherein the disorder is a solid tumor, a hematopoietic or lymphatic malignancy, or an ocular disease which is preferably diabetic retinopathy.

In further preferred embodiments of the methods of the invention, methods are provided for treating or preventing disorders where PDGFR activity contributes to pathological conditions comprising providing a compound of the invention in an amount sufficient to result in the platelet derived growth factor receptor being contacted with an effective inhibitory amount of the compound.

In further preferred embodiments of the methods of the invention, method are provided for treating or preventing neoplasia, rheumatoid arthritis, pulmonary fibrosis, myelofibrosis, abnormal wound healing, atherosclerosis, or restenosis which comprises administering to a host in need of such treatment or prevention a therapeutically effective amount of a compound of the invention.

In further preferred embodiments of the methods of the invention, method are provided for treating or preventing disorders characterized by the aberrant activity of trophic factor responsive cells comprising providing a compound of the invention in an amount sufficient to result in the trophic factor cell receptor being contacted with an effective activity inducing amount of the compound.

In still further preferred embodiments of the methods of the invention, method are provided for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, or injuries of the brain or spinal chord which comprises administering to a host in need of such treatment or prevention a therapeutically effective amount of a compound of the invention.

In further preferred embodiments of the methods of the invention, method are provided for treating or preventing disorders characterized by the aberrant activity of a protein kinase which comprises administering to a host in need of such treatment or prevention a therapeutically effective amount of a compound of the invention.

In still further preferred embodiments of the methods of the invention, method are provided for treating or preventing disorders where either the vascular endothelial growth factor receptor (VEGFR) kinase, trkA tyrosine kinase (trkA), mixed lineage kinase (MLK) or the fibroplast growth factor receptor kinase (FGFR) contributes to pathological conditions, the method comprising providing a compound of the invention in an amount sufficient to result in the receptor being contacted with an effective inhibitory amount of the compound.

In some preferred embodiments of the methods of the invention, methods are provided for treating or preventing a disease mediated by a kinase selected from ab1, AKT, bcr-ab1, Blk, Brk, Btk, c-kit, c-met, c-src, CDK1, CDK2, CDK4, CDK6, chk1, chk2, cRaf1, CSF1R, CSK, EGFR, ErbB2, ErbB3, ErbB4, ERK (Eph), ERK 2, Fak, fes, FGFR1, FGFR2, FGFR3, FGFR4, FGFR5, Fgr, FLK-4, flt-1, Fps, Frk, Fyn, GSK, Hck, IGF-1R, INS-R, Jak, JNK, tau, VEGFR1, VEGFR2, VEGFR3, Lck, Lyn, MEK, p38, PDGFR, PIK, PKC, PYK2, ros, tie$_1$, tie$_2$, TRK, UL97, Yes and Zap70, the method comprising administering to a patient in need of such treatment or prevention a pharmaceutically effective amount of a compound of the invention.

In further preferred embodiments methods are provided for treating or preventing disorders where a kinase selected from ab1, AKT, bcr-ab1, Blk, Brk, Btk, c-kit, c-met, c-src, CDK1, CDK2, CDK4, CDK6, chk1, chk 2, cRaf1, CSF1R, CSK, EGFR, ErbB2, ErbB3, ErbB4, ERK (Eph), ERK 2, Fak, fes, FGFR1, FGFR2, FGFR3, FGFR4, FGFR5, Fgr, FLK-4, flt-1, Fps, Frk, Fyn, GSK, Hck, IGF-1R, INS-R, Jak, JNK, tau, VEGFR1, VEGFR2, VEGFR3, Lck, Lyn, MEK, p38, PDGFR, PIK, PKC, PYK2, ros, tie$_1$, tie$_2$, TRK, UL97, Yes and Zap70 contributes to pathological conditions, the method comprising providing a compound of the invention in an amount sufficient to result in the receptor being contacted with an effective inhibitory amount of the compound.

Also provided in accordance with preferred embodiments of the invention are methods for treating or preventing a symptom of a disorder where a kinase selected from ab1, AKT, bcr-ab1, Blk, Brk, Btk, c-kit, c-met, c-src, CDK1, CDK2, CDK4, CDK6, chk1, chk 2, cRaf1, CSF1R, CSK, EGFR, ErbB2, ErbB3, ErbB4, ERK (Eph), ERK 2, Fak, fes, FGFR1, FGFR2, FGFR3, FGFR4, FGFR5, Fgr, FLK-4, flt-1, Fps, Frk, Fyn, GSK, Hck, IGF-1R, INS-R, Jak, JNK, tau, VEGFR1, VEGFR2, VEGFR3, Lck, Lyn, MEK, p38, PDGFR, PIK, PKC, PYK2, ros, tie$_1$, tie$_2$, TRK, UL97, Yes and Zap70 contributes to such symptom, the method comprising providing a compound of the invention in an amount sufficient to result in the receptor being contacted with an effective inhibitory amount of the compound.

The present invention further provides methods for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, injuries of the brain or spinal chord, cancer, restenosis, osteoporosis, inflammation, angiogenesis, viral infections, bone or hematopoetic diseases, autoimmune diseases or transplant rejection which comprises administering to a host in need of such treatment or prevention a therapeutically effective amount of a compound of the invention.

Also provided in accordance with the present invention are methods for the treatment of cancer comprising inhibiting one or more of Src, raf, or a cell cycle kinase. Preferably, the cell cycle kinase is a cyclin-dependent kinase or a checkpoint kinase. Preferably, the cyclin-dependent kinase is CDK 1, 2, 4 or 6, and the checkpoint kinase is chk 1 or chk 2.

Compositions containing the subject compounds, and methods for using the subject compounds, are disclosed. Methodologies for making the cyclic substituted aryl and heteroaryl-fused pyrrolocarbazoles and isoindolones are also disclosed. Other useful methodologies will be apparent to those skilled in the art, once armed with the present disclosure. These and other features of the compounds of the subject invention are set forth in more detail below.

BRIEF DESCRIPTION OF THE DRAWINGS

FIG. 8 is a schematic drawing showing a general preparation of a cyclic compound of the invention using a preferred appropriately substituted cyclic intermediate as an electrophile.

FIG. 11 is a schematic drawing showing the preparation of soluble and resin-bound N-lactam protected fused pyrrolocarbazoles.

FIG. 17 is another schematic drawing showing a general preparation of a cyclic compound of the invention by reaction of a carbanion intermediate with highly electrophilic reagents.

FIG. 21 is another schematic drawing showing a general preparation of a cyclic compound of the invention in which the cyclic substituent is formed from an aldehyde intermediate.

DETAILED DESCRIPTION

Figure 1:
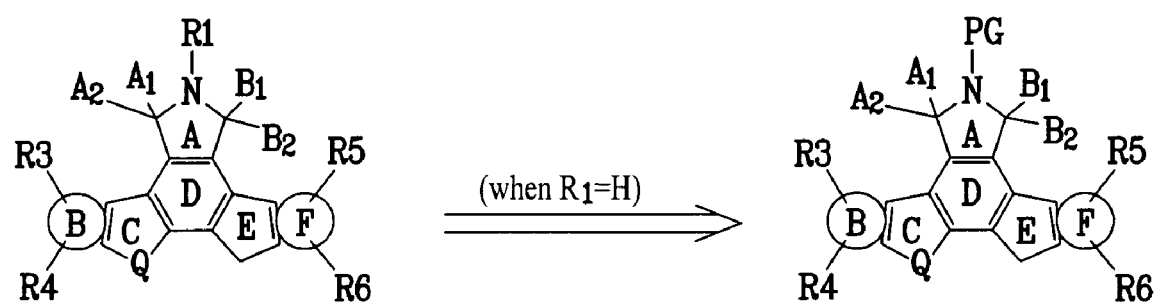
FIG. 1 is a schematic drawing showing a preparation of an R$^1$ protected fused pyrrolocarbazoles and isoindolones.

Disclosed herein are cyclic substituted fused pyrrolocarbazoles and isoindolones, which are represented by the following Formula I:

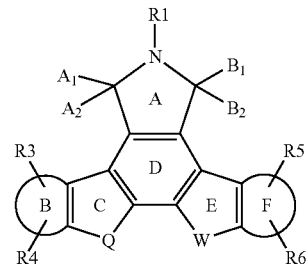

wherein:

ring B and ring F, independently, and each together with the carbon atoms to which they are attached, are selected from the group consisting of:
  a) an unsaturated 6-membered carbocyclic aromatic ring in which from 1 to 3 carbon atoms may be replaced by nitrogen atoms;
  b) an unsaturated 5-membered carbocyclic aromatic ring; and
  c) an unsaturated 5-membered carbocyclic aromatic ring in which either
    1) one carbon atom is replaced with an oxygen, nitrogen, or sulfur atom;
    2) two carbon atoms are replaced with a sulfur and a nitrogen atom, an oxygen and a nitrogen atom, or two nitrogen atoms; or
    3) three carbon atoms are replaced with three nitrogen atoms;

$R^1$ is selected from the group consisting of:
  a) H, substituted or unsubstituted alkyl having from 1 to 4 carbons, substituted or unsubstituted aryl, substituted or unsubstituted arylalkyl, substituted or unsubstituted heteroaryl, or substituted or unsubstituted heteroarylalkyl;
  b) —C(=O)$R^9$, where $R^9$ is selected from the group consisting of alkyl, aryl and heteroaryl;
  c) —O$R^{10}$, where $R^{10}$ is selected from the group consisting of H and alkyl having from 1 to 4 carbons;
  d) —C(=O)NH$_2$, —NR$^{11}$R$^{12}$, —(CH$_2$)$_p$NR$^{11}$R$^{12}$, —(CH$_2$)$_p$OR$^{10}$, —O(CH$_2$)$_p$OR$^{10}$ and —O(CH$_2$)$_p$NR$^{11}$R$^{12}$, wherein p is from 1 to 4; and wherein either
    1) $R^{11}$ and $R^{12}$ are each independently selected from the group consisting of H and alkyl having from 1 to 4 carbons; or
    2) $R^{11}$ and $R^{12}$ together form a linking group of the formula —(CH$_2$)$_2$—X$^1$—(CH$_2$)$_2$—, wherein X$^1$ is selected from the group consisting of —O—, —S—, and —CH$_2$—;

$R^2$ is selected from the group consisting of H, alkyl having from 1 to 4 carbons, —OH, alkoxy having from 1 to 4 carbons, —OC(=O)$R^9$, —OC(=O)NR$^{11}$R$^{12}$, —O(CH$_2$)$_p$NR$^{11}$R$^{12}$, —O(CH$_2$)$_p$OR$^{10}$, substituted or unsubstituted arylalkyl having from 6 to 10 carbons, and substituted or unsubstituted heteroarylalkyl;

$R^3$, $R^4$, $R^5$ and $R^6$ are each independently selected from the group consisting of:
  a) H, aryl, heteroaryl, F, Cl, Br, I, —CN, CF$_3$, —NO$_2$, —OH, —OR$^9$, —O(CH$_2$)$_p$NR$^{11}$R$^{12}$, —OC(=O)$R^9$, —OC(=O)NR$^{11}$R$^{12}$, —O(CH$_2$)$_p$OR$^{10}$, —CH$_2$OR$^{10}$, —NR$^{11}$R$^{12}$, —NR$^{10}$S(=O)$_2$R$^9$, —NR$^{10}$C(=O)$R^9$, b) —CH$_2$OR$^{14}$, wherein R$^{14}$ is the residue of an amino acid after the hydroxyl group of the carboxyl group is removed;

c) —NR$^{10}$C(=O)NR$^{11}$R$^{12}$, —CO$_2$R$^2$, —C(=O)R$^2$, —C(=O)NR$^{11}$R$^{12}$, —CH=NOR$^2$, —CH=NR$^9$, —(CH$_2$)$_p$NR$^{11}$R$^{12}$, —(CH$_2$)$_p$NHR$^{14}$, or —CH=NNR$^2$R$^{24}$ wherein R$^{24}$ is the same as R$^2$;

d) —S(O)$_y$R$^2$, —(CH$_2$)$_p$S(O)$_y$R$^9$, —CH$_2$S(O)$_y$R$^{14}$ wherein y is 0, 1 or 2;

e) alkyl having from 1 to 8 carbons, alkenyl having from 2 to 8 carbons, and alkynyl having 2 to 8 carbons, wherein 1) each alkyl, alkenyl, or alkynyl group is unsubstituted; or 2) each alkyl, alkenyl or alkynyl group is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$R$^{11}$R$^{12}$, —X$^2$(CH$_2$)$_p$C(=O)NR$^{11}$R$^{12}$, —X$^2$(CH$_2$)$_p$OC(=O)NR$^{11}$R$^{12}$, —X$^2$(CH$_2$)$_p$CO$_2$R$^9$, X$^2$(CH$_2$)$_p$S(O)$_y$R$^9$, —X$^2$(CH$_2$)$_p$NR$^{10}$C(=O)NR$^{11}$R$^{12}$, —OC(=O)R$^9$, —OCONHR$^2$, —O-tetrahydropyranyl, —NR$^{11}$R$^{12}$, —NR$^{10}$CO$_2$R$^9$, —NR$^{10}$C(=O)NR$^{11}$R$^{12}$, —NHC(=NH)NH$_2$, NR$^{10}$C(=O)R$^9$, —NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{24}$, —CH=NOR$^2$, —CH=NR$^9$, —CH=NNHCH(N=NH)NH$_2$, —S(=O)$_2$NR$^2$R$^{24}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

X$^2$ is O, S, or NR$^{10}$;

R$^7$ is

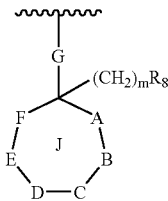

wherein:
 m is 0–4;
 G is a bond; or alkylene having 1 to 4 carbons, wherein the alkylene group is unsubstituted, or substituted with NR$^{114}$R$^{124}$ or OR$^{19}$;
 R$^{114}$ and R$^{124}$ are the same as R$^{11}$ and R$^{12}$;
 R$^{19}$ is selected from the group consisting of H, alkyl, acyl, and C(=O)NR$^{114}$R$^{124}$;
 R$^8$ is selected from the group consisting of O(C=O)NR$^{11}$R$^{12}$, —CN, acyloxy, alkenyl, —O—CH$_2$—O—(CH$_2$)$_2$—O—CH$_3$, halogen and R$^{14}$ wherein R$^{14}$ is the same as R$^1$;
 A and B are independently selected from the group consisting of O, N, S, CHR$^{17}$, C(OH)R$^{17}$, C(=O), and CH$_2$=C; or A and B together can form —CH=CH—;
 C and D are independently selected from the group consisting of a bond, O, N, S, CHR$^{17}$, C(OH)R$^{17}$, C(=O) and CH$_2$=C;
 E and F are independently selected from the group consisting of a bond, O, N, S, C(=O), and CH(R$^{17}$);
 R$^{17}$ is selected from the group consisting of H, substituted or unsubstituted alkyl, alkoxycarbonyl, and substituted or unsubstituted alkoxy;
 wherein:
  1) ring J contains 0 to 3 ring heteroatoms;
  2) any two adjacent hydroxyl groups of ring J can be joined in a dioxolane ring;
  3) any two adjacent ring carbon atoms of ring J can be joined to form a fused aryl or heteroaryl ring;
  4) any two adjacent ring nitrogen atoms of ring J can be joined to form a fused heterocyclic ring which can be substituted with 1 to 3 alkyl or aryl groups;
 provided that:
  1) ring J contain at least one carbon atom that is saturated;
  2) ring J not contain two adjacent ring O atoms;
  3) ring J contains a maximum of two ring C(=O) groups;
  4) when G is a bond, ring J can be heteroaryl;

Q is selected from the group consisting of O, S, NR$^{13}$, NR$^{74}$ wherein R$^{74}$ is the same as R$^7$, CHR$^{15}$, X$^3$CH(R$^{15}$), and CH(R$^{15}$)X$^3$, wherein X$^3$ is selected from the group consisting of —O—, —S—, —CH$_2$—, NR$^{74}$, and NR$^3$;

W is selected from the group consisting of CR$^{18}$R$^7$ and CHR$^2$;
 R$^{13}$ is selected from the group consisting of H, —SO$_2$R$^9$, —CO$_2$R$^9$, —C(=O)R$^9$, —C(=O)NR$^{11}$R$^{12}$, alkyl of 1–8 carbons, alkenyl having 2–8 carbons, and alkynyl having 2–8 carbons; and either 1) the alkyl, alkenyl, or alkynyl group is unsubstituted; or 2) the alkyl, alkenyl, or alkynyl group independently is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$NR$^{11}$R$^{12}$, —X$^2$(CH$_2$)$_p$C(=O)NR$^{11}$R$^{12}$, —X$^2$(CH$_2$)$_p$OC(=O)NR$^{11}$R$^{12}$, —X$^2$(CH$_2$)$_p$CO$_2$R$^9$, X$^2$(CH$_2$)$_p$S(O)$_y$R$^9$, —X$^2$(CH$_2$)$_p$NR$^{10}$C(=O)NR$^{11}$R$^{12}$, —OC(=O)R$^9$, —OCONHR$^2$, —O-tetrahydropyranyl, —NR$^{11}$R$^{12}$, —NR$^{10}$CO$_2$R$^9$, —NR$^{10}$C(=O)NR$^{11}$R$^{12}$, —NHC(=NH)NH$_2$, NR$^{10}$C(=O)R$^9$, —NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{24}$, —CH=NOR$^2$, —CH=NR$^9$, —CH=NNHCH(N=NH)NH$_2$, —S(=O)$_2$NR$^2$R$^{24}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

$R^{15}$ is selected from the group consisting of H, $OR^{10}$, $SR^{10}$, $R^{74}$, and $R^{16}$;

$R^{16}$ is selected from the group consisting of alkyl of 1 to 4 carbons; phenyl; naphthyl; arylalkyl having 7 to 15 carbons, —$SO_2R^9$, —$CO_2R^9$, —C(=O)$R^9$, alkyl having 1–8 carbons; alkenyl having 2 to 8 carbons, and alkynyl having 2 to 8 carbons, wherein 1) each alkyl, alkenyl, or alkynyl group is unsubstituted; or
2) each alkyl, alkenyl, or alkynyl group is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, —CN, —$NO_2$, —OH, —$OR^9$, —$X^2(CH_2)_pNR^{11}R^{12}$, —$X^2(CH_2)_p$ C(=O) $NR^{11}R^{12}$, —$X^2(CH_2)_pOC(=O)NR^{11}R^{12}$, —$X^2(CH_2)_pCO_2R^9$, $X^2(CH_2)_pS(O)_yR^9$, —$X^2(CH_2)_pNR^{10}C(=O)NR^{11}R^{12}$, —OC(=O)$R^9$, —$OCONHR^2$, —O-tetrahydropyranyl, —$NR^{11}R^{12}$, —$NR^{10}CO_2R^9$, —$NR^{10}C(=O)NR^{11}R^{12}$, —NHC(=NH)$NH_2$, $NR^{10}C(=O)R^9$, —$NR^{10}S(O)_2R^9$, —$S(O)_yR^9$, —$CO_2R^2$, —C(=O)$NR^{11}R^{12}$, —C(=O)$R^2$, —$CH_2OR^{10}$, —CH=$NNR^2R^{24}$, —CH=$NOR^2$, —CH=$NR^9$, —CH=NNHCH(N=NH)$NH_2$, —S(=O)$_2$ $NR^2R^{24}$, —P(=O)$(OR^{10})_2$, —$OR^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

$R^{18}$ is selected from the group consisting of $R^2$, thioalkyl of 1–4 carbons, and halogen;

$A^1$ and $A^2$ are selected from the group consisting of H, H; H, $OR^2$; H, —$SR^2$; H, —$N(R^2)_2$; and a group wherein $A^1$ and $A^2$ together form a moiety selected from the group consisting of =O, =S, and =$NR^2$;

$B^1$ and $B^2$ are selected from the group consisting of H, H; H, —$OR^2$; H, —$SR^2$; H, —$N(R^2)_2$; and a group wherein $B^1$ and $B^2$ together form a moiety selected from the group consisting of =O, =S, and =$NR^2$; with the proviso that at least one of the pairs $A^1$ and $A^2$, or $B^1$ and $B^2$, form =O;

with the proviso that when Q is NH or $NR^{74}$, and in any $R^7$ or $R^{74}$ group m is 0 and G is a bond, $R^8$ is H, and $R^7$ or $R^{74}$ contains one ring hetero oxygen atom at position A in a 5- or 6-membered ring, then B cannot be $CHR^{17}$ where $R^{17}$ is substituted or unsubstituted alkyl; and with the further proviso that the compound of Formula I contains one $R^7$ or $R^{74}$ group or both an $R^7$ and $R^{74}$ group.

The compounds of the invention include both diasteriomers and enantiomers.

Preferred cyclic substituted fused pyrrolocarbazoles and isoindolones are represented by the following formula:

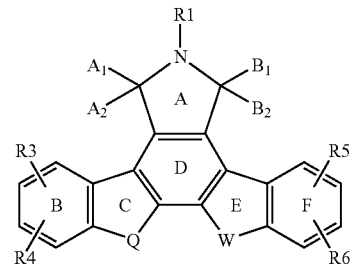

The compounds represented by Formula (I) are hereinafter referred to as Compound (I), and the same applies to the compounds of other formula numbers.

As used herein, the term "carbocyclic" refers to cyclic groups in which the ring portion is composed solely of carbon atoms. The terms "heterocyclo" and "heterocyclic" refer to cyclic groups in which the ring portion includes at least one heteroatom such as O, N, or S.

As used herein, the term "alkyl" means a straight-chain, cyclic, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, hexyl, octyl, cyclopropyl, and cyclopentyl. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. The term "alkenyl" is intended to include straight-chain or branched hydrocarbon chains having at least one carbon-carbon double bond. Examples of alkenyl groups include ethenyl and propenyl groups. As used herein, the term "alkynyl" is intended to include straight-chain or branched hydrocarbon chains having at least one carbon-carbon triple bond. Examples of alkynyl groups include ethynyl and propynyl groups.

The acyl moiety of acyl-containing groups such as acyloxy groups is intended to include a straight-chain or branched alkanoyl group having 1 to 6 carbon atoms, such as formyl, acetyl, propanoyl, butyryl, valeryl, pivaloyl or hexanoyl.

As used herein the term "aryl" means a group having 6 to 12 carbon atoms such as phenyl, biphenyl and naphthyl. Preferred aryl groups include unsubstituted or substituted phenyl and naphthyl groups. The term "heteroaryl" as used herein denotes an aryl group in which one or more ring carbon atom is replaced by a hetero (i.e., non-carbon) atom such as O, N or S. Preferred heteroaryl groups include pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups.

The term "aralkyl" (or "arylalkyl") is intended to denote a group having from 7 to 15 carbons, consisting of an alkyl group that bears an aryl group. Examples of aralkyl groups include benzyl, phenethyl, benzhydryl and naphthylmethyl groups. Alkyl groups and alkyl moieties contained within substituent groups such as aralkyl, alkoxy, arylalkoxy, hydroxyalkoxy, alkoxy-alkoxy, hydroxy-alkylthio, alkoxy-alkylthio, alkylcarbonyloxy, hydroxyalkyl and acyloxy groups may be substituted or unsubstituted. A substituted alkyl group has 1 to 3 independently-selected substituents, preferably hydroxy, lower alkoxy, lower alkoxy-alkoxy, substituted or unsubstituted arylalkoxy-lower alkoxy, substituted or unsubstituted heteroarylalkoxy-lower alkoxy, substituted or unsubstituted arylalkoxy, substituted or unsubstituted heterocycloalkoxy, halogen, carboxyl, lower alkoxycarbonyl, nitro, amino, mono- or dII-lower alkylamino, dioxolane, dioxane, dithiolane, dithione, furan, lactone, or lactam.

Substituted aryl, substituted heteroaryl and substituted aralkyl groups each have 1 to 3 independently-selected substituents that are preferably lower alkyl, hydroxy, lower alkoxy, carboxy, lower alkoxycarbonyl, nitro, amino, mono- or di-lower alkylamino, and halogen.

Heterocyclic groups formed with a nitrogen atom include pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, pyrazole, pyrazolone, oxadiazole, thiadiazole, and triazole groups. Heterocyclic groups formed with an oxygen atom include furan, tetrahydrofuran, pyran, 1,3-dioxolane, 1,3-dioxinane, 1,4-dioxinane, 1,3-oxathinane, 1,4-oxathinane, 1,3-oxathiolane, and tetrahydropyran groups.

"Hydroxyalkyl" groups are alkyl groups that have a hydroxyl group appended thereto. "Hydroxyalkoxy" groups are alkoxy groups that have a hydroxyl group appended thereto. Halogens include fluorine, chlorine, bromine and iodine.

As used herein, the term "heteroarylalkyl" means an arylalkyl group that contains a heteroatom. The term "oxy" denotes the presence of an oxygen atom. Thus, "alkoxy" groups are alkyl groups that are attached through an oxygen atom, and "carbonyloxy" groups are carbonyl groups that are attached through an oxygen atom.

The term "heterocycloalkoxy" means an alkoxy group that has a heterocyclo group attached to the alkyl moiety thereof, and the term "arylalkoxy" means an alkoxy group that has an aryl group attached to the alkyl moiety thereof. The term "alkylcarbonyloxy" means a group of formula —O—C(═O)-alkyl.

As used herein, the term "alkyloxy-alkoxy" denotes an alkoxy group that contains an alkyloxy substituent attached to its alkyl moiety. The term "alkoxy-alkylthio" means an alkylthio group (i.e., a group of formula —S-alkyl) that contains an alkoxy substituent attached to its alkyl moiety. The term "hydroxy-alkylthio" means an alkylthio group (i.e., a group of formula —S-alkyl) that contains a hydroxy substituent attached to its alkyl moiety. The term "alkoxy-alkylthio" means an alkylthio group that contains an alkoxy substituent attached to its alkyl moiety.

As used herein, the term "monosaccharide" has its accustomed meaning as a simple sugar.

As used herein, the term "amino acid" denotes a molecule containing both an amino group and a carboxyl group. Embodiments of amino acids include αα-amino acids; i.e., carboxylic acids of general formula HOOC—CH(NH2)-(side chain).

Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, Biochemistry, Second Edition, Worth Publishers, Inc, 1975, pages 73–75, incorporated by-reference herein.

In some preferred embodiments, substituent groups for the compounds of Formulas I and II include the residue of an amino acid after removal of the hydroxyl moiety of the carboxyl group thereof; i.e., groups of Formula —C(═O)—CH(NH2)-(side chain).

Functional groups present on the compounds of Formula I may contain protecting groups. For example, the amino acid sidechain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. One such protecting group is the benzyloxycarbonyl (Cbz; Z) group. Other preferred protecting groups according to the invention may be found in Greene, T. W. and Wuts, P. G. M., "Protective Groups in Organic Synthesis" 2 d. Ed., Wiley & Sons, 1991.

The cyclic substituted fused pyrrolocarbazoles and isoindolone compounds have evidenced important functional pharmacological activities which find utility in a variety of settings, including both research and therapeutic arenas. These derivatives are useful as therapeutic agents. The activities of the compounds show positive effects on the function and/or survival of trophic factor responsive cells. Effect on the function and/or survival of trophic factor responsive cells, e.g., cells of a neuronal lineage, has been demonstrated using any of the following assays: (1) cultured spinal cord choline acetyltransferase ("ChAT") assay; or (2) cultured basal forebrain neuron ChAT activity assay.

As used herein, the term "effect" when used to modify the terms "function" and "survival" means a positive or negative alteration or change. An effect, which is positive, can be referred to herein as an "enhancement" or "enhancing" and an effect, which is negative, can be referred to herein as "inhibition" or "inhibiting."

As used herein, the terms "enhance" or "enhancing" when used to modify the terms "function" or "survival" means that the presence of a cyclic substituted fused pyrrolocarbazole or isoindolone compound has a positive effect on the function and/or survival of a trophic factor responsive cell compared with a cell in the absence of the compound. For example, and not by way of limitation, with respect to the survival of, e.g., a cholinergic neuron, the compound would evidence enhancement of survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

As used herein, "inhibit" and "inhibition" mean that a specified response of a designated material (e.g., enzymatic activity) is comparatively decreased in the presence of a cyclic substituted fused pyrrolocarbazole or isoindolone compound.

As used herein, the term "trk" refers to the family of high affinity neurotrophin receptors presently comprising trk A, trk B, and trk C, and other membrane associated proteins to which a neurotrophin can bind.

As used herein, inhibition of VEGFR implies utility in, for example, diseases where angiogenesis plays important roles, such as cancer of solid tumors, endometriosis, diabetic retinopathy, psoriasis, hemangioblastoma, as well as other ocular diseases and cancers.

Inhibition of trk implies utility in, for example, diseases of the prostate such as prostate cancer and benign prostate hyperplasia, and treatment of inflammatory pain.

Inhibition of Platelet Derived Growth Factor Receptor (PDGFR) implies utility in, for example, various forms of neoplasia, rheumatoid arthritis, pulmonary fibrosis, myelofibrosis, abnormal wound healing, diseases with cardiovascular end points, such as atherosclerosis, restenosis, post-angioplasty restenosis, etc.

As used herein, the terms "cancer" and "cancerous" refer to any malignant proliferation of cells in a mammal. Examples include prostate, benign prostate hyperplasia, ovarian, breast, brain, lung, pancreatic, colorectal, gastric, stomach, solid tumors, head and neck, neuroblastoma, renal cell carcinoma, lymphoma, leukemia, other recognized malignancies of the hematopoietic systems, and other recognized cancers.

As used herein the terms "neuron," "cell of neuronal lineage" and "neuronal cell" include, but are not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain, striatal, and spinal cord neurons. As used herein, the phrase "sensory neuron" includes neurons responsive to environmental cues (e.g., temperature, movement) from, e.g., skin, muscle and joints; exemplary is a neuron from the dorsal root ganglion.

A "trophic factor-responsive cell," as defined herein, is a cell which includes a receptor to which a trophic factor can specifically bind; examples include neurons (e.g., cholinergic and sensory neurons) and non-neuronal cells (e.g., monocytes and neoplastic cells).

The cyclic substituted fused pyrrolocarbazole and isoindolone compounds described herein find utility in both research and therapeutic settings in, for example, inhibition of enzymatic activity. For example, in a research environment, the compounds can be used in the development of assays and models for further enhancement of the understanding of the roles that inhibition of serine/threonine or tyrosine protein kinase (e.g., PKC, trk tyrosine kinase) play in the mechanistic aspects of the associated disorders and diseases. In a therapeutic setting, the compounds which inhibit these enzymatic activities can be used to inhibit the deleterious consequences of these enzymes with respect to disorders such as cancer.

As the Examples below demonstrate, inhibition of enzymatic activity using the cyclic substituted fused pyrrolocarbazole and isoindolone compounds can be determined using, for example, the following assays:

1. trkA Tyrosine Kinase Activity inhibition assay;
2. Inhibition of NGF-stimulated trk phosphorylation in a whole cell preparation;
3. Vascular Endothelial Growth Factor Receptor(VEGFR) kinase inhibition assay;
4. PKC Activity inhibition assay;
5. PDGFR inhibition assay.
6. Enhancement of Spinal Cord ChAT Activity The disclosed cyclic substituted fused pyrrolocarbazole and isoindolone compounds can be used to enhance the function and/or survival of cells of neuronal lineage in a mammal, e.g., a human. In these contexts, the compounds can be utilized individually or with other fused pyrrolocarbazoles and/or indolocarbazoles, or in combination with other beneficial molecules which also evidence the ability to effect the function and/or survival of a designated cell.

The cyclic substituted fused pyrrolocarbazoles and isoindolones of the present invention are useful, inter alia, as therapeutic agents. Particularly, the compounds are useful for protein kinase inhibition. The cyclic substituted fused pyrrolocarbazoles and isoindolones may inhibit, for example, kinases selected from ab1, AKT, bcr-ab1, Blk, Brk, Btk, c-kit, c-met, c-src, CDK1, CDK2, CDK4, CDK6, chk1, chk2, cRaf1, CSF1R, CSK, EGFR, ErbB2, ErbB3, ErbB4, ERK (Eph), ERK 2, Fak, fes, FGFR1, FGFR2, FGFR3, FGFR4, FGFR5, MLK1, MLK2, MLK3, DLK, trkA, trkB, trkC, Fgr, FLK-4, flt-1, Fps, Frk, Fyn, GSK, Hck, IGF-1R, INS-R, Jak, JNK, tau, VEGFR1, VEGFR2, VEGFR3, Lck, Lyn, MEK, p38, PDGFR, PIK, PKC, PYK2, ros, tie$_1$, tie$_2$, UL97, Yes and Zap70.

Thus, the properties of the compounds of the present invention are beneficial in therapeutic settings. The activities of the cyclic substituted fused pyrrolocarbazoles and isoindolones toward certain enzymes can be exploited to combat the deleterious consequences of these enzymes. For example, inhibition of the Vascular Endothelial Growth Factor Receptor (VEGFR) implies utility in, for example, diseases where angiogenesis plays important roles, such as cancer (for example solid tumors and hematopoietic/lymphatic malignancies), endometriosis, diabetic retinopathy, psoriasis, hemangioblastoma, as well as other ocular diseases and cancers. Inhibition of trk implies utility in, for example, diseases of the prostate such as prostate cancer and benign prostate hyperplasia, and treatment of inflammatory pain. Inhibition of the Platelet Derived Growth Factor Receptor (PDGFR) implies utility in, for example, various forms of neoplasia, rheumatoid arthritis, pulmonary fibrosis, myelofibrosis, abnormal wound healing, diseases with cardiovascular end points, such as atherosclerosis, restenosis, post-angioplasty restenosis, and the like. Inhibition of mixed lineage kinase (MLK) implies utility in, for example, Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; and disorders associated with concussive or penetrating injuries of the brain or spinal cord.

Inhibition of fibroplast growth factor receptor kinase (FGFR) implies utility in, for example, restenosis, post-angioplasty restenosis, atherosclerosis, pulmonary fibrosis, various cancers including, but not limited to, prostate cancer, breast cancer, abnormal wound healing, and benign prosthetic hypertrophy.

The activities of cyclic substituted fused pyrrolocarbazoles and isoindolones may also have positive effects on the function and survival of trophic factor responsive cells by promoting the survival of neurons. With respect to the survival of a cholinergic neuron, for example, the compound may preserve the survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

A variety of neurological disorders are characterized by neuronal cells which are dying, injured, functionally compromised, undergoing axonal degeneration, at risk of dying, etc.. These disorders include, but are not limited to: Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; and disorders associated with concussive or penetrating injuries of the brain or spinal cord.

Additionally, inhibition of Src, raf, and cell cycle kinases such as the cyclin-dependent kinases (CDK) 1, 2, 4 and 6, and checkpoint kinases (such as chk 1 and chk 2) may be useful for the treatment of cancer. Regulation of CDK2 kinase may be useful for the treatment of restenosis. Regulation of one or more of CDK5 or GSK3 kinases may be useful for the treatment of Alzheimers. Regulation of one or more of c-Src kinase may be useful for the treatment of osteoporosis. Regulation of one or more of GSK-3 kinase may be useful for the treatment of type-2 diabetes. Regulation of one or more of p38 kinase may be useful for the treatment of inflammation. Regulation of one or more of TIE-1, or TIE-2 kinases may be useful for the treatment of angiogenesis. Regulation of one or more of UL97 kinase may be useful for the treatment of viral infections. Regulation of one or more of CSF-1R kinase may be useful for the treatment of bone and hematopoetic diseases. Regulation of one or more of and Lck kinase may be useful for the treatment autoimmune diseases and transplant rejection. Regulation of topoisomerases Topo-I or Topo II may be useful for the treatment of cancer.

ChAT catalyzes the synthesis of the neurotransmitter acetylcholine, and it is considered an enzymatic marker for a functional cholinergic neuron. A functional neuron is also capable of survival. Neuron survival is assayed by quantitation of the specific uptake and enzymatic conversion of a dye (e.g., calcein AM) by living neurons.

Because of their varied utilities, cyclic substituted fused pyrrolocarbazole and isoindolone compounds disclosed herein find utility in a variety of settings, for example research. The compounds can be used in the development of in vitro models of neuronal cell survival, function, identification, or for the screening of other synthetic compounds which have activities similar to that of the of cyclic substituted fused pyrrolocarbazole and isoindolone compounds. Thus, the compounds provided by this invention are useful as standard or reference compounds for use in tests or assays for determining the activity of an agent in a pharmaceutical research program, and/or otherwise can be utilized in a research environment to investigate, define and determine molecular targets associated with functional responses. For example, by radiolabelling a cyclic substituted fused pyrrolocarbazole or isoindolone compound associated with a specific cellular function (e.g., mitogenesis), the target entity to which the derivative binds can be identified, isolated, and purified for characterization.

The compounds are useful, inter alia, not only for enhancing trophic factor-induced activities of trophic responsive cells, e.g., cholinergic neurons, but also may function as survival promoting agents for other neuronal cell types, e.g., dopaminergic or glutamatergic. Growth factor may regulate survival of neurons by signaling cascades downstream of the small GTP binding proteins ras, rac, and cdc42 (Denhardt, D. T., Biochem. J., 1996, 318, 729). Specifically, activation of ras leads to phosphorylation and activation of extracellular receptor-activated kinase (ERK), which has been linked to biological growth and differentiation processes. Stimulation of rac/cdc42 leads to an increase in activation of JNK and p38, responses that are associated with stress, apoptosis, and inflammation. Although growth factor responses are primarily via the ERK pathway, affecting these latter processes may lead to alternative mechanisms of neuronal survival which may mimic growth factor enhancing survival properties (Xia et al., Science, 1995, 270, 1326). The compounds may also function as survival promoting agents for neuronal and non-neuronal cells by mechanisms related to, but also distinct from, growth factor mediated survival, for example, inhibition of the JNK and p38 MAPK pathways which may lead to survival by inhibition of apoptotic cell death processes.

The present compounds are useful in the treatment of disorders associated with decreased ChAT activity or the death, injury to spinal cord motoneurons, and also have utility in, for example, diseases associated with apoptotic cell death of the central and peripheral nervous system, immune system and in inflammatory diseases.

The cyclic substituted fused pyrrolocarbazole and isoindolone compounds described herein may also find utility in the treatment of disease states involving malignant cell proliferation, such as many cancers.

By way of further illustration, compounds may be used in the development of assays and models for further enhancement of the understanding of the roles that inhibition play in the mechanistic aspects of the associated disorders and diseases. Thus, the compounds of the present invention are useful as diagnostic reagents in diagnostic assays such as the assays described herein.

The pharmaceutically acceptable salts of Compounds (I) include pharmaceutically acceptable acid addition salts, metal salts, ammonium salts, organic amine addition salts, and amino acid addition salts. Examples of the acid addition salts are inorganic acid addition salts such as hydrochloride, sulfate and phosphate, and organic acid addition salts such as acetate, maleate, fumarate, tartrate, citrate and lactate; examples of the metal salts are alkali metal salts such as lithium salt, sodium salt and potassium salt, alkaline earth metal salts such as magnesium salt and calcium salt, aluminum salt, and zinc salt; examples of the ammonium salts are ammonium salt and tetramethylammonium salt; examples of the organic amine addition salts are salts with morpholine and piperidine; and examples of the amino acid addition salts are salts with glycine, phenylalanine, glutamic acid and lysine.

Compounds provided herein can be formulated into pharmaceutical compositions by admixture with pharmaceutically acceptable nontoxic excipients and carriers. Such compositions can be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

The composition can be conveniently administered in unit dosage form and may be prepared by any of the methods well known in the pharmaceutical art, for example, as described in Remington's Pharmaceutical Sciences (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The compounds of this invention can be employed as the sole active agent in a pharmaceutical composition. Alternatively, they can be used in combination with other active ingredients, e.g., other growth factors which facilitate neuronal survival or axonal regeneration in diseases or disorders.

Compounds of Formula I and pharmaceutically acceptable salts thereof can be administered orally or non-orally, e.g., as an ointment or an injection. The concentrations of the compounds of this invention in a therapeutic composition can vary. The concentration will depend upon factors such as the total dosage of the drug to be administered, the chemical characteristics (e.g., hydrophobicity) of the compounds employed, the route of administration, the age, body weight and symptoms of a patient, etc.. The compounds of this invention typically are provided in an aqueous physiological buffer solution containing about 0.1 to 10% w/v compound for parenteral administration. Typical dose ranges are from about 1 mg to about 1 μμg/kg of body weight per day; a preferred dose range is from about 0.01 mg/kg to 100 mg/kg of body weight per day, and preferably about 0.1 to 20 mg/kg once to four times per day. A preferred dosage of drug to be administered is likely to depend on variables such as the type and extent of progression of the disease or disorder, the overall health status of the particular patient, the relative biological efficacy of the compound selected, and formulation of the compound excipient, and its route of administration.

Compounds of Formula I and pharmaceutically acceptable salts thereof can be administered alone, or in the form of various pharmaceutical compositions, according to the pharmacological activity and the purpose of administration. The pharmaceutical compositions in accordance with the present invention can be prepared by uniformly mixing an effective amount of a compound of Formula I or a pharmaceutically acceptable salt thereof, as an active ingredient, with a pharmaceutically acceptable carrier. The carrier may take a wide range of forms according to the forms of composition suitable for administration. It is desired that such pharmaceutical compositions are prepared in a unit dose form suitable for oral or non-oral administration. The forms for non-oral administration include ointment and injection.

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains 15–300 mg of the active ingredient.

Granules can be prepared using excipients such as lactose and sucrose, disintegrating agents such as starch, binders such as gelatin, and the like in a conventional manner. Powders can be prepared using excipients such as lactose and mannitol, and the like in a conventional manner. Capsules can be prepared using gelatin, water, sucrose, gum arabic, sorbitol, glycerin, crystalline cellulose, magnesium stearate, talc, and the like in a conventional manner. It is preferred that each capsule contains 15–300 mg of the active ingredient.

Syrup preparations can be prepared using sugars such as sucrose, water, ethanol, and the like in a conventional manner.

Ointment can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injectable preparations can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic ester and chlorobutanol, antioxidants such as ascorbic acid and sodium pyrosulfite, and the like in a conventional manner.

The invention is further illustrated by way of the following examples which are intended to elucidate the invention. These examples are not intended, nor are they to be construed, as limiting the scope of the disclosure.

EXAMPLES

Example 1

Inhibition of trkA Tyrosine Kinase Activity

Selected cyclic substituted fused pyrrolocarbazole and isoindolone compounds were tested for their ability to inhibit the kinase activity of baculovirus-expressed human trkA cytoplasmic domain using an ELISA-based assay as previously described (Angeles et al., Anal. Biochem. 236: 49–55, 1996). Briefly, the 96-well microtiter plate was coated with substrate solution (recombinant human phospholipase C-γ1/glutathione S-transferase fusion protein (Rotin et al., EMBO J., 11: 559–567, 1992). Inhibition studies were performed in 100 μl assay mixtures containing 50 mM Hepes, pH 7.4, 40 μM ATP, 10 mM $MnCl_2$, 0.1% BSA, 2% DMSO, and various concentrations of inhibitor. The reaction was initiated by addition of trkA kinase and allowed to proceed for 15 minutes at 37° C. An antibody to phosphotyrosine (UBI) was then added, followed by a secondary enzyme-conjugated antibody, alkaline phosphatase-labelled goat antII-mouse IgG (Bio-Rad). The activity of the bound enzyme was measured via an amplified detection system (Gibco-BRL). Inhibition data were analyzed using the sigmoidal dose-response (variable slope) equation in GraphPad Prism. The concentration that resulted in 50% inhibition of kinase activity is referred to as "$IC_{50}$". Results are summarized in Table 1.

TABLE 1

Inhibitory Effects of Cyclic Substituted Fused Pyrrolocarbazoles and Isoindolones on trkA Kinase Activity

| Cmpd. No. | IC$_{50}$ nM (% Inh. @ 300 nM) |
|---|---|
| II-01a | 92 |
| II-01c | 163 |
| II-02 | 64 |
| II-03 | 72 |
| II-04 | 8 |
| II-05 | 130 |
| II-06 | 90 |
| II-07 | 19 |
| II-09 | 134 |
| II-10 | 182 |
| II-11 | 139 |
| II-12 | 241 |
| II-13 | 186 |
| II-14 | (32) |
| II-15 | (26) |
| II-16 | (38) |
| II-17 | (33) |
| II-18 | (45) |
| II-19 | 162 |
| II-20 | (39) |
| II-21 | 15 |
| II-22 | 95 |
| II-23 | 19 |
| II-24 | (34) |
| II-25 | (27) |
| II-26 | 45 |
| II-27 | 166 |
| II-28 | 138 |
| II-29 | 16 |
| II-30a | 214 |
| II-30b | (32) |
| II-31 | 173 |
| II-33 | 153 |
| II-34 | (38) |
| II-35 | 78 |
| II-36 | 20 |
| II-37 | 191 |
| II-38 | 405 |
| II-40a | 54 |
| II-40b | 59 |
| II-42 | 149 |
| II-43 | 110 |
| II-44 | 80 |
| II-45a | (27) |
| II-45b | (19) |
| II-47 | 44 |
| II-48 | (46) |
| II-49 | 321 |
| II-50 | 113 |
| II-51a | (56) |
| II-51bc | (56) |
| II-51d | (58) |
| II-52 | 27 |
| II-53 | 8 |
| II-54 | 59 |
| II-55a | (09) |
| II-55b | 315 |
| II-56 | (12) |
| II-59 | (10) |
| II-58 | (23) |
| II-62 | (27) |
| II-63 | (28) |
| II-64 | 399 |
| II-65 | 320 |
| II-66 | (53) |
| II-67 | 555 |
| II-68 | 245 |
| II-69 | 24 |

Example 2

Inhibition of NGF-stimulated trk Phosphorylation in a Whole Cell Preparation

The inhibition of NGF-stimulated phosphorylation of trk by selected cyclic substituted fused pyrrolocarbazole and isoindolone compounds was performed using a modified procedure, as described below, from that previously described (see U.S. Pat. No. 5,516,771). NIH3T3 cells transfected with trkA were grown in 100 mm dishes. Subconfluent cells were serum-starved by replacing media with serum-free 0.05% BSA-DMEM containing compound (100 nM and 1 μM) or DMSO (added to controls) for one hour at 37° C. NGF (Harlan/Bioproducts for Science) was then added to the cells at a concentration of 10 ng/ml for 5 minutes. Cells were lysed in buffer containing detergent and protease inhibitors. Clarified cell lysates were normalized to protein using BCA method and immunoprecipitated with antII-trk antibody. Polyclonal antII-trk antibody was prepared against a peptide corresponding to the 14 amino acids at the carboxy terminus of trk (Martin-Zanca et al., Mol. Cell. Biol. 9: 24–33, 1989). The immune complexes were collected on Protein A Sepharose beads (Sigma Chem. Co., St. Lois, Mo.), separated by SDS polyacrylamide gel electrophoresis (SDS-PAGE), and transferred to a polyvinylidene difluoride (PVDF) membrane. The membrane was immunoblotted with antII-phosphotyrosine antibody (UBI), followed by incubation with horseradish peroxidase coupled goat antII-mouse IgG (Bio-Rad Laboratories, Hercules, Calif.). Phosphorylated proteins were visualized using ECL (Amersham Life Science, Inc., Arlington Heights, Ill.). The area of the trk protein band was measured and compared to NGF-stimulated control. The inhibition scoring system used, based on percent decrease in trk protein band, was as follows: 0=no decrease; 1=1–25%; 2=26–49%; 3=50–75%; 4=76–100%. Results are shown below in Table 2.

TABLE 2

Effects of Cyclic Substituted Fused Pyrrolocarbazoles and Isoindolones on NGF-stimulated trkA Phosphorylation in NIH3T3 Cells

| Cmpd. No. | Cell Score @ 100 nM | 1 uM |
|---|---|---|
| II-04 | 1 | 2 |
| II-06 | 1 | 2 |
| II-07 | 1 | 2 |
| II-21 | 2 | 4 |
| II-23 | 2 | 4 |
| II-26 | 2 | 4 |
| II-29 | 0 | 4 |
| II-35 | 0 | 3 |
| II-36 | 1 | 4 |
| II-38 | 2 | 2 |
| II-47 | 1 | 3 |
| II-52 | 2 | 3 |
| II-53 | 4 | 4 |
| II-54 | 2 | 4 |

Example 3

Inhibition of Vascular Endothelial Growth Factor Receptor Kinase Activity

Cyclic substituted fused pyrrolocarbazole and isoindolone compounds were examined for their inhibitory effects on the kinase activity of baculovirus-expressed VEGF receptor (human flk-1, KDR, VEGFR2) kinase domain using the procedure described for the trkA kinase ELISA assay described above. The kinase reaction mixture, consisting of 50 mM Hepes, pH 7.4, 40 µM ATP, 10 mM MnCl$_2$, 0.1% BSA, 2% DMSO, and various concentrations of inhibitor, was transferred to PLC-γ/GST-coated plates. VEGFR kinase was added and the reaction was allowed to proceed for 15 min. at 37 C. Detection of phosphorylated product was accomplished by addition of antII-phosphotyrosine antibody (UBI). A secondary enzyme-conjugated antibody was delivered to capture the antibody-phosphorylated PLC-γ/GST complex. The activity of the bound enzyme was measured via an amplified detection system (Gibco-BRL). Inhibition data were analyzed using the sigmoidal dose-response (variable slope) equation in GraphPad Prism. Results are summarized in Table 3.

TABLE 3

Inhibitory Effects of Cyclic Substituted Fused Pyrrolocarbazoles and Isoindolones on VEGF Receptor Kinase Activity

| Cmpd. No. | IC$_{50}$ nM (% Inh. @ 300 nM) |
|---|---|
| II-01b | 266 |
| II-01c | 168 |
| II-06 | (56) |
| II-17 | (33) |
| II-19 | (46) |
| II-23 | 79 |
| II-26 | (48) |
| II-30a | (59) |
| II-34 | (52) |
| II-35 | (55) |
| II-36 | 846 |
| II-38 | 5103 |
| II-40b | 1419 |
| II-42 | 1386 |
| II-44 | >1000 |
| II-45b | >1000 |
| II-46 | 8072 |
| II-51a | 170 |
| II-51bc | (62) |
| II-51d | (48) |
| II-53 | 209 |
| II-54 | 122 |
| II-55a | (30) |
| II-55b | 1884 |
| II-57 | 380 |
| II-60 | (45) |
| II-64 | (20) |
| II-65 | (26) |
| II-66 | (56) |
| II-67 | (65) |
| II-68 | (31) |
| II-69 | (49) |

Example 4

Inhibition of Protein Kinase C Activity

Protein kinase C activity was assessed using the Millipore Multiscreen TCA "in-plate" assay as described in Pitt, A. M. and Lee, C. (J. Biomol. Screening, 1: 47–51, 1996). Assays were performed in 96-well Multiscreen-DP plates (Millipore). Each 40-ml assay mixture contained 20 mM Hepes, pH 7.4, 10 mM MgCl$_2$, 2.5 mM EGTA, 2.5 mM CaCl$_2$, 80 mg/ml phosphatidyl serine, 3.2 mg/ml diolein, 200 mg/ml histone H-1 (Fluka), 5 mM [γ-$^{32}$P]ATP, 1.5 ng protein kinase C (UBI; mixed isozymes of a, b, g), 0.1% BSA, 2% DMSO, and test cyclic substituted fused pyrrolocarbazole compound. The reaction was allowed to proceed for 10 min at 37° C., then quenched by adding ice cold 50% trichloroacetic acid. The plates were allowed to equilibrate for 30 min at 4° C., then washed with ice cold 25% TCA. Scintillation cocktail was added to the plates, and the radioactivity was determined using Wallac MicroBeta 1450 PLUS scintillation counter. The IC$_{50}$ values were calculated by fitting the data to the sigmoidal dose-response (variable slope) equation in GraphPad Prism. The results are summarized in Table 4.

TABLE 4

Inhibitory Effects of Cyclic Substituted Fused Pyrrolocarbazoles and Isoindolones On Protein Kinase C Activity

| II-02 | 7500 |
|---|---|
| II-03 | 4071 |
| II-04 | >10,000 |
| II-07 | 7116 |
| II-10 | 1574 |
| II-14 | >10,000 |
| II-15 | >10,000 |
| II-21 | >10,000 |
| II-23 | 644 |
| II-26 | 2070 |
| II-29 | 2077 |
| II-33 | 1039 |
| II-35 | >10,000 |
| II-36 | >10,000 |
| II-38 | >10,000 |
| II-42 | 6229 |
| II-47 | 1534 |
| II-53 | 2205 |
| II-61 | 1359 |
| II-62 | (27) |
| II-63 | (28) |
| II-64 | 1230 |
| II-65 | (20) |
| II-66 | (31) |
| II-67 | 540 |

Example 5

Inhibition of Platelet Derived Growth Factor Receptor Kinase Activity

Cyclic substituted fused pyrrolocarbazole and isoindolone compounds were examined for their inhibitory effects on the kinase activity of baculovirus-expressed PDGFβ receptor kinase domain using the trkA kinase ELISA described above. Assays were performed in substrate (PLC-γ/GST)-coated 96-well microtiter plates. Each 100-µl reaction mixture contained 50 mM HEPES, pH 7.4, 20 µM ATP, 10 mM MnCl$_2$, 0.1% BSA, 2% DMSO, and various concentrations of inhibitor. The reaction was initiated by addition of pre-phosphorylated recombinant human enzyme (10 ng/ml PDGFRβ) and allowed to proceed for 15 minutes at 37° C. The prephosphorylated enzyme was prepared prior to use by incubation of the kinase in buffer containing 20 µM ATP and 10 mM MnCl$_2$ for 1 hour at 4° C. Detection of phosphorylated product was done by adding horseradish peroxidase (HRP)-conjugated antII-phosphotyrosine antibody (UBI). The HRP substrate solution containing 3, 3'-5, 5'-tetramethylbenzidine and hydrogen peroxide was later added and the plates were incubated for 10 minutes at room temperature. The reaction was quenched with acid and the resulting absorbance was read at 450 nm using a Microplate Biokinetics Reader (Bio-Tek Instrument EL 312e). Inhibition data were analyzed using the sigmoidal dose-response (variable slope) equation in GraphPad Prism. The results are summarized in Table 5.

TABLE 5

PDGFRβ Inhibitory Effects of Cyclic Substituted Fused Pyrrolocarbazoles and Isoindolones

| Cmpd. No. | $IC_{50}$ nM (% inh @ 300 nM) |
|---|---|
| II-17 | (47) |
| II-23 | 648 |
| II-52 | (45) |
| II-64 | (29) |
| II-65 | (05) |
| II-66 | (21) |
| II-67 | (23) |
| II-68 | (0) |
| II-69 | (18) |

Example 6

Enhancement of Spinal Cord ChAT Activity

As discussed above, ChAT is a specific biochemical marker for functional cholinergic neurons. Cholinergic neurons represent a major cholinergic input into the hippocampal formation, olfactory nucleus, interpeduncular nucleus, cortex, amygdala, and parts of the thalamus. In the spinal cord, the motor neurons are cholinergic neurons which contain ChAT (Phelps et al., J. Comp. Neurol. 273:459–472 (1988)). ChAT activity has been used to study the effects of neurotrophins (e.g., NGF or NT-3) on the survival and/or function of cholinergic neurons. The ChAT assay also serves as an indication of the regulation of ChAT levels within cholinergic neurons.

Cyclic substituted fused pyrrolocarbazole and isoindolone compounds increased ChAT activity in the dissociated rat embryonic spinal cord culture assay (Table 6). For example, in these assays, a compound was directly added to a dissociated spinal cord culture. Compounds which increased ChAT activity at least 120% of the control activity were considered active. Results are summarized in Table 6.

TABLE 6

Enhancement of Spinal Cord ChAT Activity by Cyclic Substituted Fused Pyrrolocarbazoles and Isoindolones

| Compound | Spinal Cord ChAT (% control) | |
|---|---|---|
| | Activity at 30 nM | Maximal Activity |
| II-20 | 132 | 191 @ 500 nM |

Methods: Fetal rat spinal cord cells were dissociated, and experiments were performed as described (Smith et al., J. Cell Biology 101:1608–1621 (1985); Glicksman et al., J. Neurochem. 61:210–221 (1993)). Dissociated cells were prepared from spinal cords dissected from rats (embryonic day 14–15) by standard trypsin dissociation techniques (Smith et al., supra.). Cells were plated at 6×105 cells/cm² on poly-1-ornithine coated plastic tissue culture wells in serum-free N2 medium supplemented with 0.05% bovine serum albumin (BSA) (Bottenstein et al., PNAS USA 76:514–517 (1979)). Cultures were incubated at 37° C. in a humidified atmosphere of 5% $CO_2$/95% air for 48 hours. ChAT activity was measured after 2 days in vitro using a modification of the Fonnum procedure (Fonnum, J. Neurochem. 24:407–409 (1975)) according to McManaman et al. and Glicksman et al. (McManaman et al., Developmental Biology 125:311–320 (1988); Glicksman et al., J. Neurochem., supra.).

Compounds of Formula II described in the examples are listed in Tables 7 and 8. In Table 7, values for R1, R4, and R6 are H; Q is NH (except for compounds II-68 and II-69, where Q is NC(=O)NHEt) and G is a bond. In Table 8, R1, R4, R5, R6, and R8 are H; W is $CH_2$, m is equal to 0 and G is $CH_2$.

Compounds II-64 to II-67 are described in Table 9. In Table 9, R1, R3, R4, R5, and R6 are H; A1,A2 is H, H; and B1,B2 is O.

TABLE 7

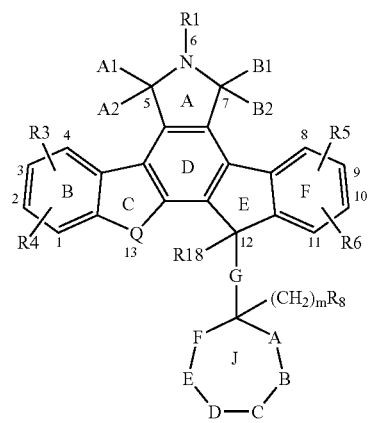

| Compound No. | A1A2 | B1B2 | R3 | R5 | R18 | m | R8 | A |
|---|---|---|---|---|---|---|---|---|
| II-02 | H2 | O | H | H | H | 0 | OH | CH2 |
| II-03 | H2 | O | H | H | H | 0 | OH | CH2 |
| II-04 | H2 | O | H | H | H | 1 | H | O |
| II-05 | H2 | O | H | H | H | 0 | H | O |
| II-06 | H2 | O | H | H | H | 0 | H | O |
| II-07 | H2 | O | H | H | H | 0 | H | O |

TABLE 7-continued

| | | | | | | | | | |
|---|---|---|---|---|---|---|---|---|---|
| II-08 | H2 | O | H | H | H | 0 | (p)-F-phenyl | O | |
| II-09 | H2 | O | H | H | H | 0 | 2-thienyl | O | |
| II-10 | H2 | O | H | H | H | 0 | OH | CH2 | |
| II-11 | H2 | O | H | H | H | 0 | H | CH2 | |
| II-12 | H2 | O | H | H | H | 1 | H | O | |
| II-13 | H2 | O | H | H | H | 0 | H | O | |
| II-14 | H2 | O | H | H | H | 0 | OH | CH2 | |
| II-15 | H2 | O | H | H | H | 0 | OH | CH2 | |
| II-16 | H2 | O | H | H | H | 0 | OH | CH2 | |
| II-17 | H2 | O | H | H | H | 0 | OH | CH[CH2-N((CH2)2)2O] | |
| II-18 | H2 | O | H | H | H | 0 | OH | CH2 | |
| II-19 | H2 | O | H | H | H | 3 | Cl | O | |
| II-20 | H2 | O | H | H | H | 1 | O(C=O)—t-Bu | O | |
| II-21 | H2 | O | H | H | H | 1 | OH | O | |
| II-22 | H2 | O | H | H | H | 1 | O(C=O)CH3 | O | |
| II-23 | H2 | O | H | H | H | 0 | H | O | |
| II-24 | H2 | O | H | H | H | 0 | OH | CH2 | |
| II-25 | H2 | O | H | H | H | 1 | H | O | |
| II-26 | H2 | O | H | H | H | 1 | H | O | |
| II-27 | H2 | O | H | H | H | 1 | H | O | |
| II-28 | H2 | O | H | H | H | 0 | —CH=CH2-CH(OH)CH2- | O | |
| II-29 | H2 | O | H | H | H | 0 | OH | O | |
| II-30a | H2 | O | H | H | H | 1 | H | O | |
| II-30b | H2 | O | H | H | H | 1 | H | O | |
| II-31 | H2 | O | H | H | H | 1 | —OCH2OCH2-CH2OCH3 | O | |
| II-32 | H2 | O | H | H | Et | 1 | t-Bu | O | |
| II-33 | H2 | O | H | H | H | 1 | OH | O | |
| II-34 | H2 | O | H | H | Et | 1 | OH | O | |
| II-35 | H2 | O | H | H | H | 1 | OH | O | |
| II-36 | H2 | O | H | H | H | 1 | OH | O | |
| II-37 | O | H2 | H | H | H | 1 | H | O | |
| II-38 | H2 | O | H | H | H | 0 | H | O | |
| II-40a | H2 | O | H | H | H | 0 | H | O | |
| II-40b | H2 | O | H | H | H | 0 | H | O | |
| II-42 | H2 | O | H | H | H | 0 | OH | O | |
| II-43 | H2 | O | H | H | H | 0 | H | O | |
| II-44 | H2 | O | H | H | H | 1 | Cl | O | |
| II-45a | H2 | O | H | H | H | 0 | H | O | |
| II-45b | H2 | O | H | H | H | 0 | H | O | |
| II-46 | H2 | O | H | H | Et | 0 | H | O | |
| II-47 | H2 | O | H | H | H | 0 | OH | C(=O) | |
| II-48 | H2 | O | H | H | H | 0 | OH | O | |
| II-49 | H2 | O | H | H | H | 0 | | —C=N— | |
| II-50 | H2 | O | H | H | H | 0 | OH | CH2 | |
| II-51a | H2 | O | H | H | H | 1 | H | O | |
| II-51bc | H2 | O | H | H | H | 1 | H | O | |
| II-51d | H2 | O | H | H | H | 1 | H | O | |
| II-52 | H2 | O | 3-C(=O)O—CH2CH2-OCH3 | H | H | 0 | H | O | |
| II-53 | H2 | O | H | 10-O—Me | H | 1 | OH | O | |
| II-54 | H2 | O | H | 10-O—Me | H | 1 | OH | O | |
| II-55 | H2 | O | H | H | H | 0 | H | CH(COOEt) | |
| II-56 | O | O | H | H | H | 0 | H | CH(COOEt) | |
| II-59 | H2 | O | H | H | H | 0 | H | CH2 | |
| II-60 | H2 | O | H | H | H | 0 | H | C(=O) | |
| II-68 | H2 | O | H | H | H | 1 | OC(=O)NHEt | O | |
| II-69 | H2 | O | H | H | H | 1 | OH | O | |

| Compound No. | B | C | D | E | F | Comments |
|---|---|---|---|---|---|---|
| II-02 | CH2 | N(Bn) | bond | CH2 | CH2 | |
| II-03 | CH2 | O | bond | CH2 | CH2 | |
| II-04 | CH2 | CH2 | CH2 | bond | bond | mixture of diastereomers |
| II-05 | C(=O) | CH2 | CH2 | CH2 | bond | mixture of diastereomers |
| II-06 | C(=O) | CH2 | CH2 | bond | bond | mixture of diastereomers |
| II-07 | CH2 | CH2 | CH2 | CH2 | bond | mixture of diastereomers |
| II-08 | CH2 | CH2 | CH2 | bond | bond | mixture of diastereomers |
| II-09 | CH2 | CH2 | CH2 | bond | bond | |
| II-10 | CH2 | N(Me) | bond | CH2 | CH2 | |
| II-11 | S | CH2 | CH(OH) | bond | bond | mixture of diastereomers |
| II-12 | CH2 | CH2 | CH2 | CH2 | bond | mixture of diastereomers |
| II-13 | CH2 | CH2 | CH2 | CH2 | bond | mixture of diastereomers |

TABLE 7-continued

| | | | | | | |
|---|---|---|---|---|---|---|
| II-14 | CH2 | S | bond | CH2 | CH2 | diastereomers |
| II-15 | 1,6-benzo-fused | | bond | CH2 | CH2 | mixture of diastereomers |
| II-16 | N(Et) | CH2 | bond | CH2 | CH2 | mixture of diastereomers |
| II-17 | CH2 | bond | bond | CH2 | CH2 | mixture of diastereomers |
| II-18 | CH2 | CH2 | bond | bond | bond | |
| II-19 | CH2 | CH2 | CH2 | bond | bond | mixture of diastereomers |
| II-20 | CH2 | CH2 | CH2 | bond | bond | mixture of diastereomers |
| II-21 | CH2 | CH2 | CH2 | bond | bond | mixture of diastereomers |
| II-22 | CH2 | CH2 | CH2 | bond | bond | mixture of diastereomers |
| II-23 | CH(OH) | CH2 | CH2 | bond | bond | mixture of diastereomers |
| II-24 | CH2 | N[(C=O)CH3] | bond | CH2 | CH2 | |
| II-25 | CH2 | —C(=CH2)— | CH2 | bond | bond | mixture of diastereomers |
| II-26 | CH2 | —C[(OH)(CH2OH)]— | CH2 | bond | bond | mixture of diastereomers |
| II-27 | CH2 | —C(=O)— | CH2 | bond | bond | mixture of diastereomers |
| II-28 | CH2 | CH2 | CH2 | bond | bond | mixture of diastereomers |
| II-29 | CH2 | CH2 | CH2 | bond | bond | mixture of diastereomers |
| II-30a | CH2 | CH2 | CH2 | bond | bond | diastereomer A |
| II-30b | CH2 | CH2 | CH2 | bond | bond | diastereomer B |
| II-31 | —C(=O)— | CH2 | CH2 | bond | bond | mixture of doastereomers |
| II-32 | CH2 | CH2 | CH2 | bond | bond | mixture of diastereomers |
| II-33 | —C(=O)— | CH2 | CH2 | bond | bond | mixture of diastereomers |
| II-34 | CH2 | CH2 | CH2 | bond | bond | mixture of diastereomers |
| II-35 | CH2 | CH2 | CH2 | bond | bond | diastereomer A |
| II-36 | CH2 | CH2 | CH2 | bond | bond | diastereomer B |
| II-37 | CH2 | CH2 | CH2 | bond | bond | mixture of diastereomer |
| II-38 | CH(OH) | CH2 | CH2 | bond | bond | single doastereomer |
| II-40a | CH(OEt) | CH2 | CH2 | bond | bond | mixture of diastereomers AB |
| II-40b | CH(OEt) | CH2 | CH2 | bond | bond | mixture of diastereomers |
| II-42 | CH2 | CH2 | CH2 | bond | bond | |
| II-43 | CH2 | CH2 | CH(OH) | bond | bond | mixture of diastereomers |
| II-44 | CH2 | CH2 | CH2 | bond | bond | single diastereomer |
| II-45a | 1,6-[2,4-(OMe)2])-benzo-fused | | CH2 | bond | bond | diastereomer A |
| II-45b | 1,6-[2,4-(OMe)2])-benzofused | | CH2 | bond | bond | diastereomer B |
| II-46 | 1,6-[2,4-(OMe)2])-benzofused | | CH2 | bond | bond | single diastereomer |
| II-47 | O | CH2 | —C[(CH3)2]— | bond | bond | single doastereomer |
| II-48 | —CH[O(CMe2)O]CH— | | CH2 | bond | bond | mixture of diastereomers |
| II-49 | NH | C(=O) | CH2 | CH2 | bond | |
| II-50 | CH2 | CH2 | CH2 | CH2 | bond | |
| II-51a | CH(Oet) | CH2 | O | CH2 | bond | diasteremer A |
| II-51bc | CH(OEt) | CH2 | O | CH2 | bond | diastereomers B & C |
| II-51d | CH(Oet) | CH2 | O | CH2 | bond | diastereomer D |
| II-52 | CH(OOCH2—CH2OCH3) | CH2 | CH2 | bond | bond | mixture of diastereomers |
| II-53 | CH2 | CH2 | CH2 | bond | bond | single diastereomer |
| II-54 | CH(OEt) | CH2 | CH2 | bond | bond | single diastereomer |

TABLE 7-continued

| | | | | | | |
|---|---|---|---|---|---|---|
| II-55 | C(=O) | CH2 | CH2 | bond | bond | single diastereomer |
| II-56 | C(=O) | CH2 | CH2 | bond | bond | single diastereomer |
| II-59 | CH2 | CH2 | CH2 | bond | bond | single diastereomer |
| II-60 | O | CH2 | CH2 | bond | bond | single diastereomer |
| II-68 | CH2 | CH2 | CH2 | bond | bond | |
| II-69 | CH2 | CH2 | CH2 | bond | bond | diastereomer B |

TABLE 8

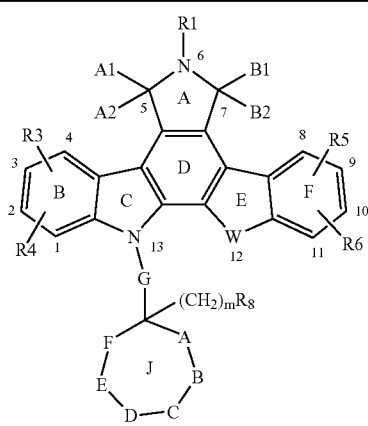

| Compound No. | A1A2 | B1B2 | R3 | A | B | C | D | E | F | Comments |
|---|---|---|---|---|---|---|---|---|---|---|
| II-01a | H2 | O | H | O | CH2 | bond | bond | bond | bond | racemate (S) |
| II-01c | H2 | O | H | O | CH2 | bond | bond | bond | bond | enantiomer (R) |
| II-01b | H2 | O | H | O | CH2 | bond | bond | bond | bond | enantiomer |
| II-39 | H2 | O | H | C(=O) | CH2 | bond | bond | bond | bond | |
| II-41 | H2 | O | H | C(OH) | CH2 | CH2 | bond | bond | bond | mixture of diastereomers |
| II-57 | H2 | O | 3-Br | O | CH2 | bond | bond | bond | bond | racemate |
| II-58 | H2 | O | 3-CH2OCH2—CH3 | O | CH2 | bond | bond | bond | bond | racemate |
| II-61 | H2 | O | 3-CH2OCH2—CH2OCH3 | O | CH2 | bond | bond | bond | bond | racemate |
| II-62 | H2 | O | H | O | CH2 | CH2 | CH2 | CH2 | bond | racemate |
| II-63 | H2 | O | H | CH2 | O | CH2 | CH2 | CH2 | bond | racemate |

TABLE 9

| Compound No. | Q | W |
|---|---|---|
| II-64 | NH | 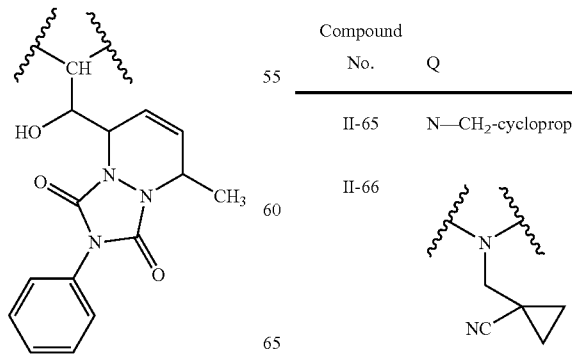 |

TABLE 9-continued

| Compound No. | Q | W |
|---|---|---|
| II-65 | N—CH$_2$-cyclopropyl | CH—CH$_2$-cyclopropyl |
| II-66 | 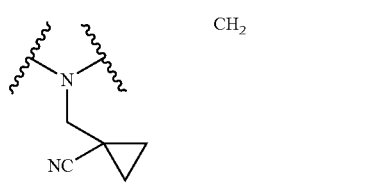 | CH$_2$ |

TABLE 9-continued

| Compound No. | Q | W |
|---|---|---|
| II-67 | 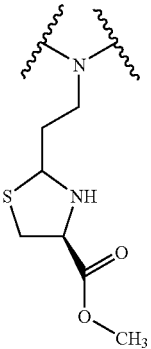 | CH₂ |

GENERAL DESCRIPTION OF THE SYNTHETIC PROCESSES AND EXAMPLES

Figure 6:
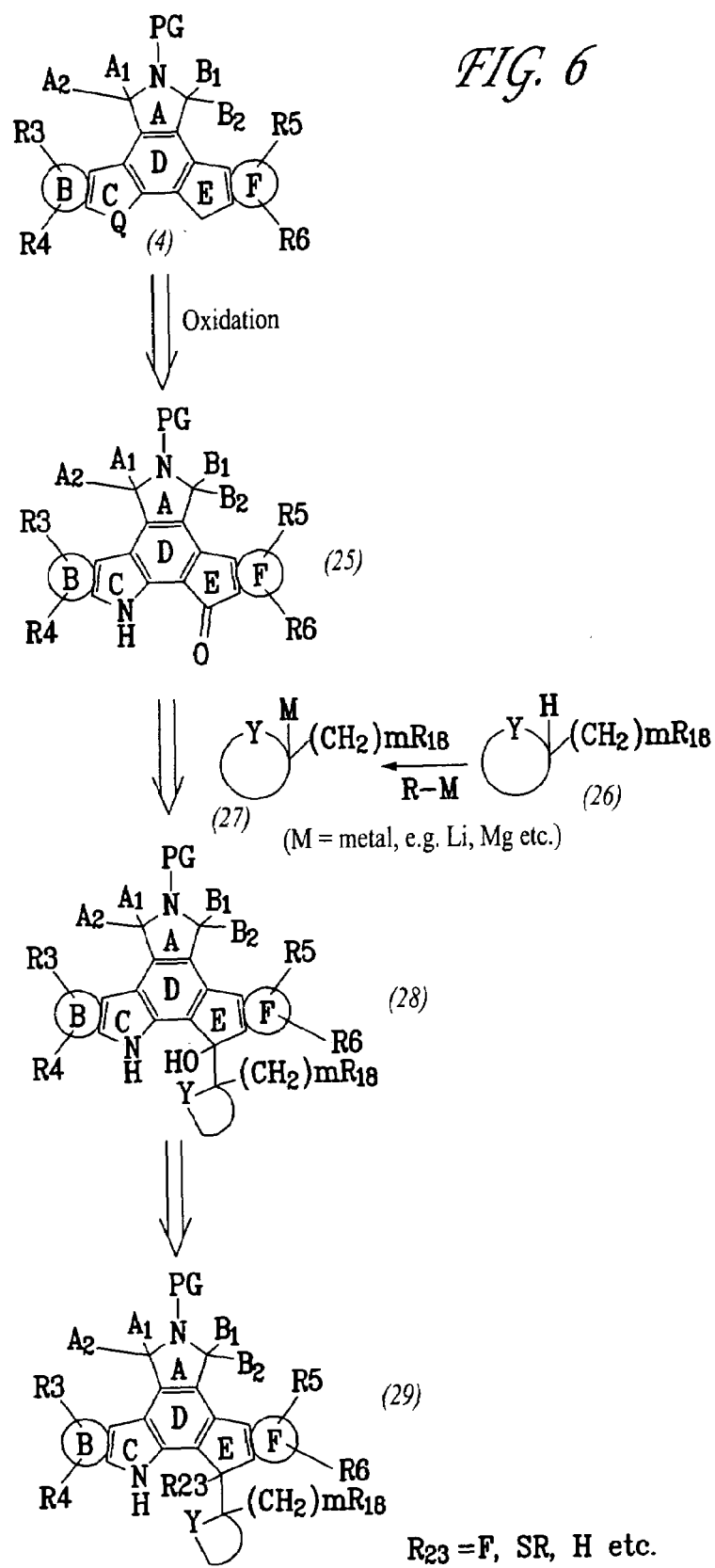
FIG. 6 is a schematic drawing showing a general preparation of a cyclic compound of the invention by the introduction of a preferred appropriately substituted cyclic intermediate as a nucleophile.
Figure 7:
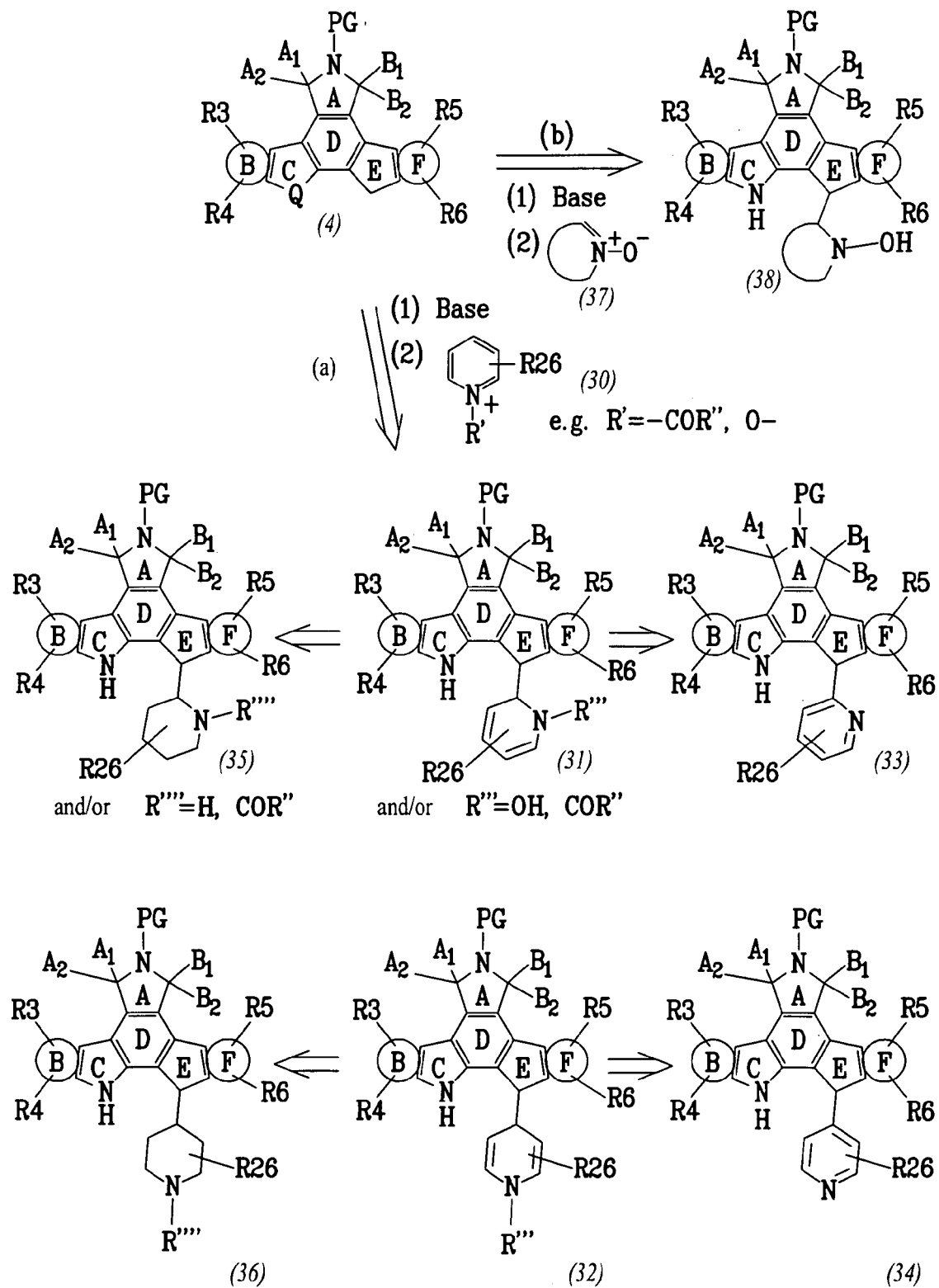
FIG. 7 is a schematic drawing showing a general preparation of a cyclic compound of the invention by reaction of a carbanion intermediate with highly electrophilic reagents.
Figure 9:
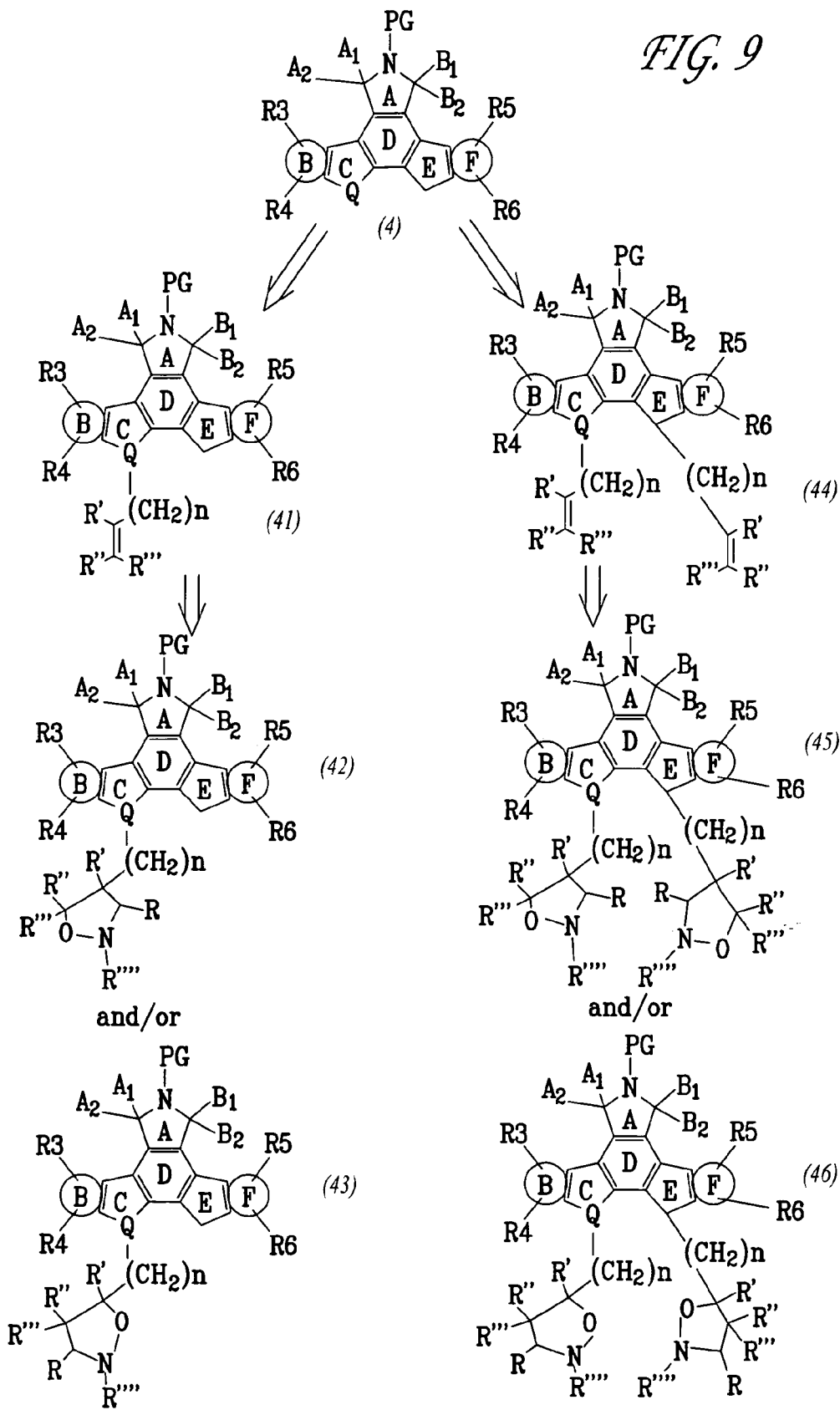
FIG. 9 is a schematic drawing showing a general preparation of a cyclic compound of the invention in which cyclic susbtituents are formed from an olefinic group.
Figure 16:
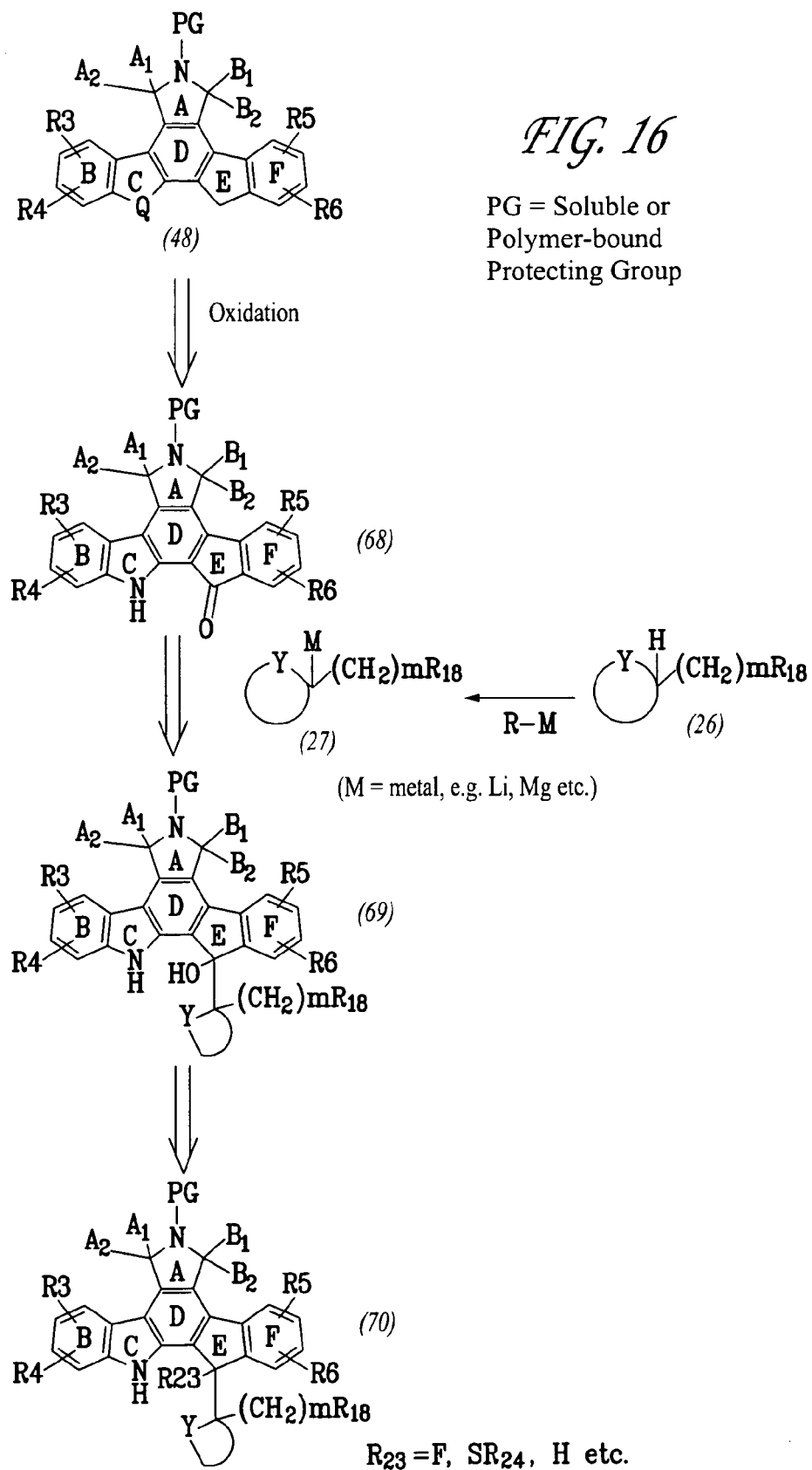
FIG. 16 is a schematic drawing showing a general preparation of a cyclic compound of the invention by the introduction of a preferred appropriately substituted cyclic intermediate as a nucleophile.
Figure 18:
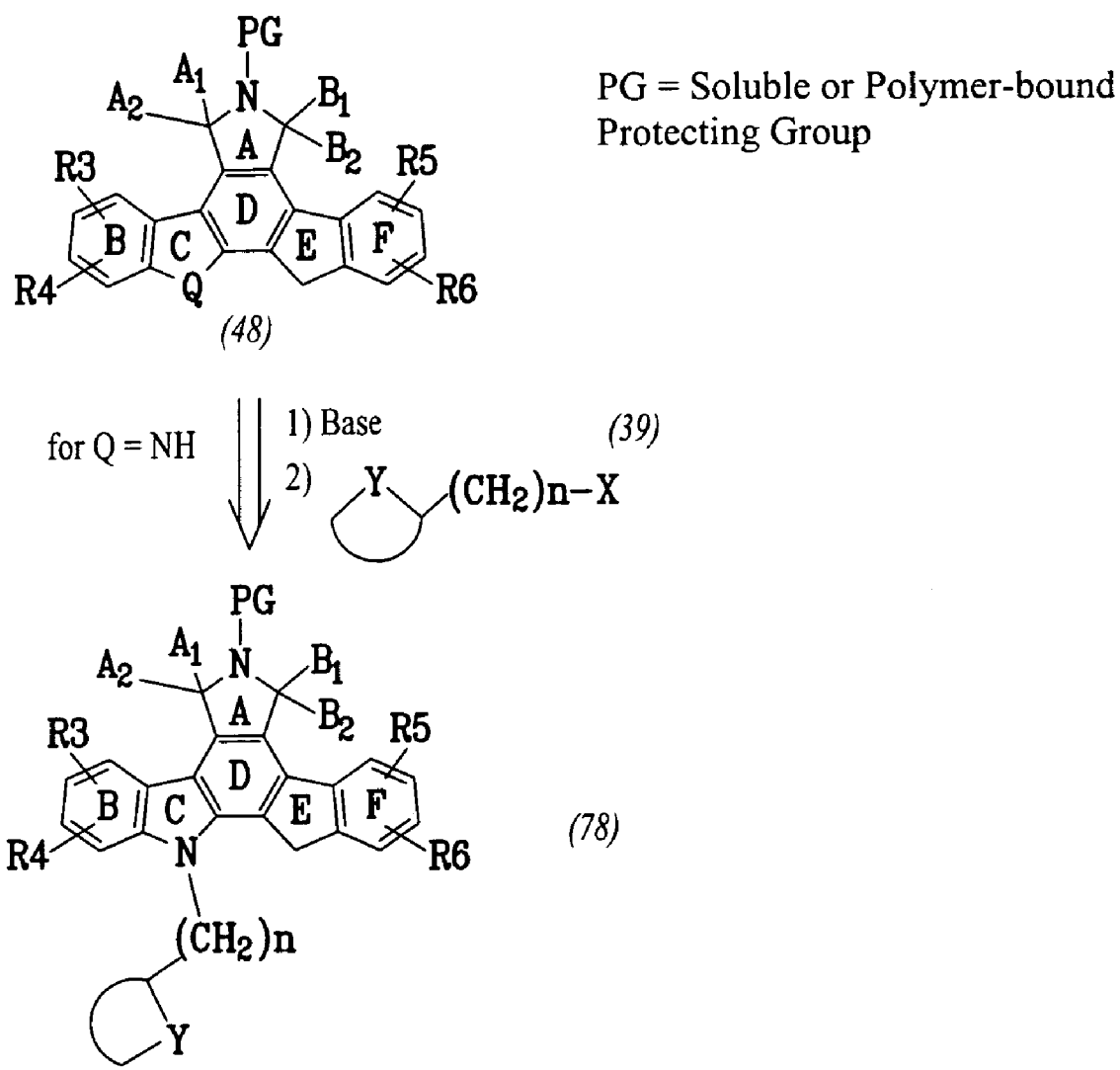
FIG. 18 is another schematic drawing showing a general preparation of a cyclic compound of the invention using a preferred appropriately substituted cyclic intermediate as an electrophile.
Figure 19:
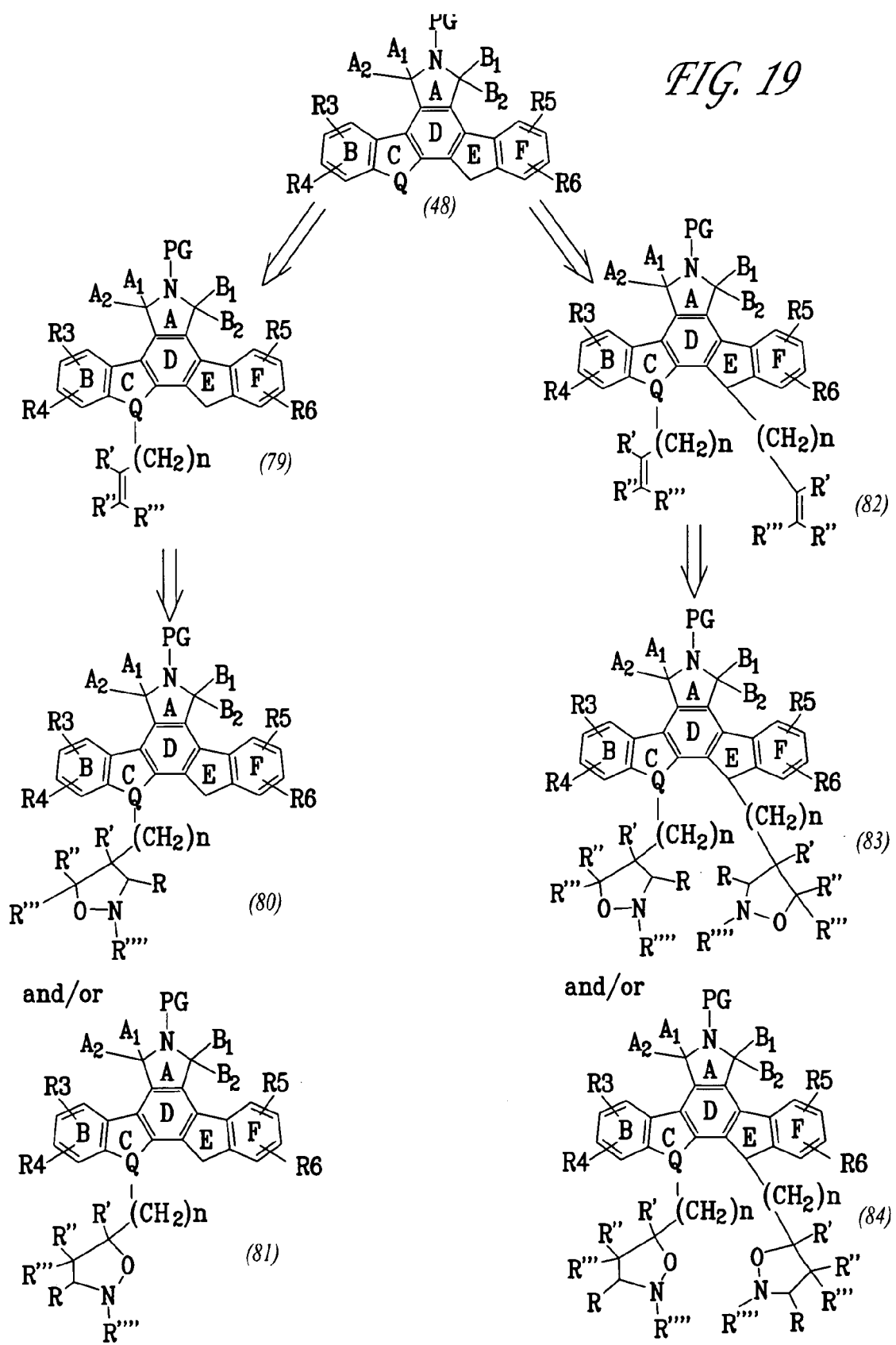
FIG. 19 is another schematic drawing showing a general preparation of a cyclic compound of the invention in which cyclic susbtituents are formed from an olefinic group.

The general synthetic route employed to prepare the cyclic substituted fused pyrrolocarbazoles of this invention is shown in FIGS. 2 through 12. The general procedures for synthesis of the fused pyrrolocarbazoles (3)/47) can be performed as described in U.S. Pat. No. 5,705,511, and U.S. Pat. No. 4,923,986, the disclosure of each of which is hereby incorporated by reference in its entirety. When R1 is H, the lactam nitrogen of the fused pyrrolocarbazoles (3)/(47) is protected with an appropriate protecting group leading to (4)/(48). The protected compounds are treated with an appropriate base in anhydrous organic solvent(s), which results in the generation of a dark red solution, which is believed to be the carbanion. Reaction of the carbanion with a reagent containing an electrophilic C═Y bond provides either a cyclic substituent directly (as shown in FIGS. 2, 5, 7, 12, 15, and 17), or an initially formed acyclic derivative (6), (14), (53) or (60), which is subsequently converted to a cyclic substituent (as shown in FIGS. 3, 4, 13 and 14). A preformed, appropriately substituted cyclic derivative may be used as either a nucleophile (as shown in FIGS. 6 and 16), or as an electrophile (as shown in FIGS. 8 and 18). Cyclic substituents may be formed from an olefinic group as shown in FIGS. 9 and 19.

Figure 10:
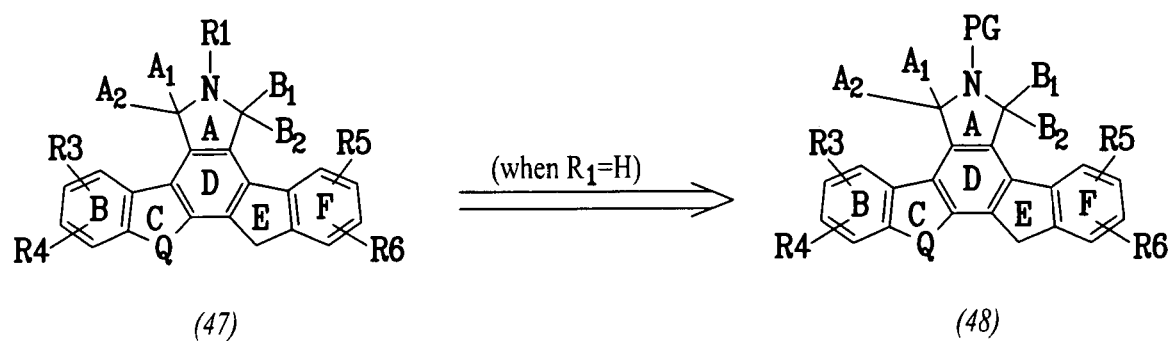
FIG. 10 is a schematic drawing showing the preparation of an $R^1$ protected fused pyrrolocarbazoles and isoindolones.
Figure 12:
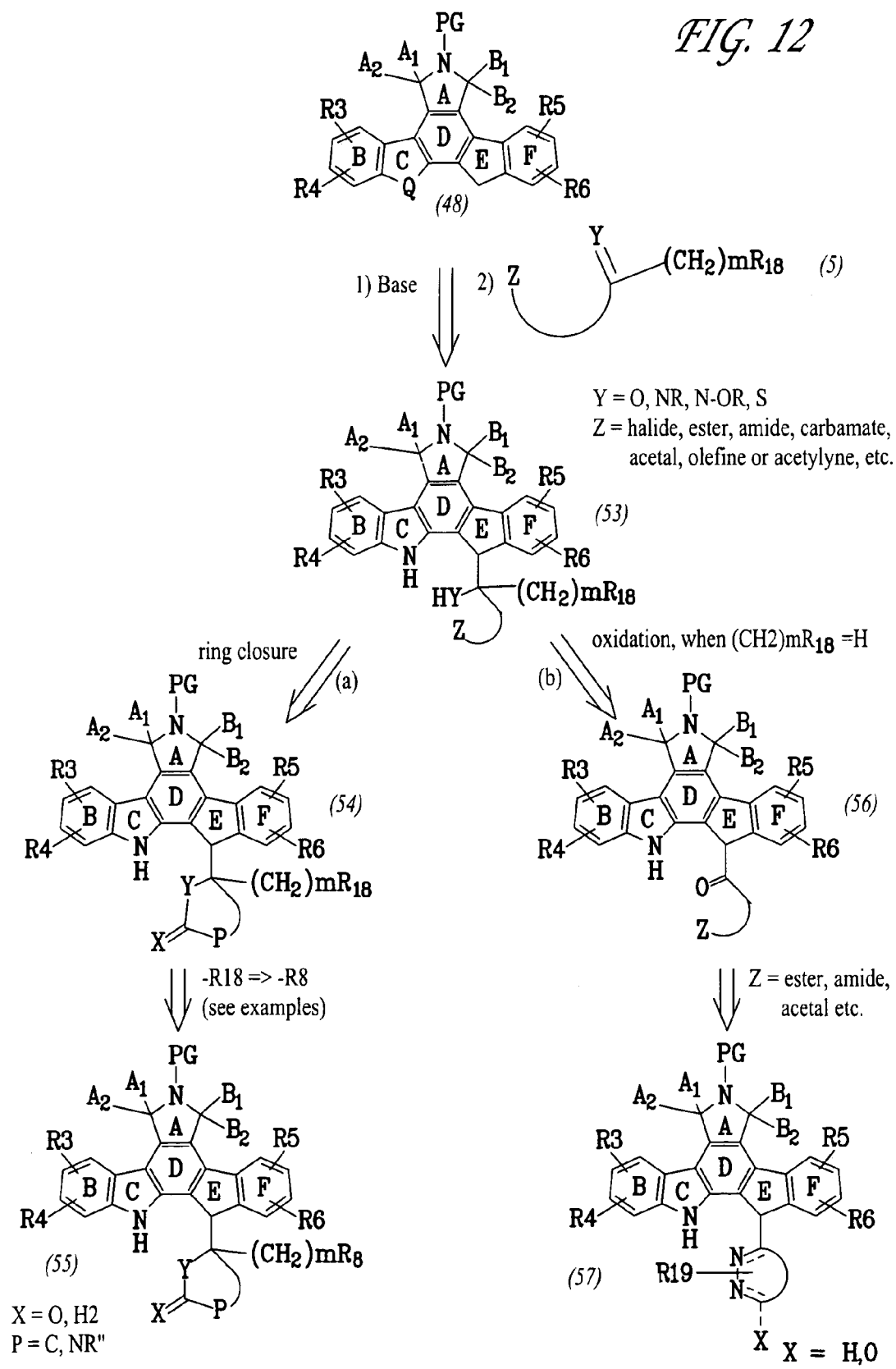
FIG. 12 is a schematic drawing showing a general preparation of a cyclic compound of the invention by reaction of a carbanion intermediate with an acyclic reagent containing an electrophilic C=Y bond to provide the cyclic substituent directly.
Figure 13:
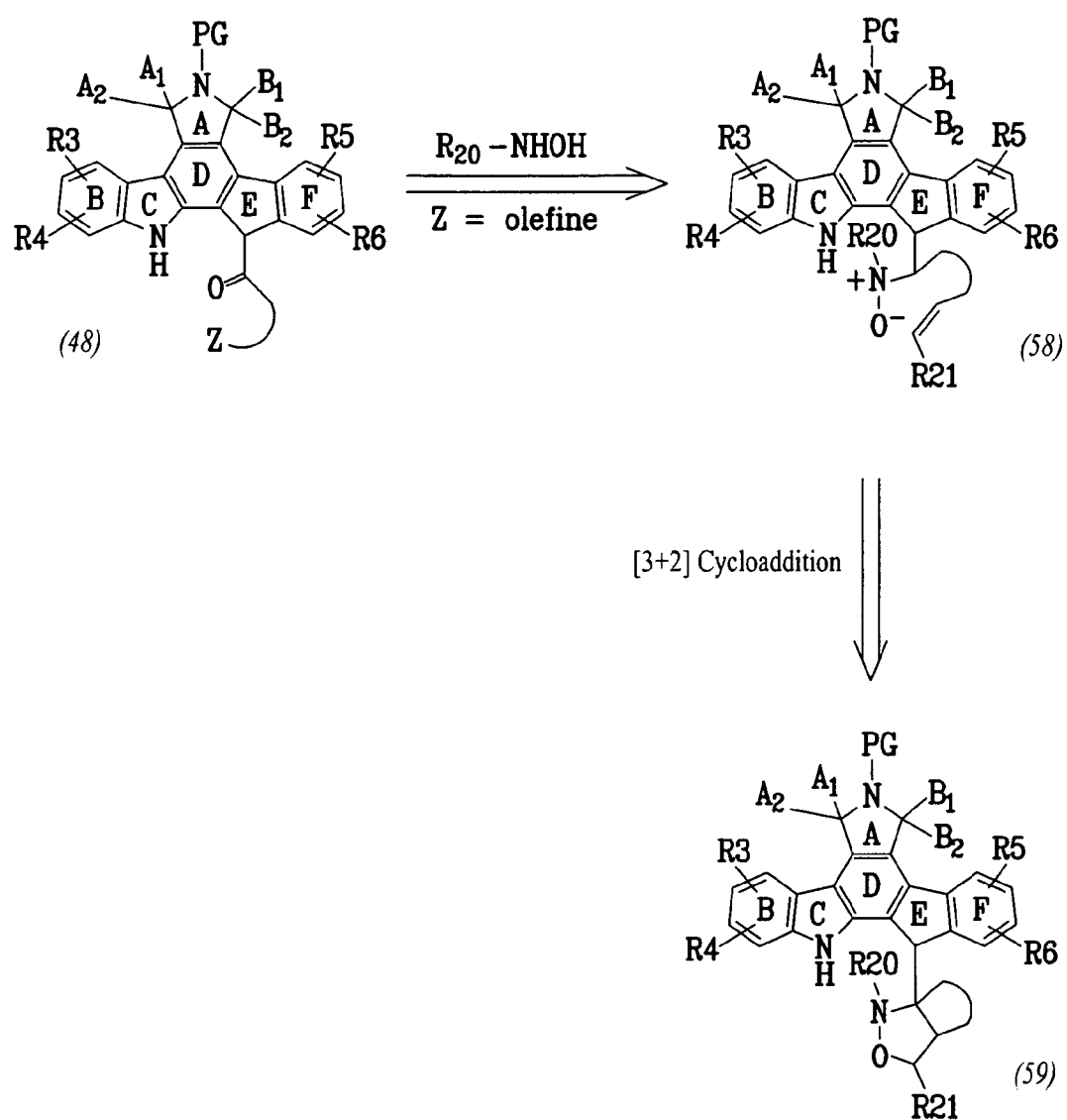
FIG. 13 is a schematic drawing showing a general preparation of a cyclic compound of the invention via intramolecular dipolar cycloaddition.
Figure 14:
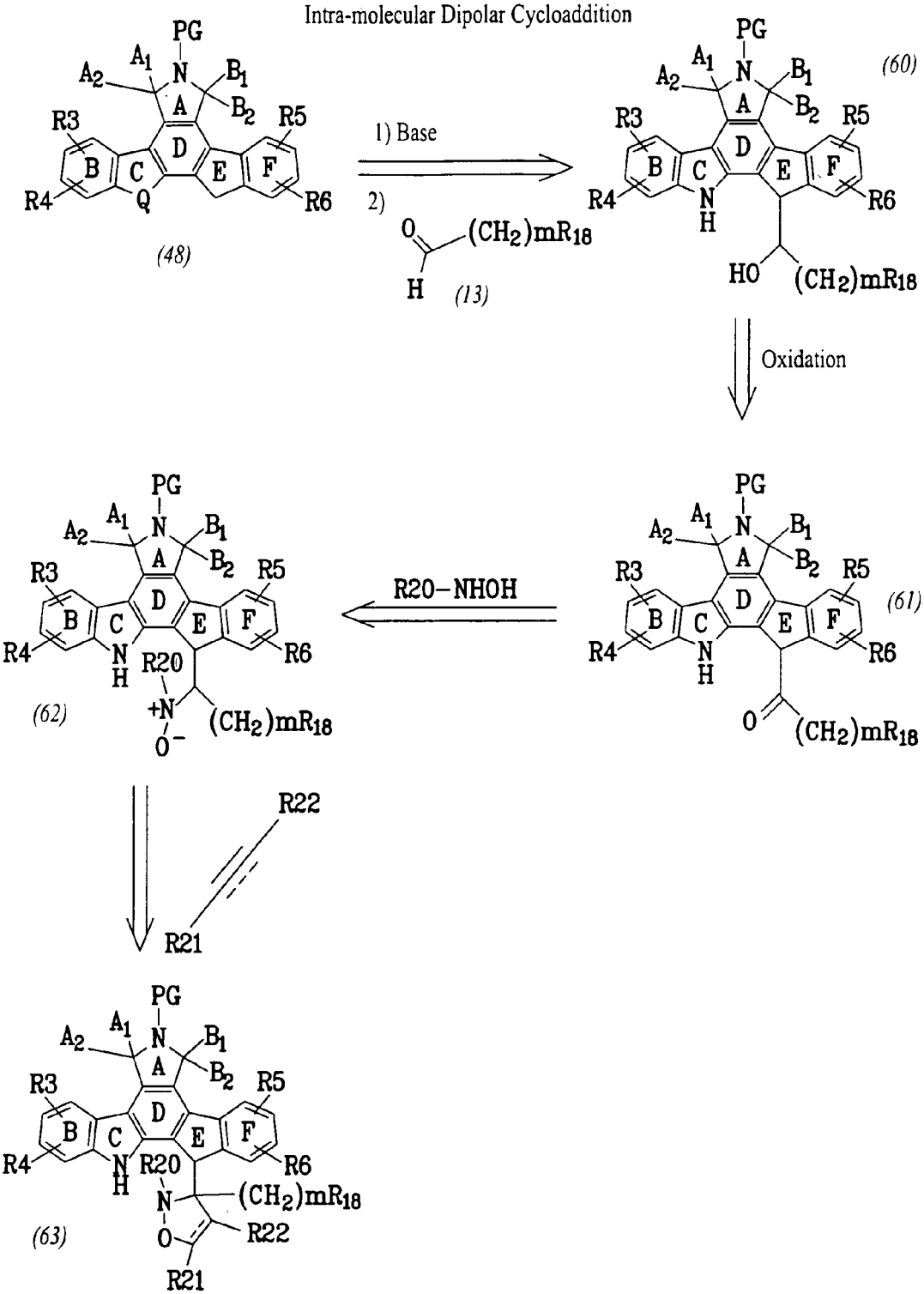
FIG. 14 is a schematic drawing showing a general preparation of a cyclic compound of the invention via intermolecular dipolar cycloaddition.
Figure 15:
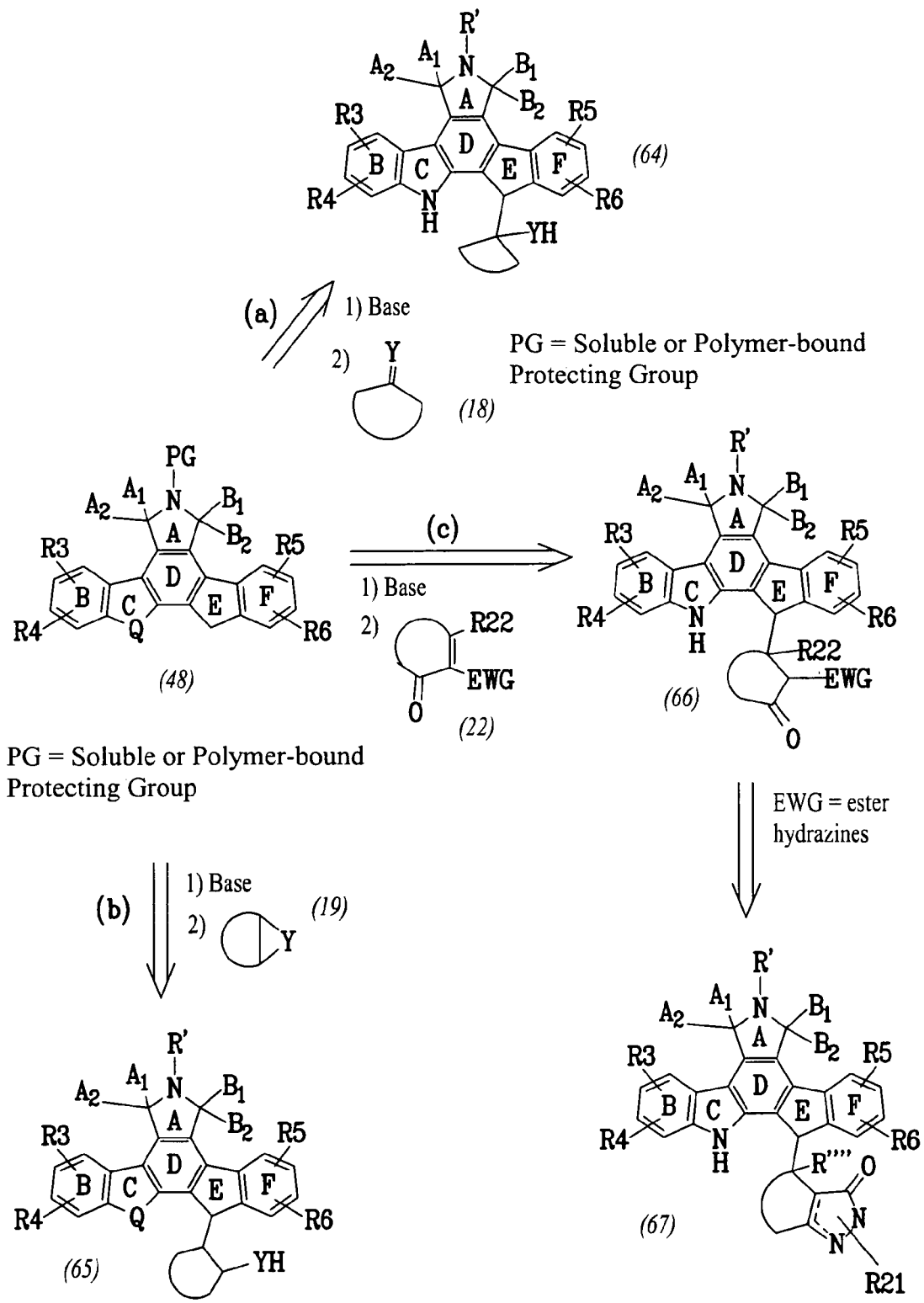
FIG. 15 is another schematic drawing showing a general preparation of a cyclic compound of the invention showing a general preparation of a cyclic compound of the invention by reaction of a carbanion intermediate with a cyclic ketone, an epoxide, oxirane or aziridine, and Michael addition.

Either an acid or a base-catalyzed process is used to carry out the lactam nitrogen protection strategy (shown in FIGS. 1, 10 and 11). The acid-catalyzed reaction can be carried out with a resin-bound reagent allowing immobilization of the fused pyrrolocarbazole (47) to a polymeric support, such as a polystyrene-based, Rink acid resin (FIG. 11) , providing (50). Alternatively, the acid-catalyzed reaction can be carried out with a soluble reagent, e.g. 4,4'-dimethoxybenzhydrol to yield a compound (49) (FIG. 11). The silyl-protected compound (51) is produced under base catalysis (FIG. 11).

Figure 2:
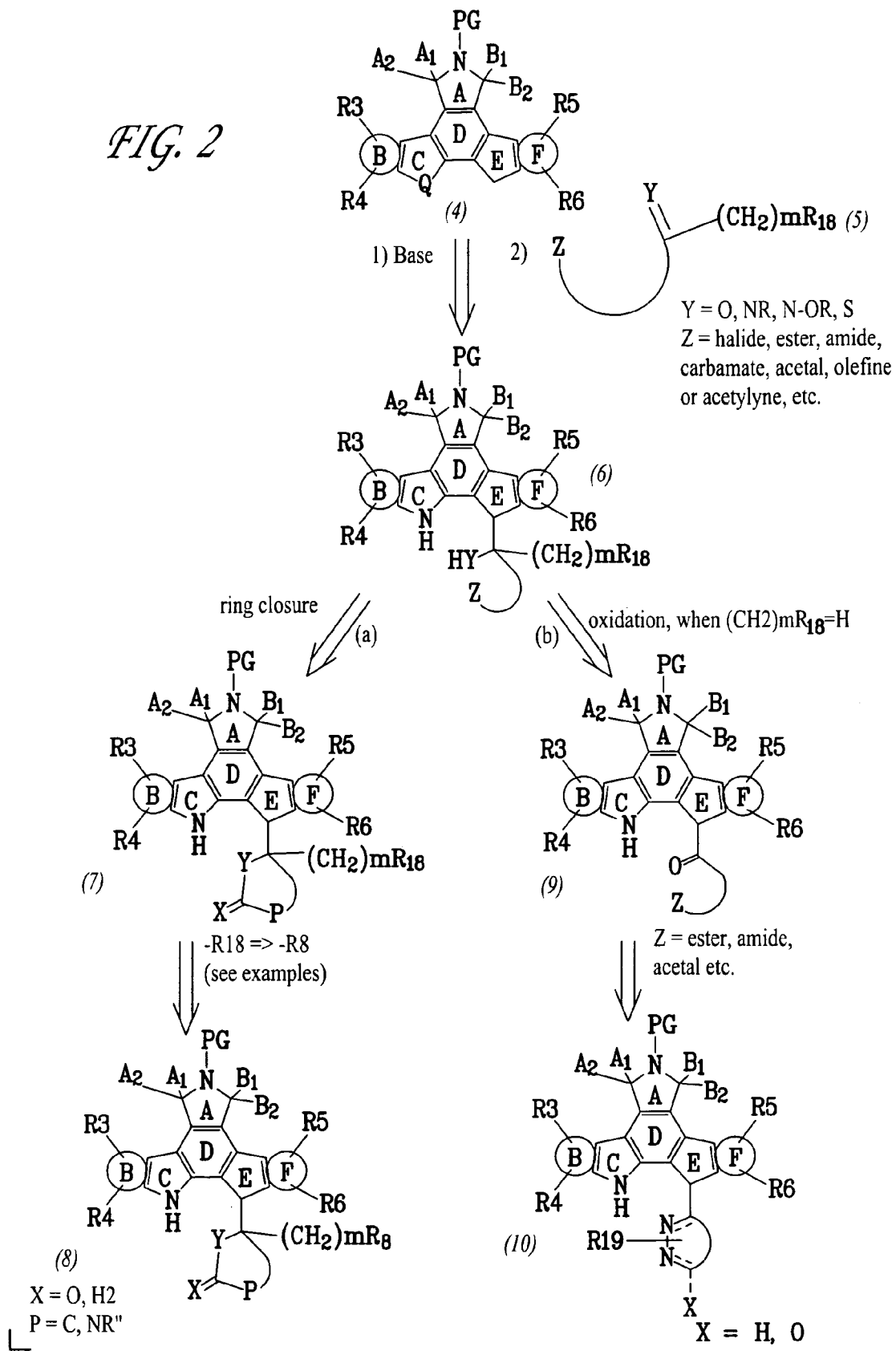
FIG. 2 is a schematic drawing showing a general preparation of a cyclic compound of the invention from an acyclic reagent.
Figure 3:
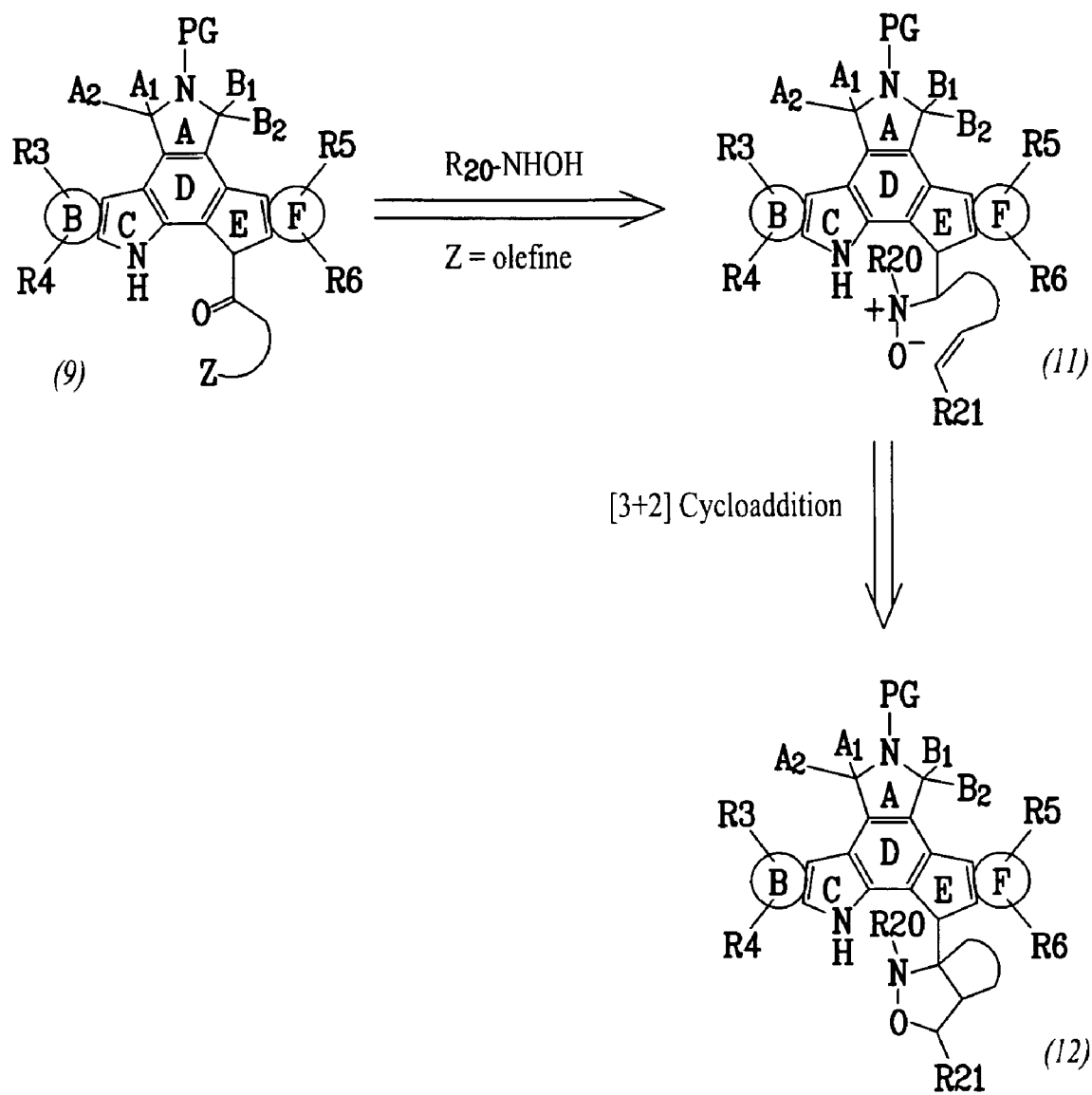
FIG. 3 is a schematic drawing showing a general preparation of a cyclic compound of the invention via intramolecular dipolar cycloaddition.
Figure 4:
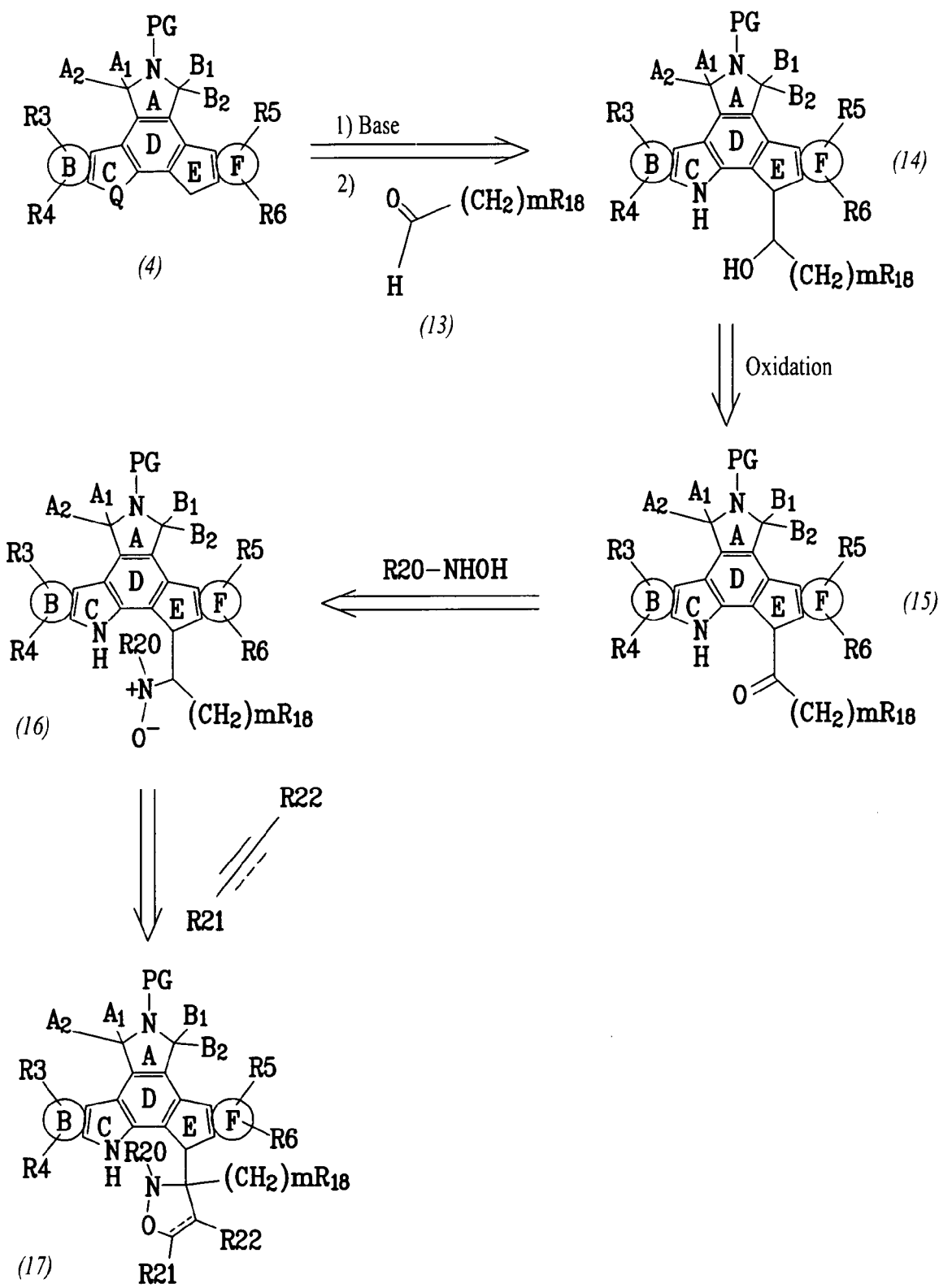
FIG. 4 is a schematic drawing showing another general preparation of a cyclic compound of the invention via intermolecular dipolar cycloaddition.
Figure 5:
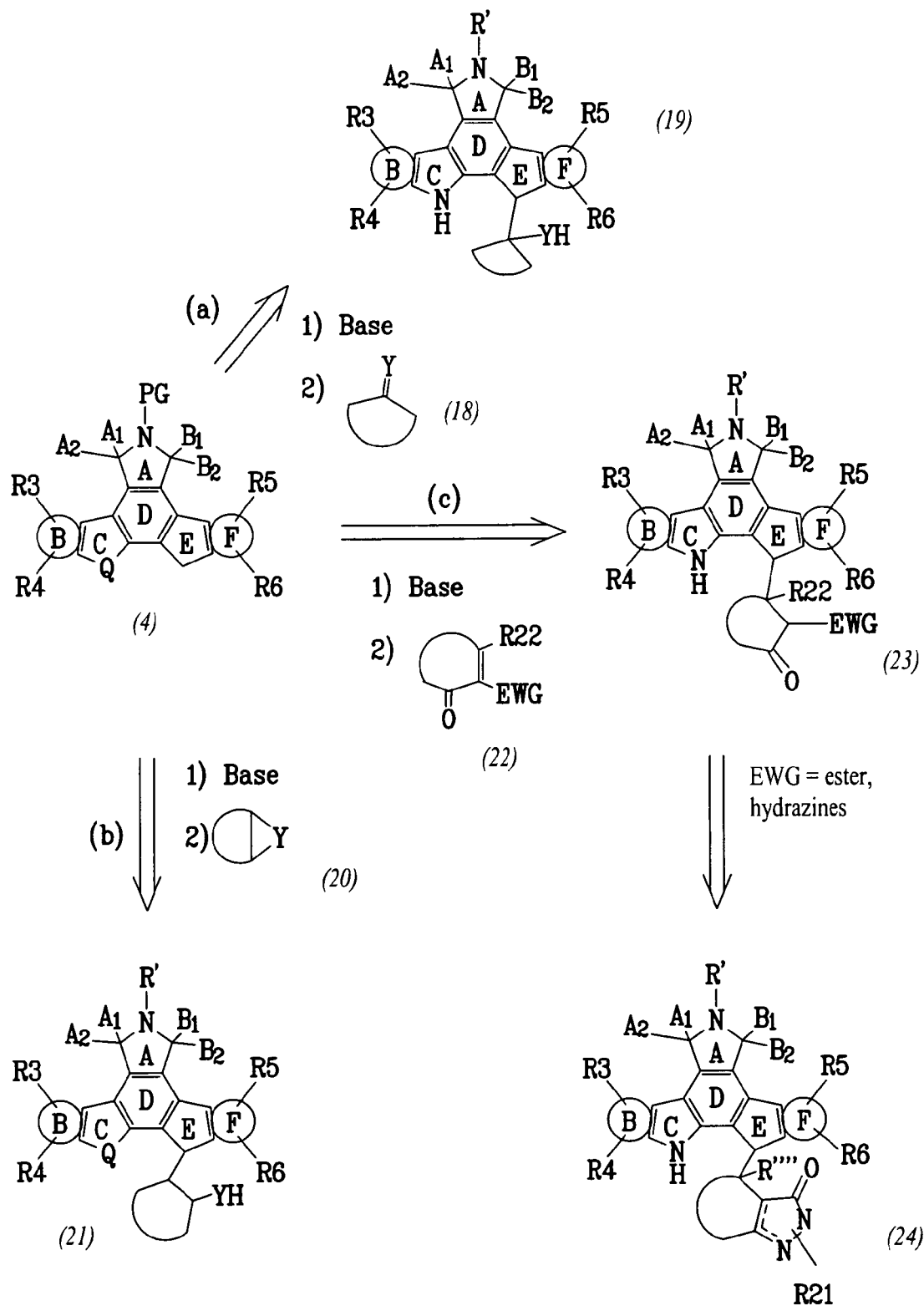
FIG. 5 is a schematic drawing showing a general preparation of a cyclic compound of the invention by reaction of a carbanion intermediate with a cyclic ketone, an epoxide, oxirane or aziridine, and Michael addition.

Reaction of the carbanion derived from (4)/(48) with a ω-functionalized ketone/aldehyde (5), [FIG. 2/12], provides an acyclic intermediate (6)/(53). The ring closure to provide (7)/(54) occurs typically in-situ when cyclization leads to a 5-membered (and occasionally to a 6-membered) product and when the Z group is an ester or a halide, such as chloride or bromide. For cases when ring closure leads to a six or higher membered cyclic product, the initially isolated acyclic derivative (6)/(53), is subsequently treated with a base providing the cyclic product, (7)/(54). The acyclic intermediates (6)/(53), derived from reaction with an aldehyde, upon oxidation provides a ketone intermediate (9)/(56). When the Z group is another carbonyl containing group (e.g. a tertiary amide), reaction with a hydrazine (or urea) leads to the formation of heterocyclic derivatives such as dihydropyrazol, pyrazol, pyridazinone, pyridazine dione or phthalazine dione, etc. (or dihydro-pyrimidone/dione, primidone/dione and/or homologs, etc). However, when the Z group is an olefin (or an acetylenic group), reaction of the keto-intermediate (9)/(56), with an N-alkyl hydroxyl amine provides a nitrone which subsequently leads to a cyclic product derived from an intramolecular dipolar cycloaddition reaction, (FIGS. 3/13). The secondary alcohol (14)/(60), produced from reaction with aldehyde (13), is oxidized to the ketone (15)/(61), which in turn is converted to the corresponding nitrone (16)/(62) (FIGS. 4/14). Reaction of this nitrone with an olefinic or acetylenic compound provides a cyclic derivative (17)/(63). Mono- or dialkylation of the anion(s) derived from (4)/(48), provide olefin containing fused pyrrolocarbazole (41)/(79) or (44)/(82), respectively (FIGS. 9/19). The C═C (olefin) group is subsequently converted to a cyclic derivative via analogous intermolecular dipolar cycloaddition reaction with a nitryloxide, nitrone or an azomethine ylide.

A cyclic group directly bonded to the carbazole nucleus is obtained (FIGS. 7/17) by reaction of the carbanion derived from (4)/(48) with highly electrophilic reagents such as N-acyl pyridinium compounds (30) [or pyridine N-oxide]. The dihyro derivatives (31)/(71) or (32)/(72) are either converted to the corresponding saturated cyclic analogs (35) or (36)/(75) or (76), or are aromatized to the corresponding heterocyclic derivatives (33) or (34)/(73) or (74). In a similar manner, reaction of (4)/(48) with a cyclic nitrone (37) gives the saturated heterocyclic derivatives (38)/(77).

Cyclic substituents are obtained by reaction of the carbanion derived from (4)/(48) with a cyclic ketone (18) (FIGS. 5/15), that may optionally contain a wide variety of functional groups (see example section). Otherwise, reaction of the carbanion derived from (4)/(48) with an epoxide, oxirane or an aziridine (FIGS. 5/15) yield cyclic substituents represented by (21)/(65). The carbanion derived from (4)/(48) also reacts with highly activated acrylate derivatives (22) (FIGS. 5/15) to provide cyclic derivatives (23)/(66). If the EWG in these products (23)/(66) is an ester function, further reaction with a hydrazine (or urea) leads to the formation of heterocyclic derivatives such as dihydro-pyrazol, pyrazol, pyridazinone, pyridazine dione, phthalazine dione, etc. (or dihydro-pyrimidone, dihydro-pyrimidone dione, primidone/dione, or homologs etc).

Cyclic substituents are obtained by further derivatization of the key aldehyde intermediate (90)/(99) with either (i) a difunctional reagents (91), such as amino-alcohol, amino-thiol diol, dithiols or diamines [(route (a) in FIGS. (20/21)], or (ii) via Diels-Alder reaction with a diene (93) as shown by route (b) in FIGS. (20/21). These cyclic substituents may optionally contain a wide variety of functional groups, either present in the difunctional reagent (91) or the diene; or alternatively by further functionalization of the olefine group present in (94)/(101) to provide (95)/(102).

Finally, a cyclic substituent is introduced by coupling an alkylating agent bearing an appropriately substituted cyclic group (FIGS. 8/18) with the carbanion derived from (4)/(48). When Q═NH, this reaction is facilitated by the presence of a tertiary amine base, an inorganic base such as alkali-metal carbonate, alkali-metal alkoxide, alkali-metal hydride or by use of an alkyl lithium or a Grignard base.

Figure 20:
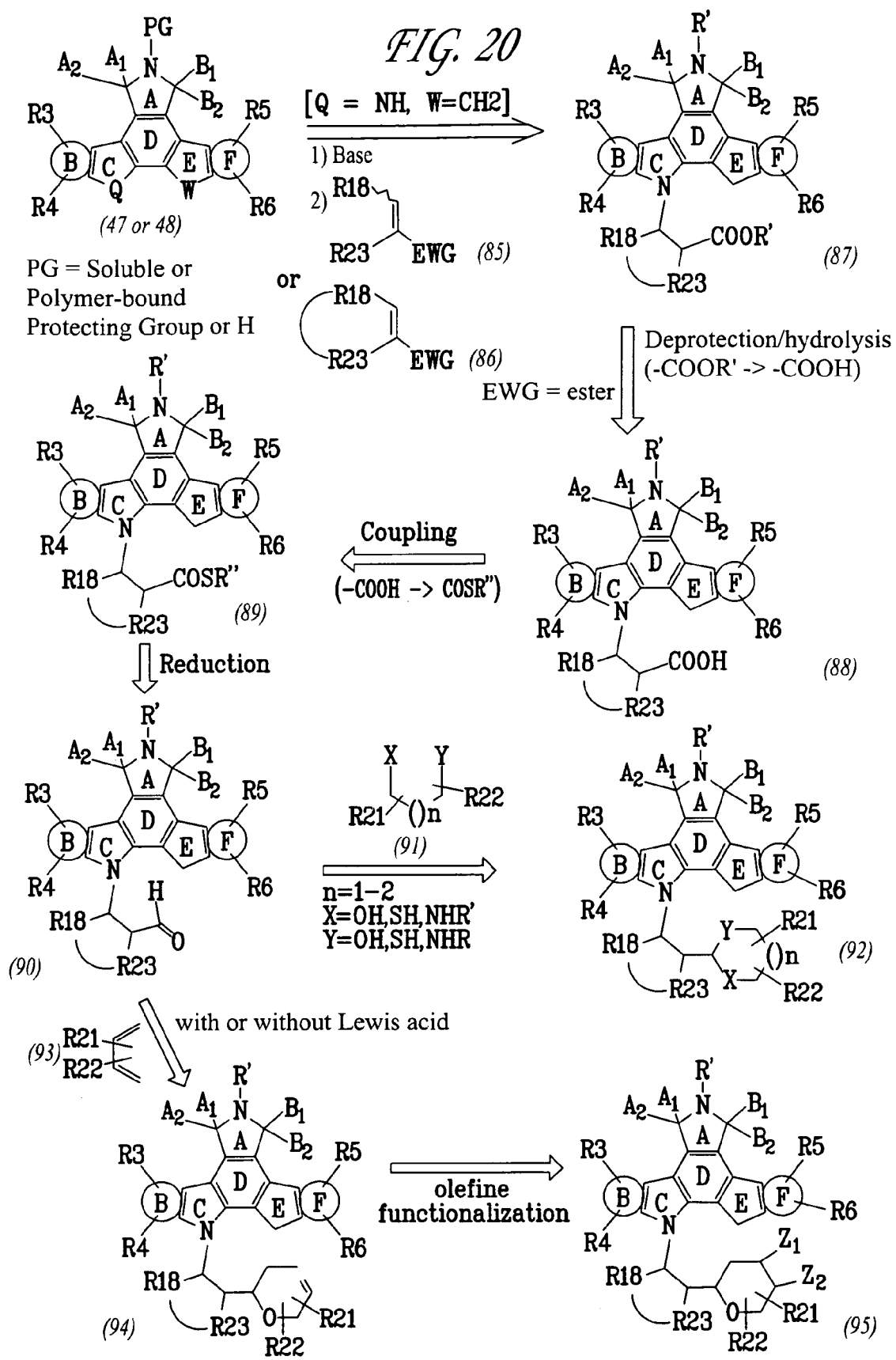
FIG. 20 is a schematic drawing showing a general preparation of a cyclic compound of the invention in which the cyclic substituent is formed from an aldehyde intermediate.

In a majority of the approaches described above for the preparation of fused pyrrolocarbazole containing cyclic substituents, the carbanion derived form (4)/(48) is used. Whereas, as described in FIGS. 20 and 21, it the nitrogen nucleophile which is utilized for functionalization to provide fused pyrrolocarbazole containing cyclic substituents. However, a route where the fused pyrrolocarbazole (4)/(48) serves as an electrophile is outlined in FIGS. 6/16. The methylene group of the fused pyrrolocarbazole (4)/(48) is oxidized to provide an electrophilic ketone (25)/(68). Addition of the anion (27) derived from a cyclic reagent (26) to the C=O of (25)/(68) provides a cyclic substituted product (29)/(69) that also contains a hydroxyl group at the benzylic position, as shown. This hydroxyl group is replaced by H, F, SR, OR or NRR'.

Furthermore, when Q=NH and W is a cyclic substituent, as described above, these analogs may be treated with an appropriately functionalized isocyanate to provide fused pyrrolocarbazoles containing cyclic substituents where Q=NC(=O)NHR'.

Examples below provide synthesis of a representative set of specific compounds, utilizing the general procedures described above.

Example 7

Preparation of Rink Resin-bound Intermediates (50a), (50b) and (50c) (FIG. 11)

Example 7A

A three neck round bottom flask fitted with an overhead mechanical stirrer and a Dean-Stark trap was sequentially charged with Rink acid resin (51b, R'=OMe, R"=polymer) (10.00 g, 0.64 mmol/g), 1-methyl-2-pyrolidinone (80 mL), benzene (350 mL), (47a) [A1,A2=H2, B1,B2=O, R3=R4=P5=R6=H, Q=NH] (3.00 g) and p-toluenesulfonic acid (1.00 g). The reaction mixture was warmed to reflux for 20 hours, cooled and then filtered. The resin was washed with THF (5×175 mL) and the filtrate set aside. The resin was then sequentially washed with DMSO (4×100 mL), 2% aqueous NaHCO$_3$ (4×100 mL), water (4×100 mL), DMSO (2×200 mL), THF (4×100 mL) and ethyl acetate (4×100 mL). The resin was dried under vacuum (24 hours) to afford 11.70 g (0.47 mmol/g) of resin (50a) ) [A1,A2=H2, B1,B2=O, R3=R4=R5=R6=H)].

The original THF washings were evaporated, the residue was diluted with water (750 mL), and the resulting precipitate was filtered and sequentially washed with water, 2% aqueous NaHCO$_3$ (4×100 mL), and water (4×100 mL). After drying under vacuum, 1.28 g of (47a) was recovered.

Example 7B

In a similar manner, (47b) [A1,A2=H2, B1,B2=O, R3=R4=R5=H, R6=10-OMe, Q=NH], (1.02 g) was coupled to the Rink acid resin (51b) (3.12 g) to afford 3.70 g (0.46 mmol/g) of resin bound compound, (50b), along with recovered starting material (47b) (0.44 g).

Example 7C

In a similar manner, (47c) [A1,A2=O, B1,B2=H2, R3=R4=R5=R6=H, Q=NH], (0.5 g) was coupled to Rink acid resin (51b) (1.52 g) to afford resin bound compound, (50c), (1.58 g).

Example 7D

Preparation of Intermediate (49a) (FIG. 11)

A three neck round bottom flask fitted with an overhead mechanical stirrer and a Dean-Stark trap was sequentially charged with DMB-OH (51a) (2.44 g, 10 mmoles), 1-methyl-2-pyrolidinone (30 mL), benzene (270 mL), (47a) (3.10 g, 10 mmol) and p-toluenesulfonic acid (1.90 g, 10 mmoles). The reaction mixture was heated to reflux. After 2 h, the reaction mixture became homogenous, and heating was continued for another 2 h. The reaction mixture was cooled to room temperature, diluted with EtOAc (200 mL), washed with saturated aqueous NaHCO$_3$ solution (4×100 mL), water (4×100 mL), and the organic layer was dried over anhydrous MgSO$_4$, filtered and concentrated in-vacuo. The residue was triturated with EtOAc/hexane and the resulting solid was filtered and dried under high vacuum to afford (49a) [A1, A2=H2, B1,B2=O, R3=R4=R5=R6=H, Q=NH, R'=R"=H], (5.2 g, 98%).

Example 8

General Synthesis of Cyclic Derivatives by Solid Phase Chemistry (SPS).

To a suspension of (50a) or (50a) or (50c) (50 mg) in THF (2 mL) was added a 1.0 M solution of EtMgBr (1.0 mL in THF) and the reaction was stirred for 1 h prior to the addition of HMPA (0.5 mL). After stirring for 10 min, the electrophile (e.g., aldehyde, ketone, epoxide, etc.) (~10–15 mmole) was added, and the reaction was stirred for 20 h. The reaction was quenched with 10% aqueous NH$_4$Cl (5 mL) and filtered. The resin was successively washed with 10% aqueous NH$_4$Cl (3×10 mL), water (3×10 mL), THF (3×10 mL), DMF (3×10 mL), water (3×10 mL), THF (3×10 mL), and ether (3×10 mL). The resin was dried under vacuum, taken up in methylene chloride (15 mL), and treated with trifluoroacetic acid (0.15 mL). After stirring for 1 h, the reaction was filtered, and the filtrate was evaporated. The resulting residue was analyzed by analytical HPLC (see method description below) and those samples less than 80% pure were purified by preparative HPLC (Zorbax RX-8, 4×25 cm, eluted with MeCN/water containing 0.1% trifluoroacetic acid, gradient). The appropriate fractions were neutralized with NaHCO$_3$ and extracted into methylene chloride (3×50 mL) and dried over MgSO$_4$. The desired compounds were obtained after filtration and solvent evaporation.

Analytical HPLC Methods:
Method A: Column: Zorbax analytical RX-C8, 4.6 mm×250 mm.
  Conditions: 10% MeCN-->100% MeCN (w/0.1% TFA) over 40 minutes.
Method B: Column: Vydac analytical C8, 4.6 mm×150 mm.
  Conditions: 35% MeCN-->60% MeCN (w/0.1% TFA) over 20 minutes.
Method C: Column: Zorbax analytical RX-C8, 4.6 mm×150 mm.
  Conditions: 10% MeCN-->100% MeCN (w/0.1% TFA) over 20 minutes.
Method D: Column: Zorbax analytical RX-C8 4.6 mm×250 mm.
  Conditions: 10% MeCN->100% MeCN (w/0.1% TFA) over 40 minutes.

Example 9

Preparation of Compound II-01a

A solution of (47a) (2.02 g, 6.5 mmol) in DMF (200 mL) was heated (155° C. oil bath) under vacuum and solvent was reduced by distillation (~70 mL). After cooling to room temperature, nitrogen was bled into the system and the distillation head was replaced with a septum and $N_2$ bubbler. Sodium hydride (274 mg, 8.15 mmol of a 60% dispersion in mineral oil) was added in one portion and the reaction was then heated to 55° C. and stirred for 1 h. (+/−) Glycidil mesylate (1.69 g, 8.15 mmol) was then added and the reaction was stirred for an additional 15 h at 55° C. The oil-bath was removed and the reaction was stirred at room temperature for 24 h. The crude mixture was filtered and the mother liquor concentrated and triturated with diethyl ether/methanol. The solid was collected by filtration and washed with water and dried to give the desired product II-10a as a pale green solid (1.7 g, 4.62 mmol, 71%), which had the following spectral properties. 300 MHz $^1$H NMR (DMSO d$_6$) δ 9.50 (d, 1), 8.58 (s, 1), 8.01 (d, 1), 7.74 (d, 1), 7.68 (d, 1), 7.50 (dd, 1), 7.44–7.31 (m, 3), 5.18 (m, 1), 4.95 (s, 2), 4.74 (dd, 1), 4.50 (s, 2), 3.53 (m, 1), 2.8 (t, 1), 2.48 (m, 1); ESI MS calcd for $C_{24}H_{18}N_2O_2$ (M+H) 367.44, found 367.14.

Example 10

Preparation of Compound II-01b

A solution of (47a) (320 mg, 1.1 mmol) in DMF (35 mL) was heated (155° C. oil bath) under vacuum and solvent was reduced by distillation (~15 mL). After cooling to room temperature, nitrogen was bled into the system and the distillation head was replaced with a septum and $N_2$ bubbler. Sodium hydride (49 mg, 1.1 mmol of a 60% dispersion in mineral oil) was added in one portion and the reaction was stirred for 1 h at room temperature. 2-R(−) Glycidyl tosylate (283 mg, 1.24 mmol) was then added and the reaction was stirred an additional 18 h at 60° C. The oil-bath was removed and the reaction was stirred at room temperature for 4 h. The crude mixture was dried, triturated with diethyl ether/methanol and then taken up in THF and filtered. The THF filtrate was concentrated and the resultant solid was triturated with diethyl ether/methanol and dried to give of the desired product II-01b (155 mg, 0.42 mmol, 37%) as a greenish solid. Further concentration and trituration of the mother liquor provided an additional amount of the product II-01b (90 mg). The product II-01b had the following spectral properties: 300 MHz $^1$H NMR (DMSO d$_6$) δ 9.50 (d, 1), 8.58 (s, 1), 8.01 (d, 1), 7.74 (d, 1), 7.68 (d, 1), 7.50 (dd, 1), 7.44–7.31 (m, 3), 5.18 (m, 1), 4.95 (s, 2), 4.74 (dd, 1), 4.50 (s, 2), 3.53 (m, 1), 2.8 (t, 1), 2.48 (m, 1).

Example 11

Preparation of Compound II-01c

This compound was prepared using the same procedure as II-01b using (47a) (300 mg, 0.97 mmol), NaH (46 mg, 0.97 mmol) and 2-S(+)-glycidyl tosylate (265 mg, 1.2 mmol) in DMF (10 mL). The desired product (277 mg, 0.76 mmol, 78%) was obtained, which had the following spectral properties: 300 MHz $^1$H NMR (DMSO d$_6$) δ 9.50 (d, 1), 8.60 (s, 1), 8.02 (d, 1), 7.78 (d, 1), 7.68 (d, 1), 7.53 (t, 1), 7.44–7.38 (m, 3), 5.20 (m, 1), 4.95 (s, 2), 4.74 (dd, 1), 4.50 (s, 2), 3.53 (m, 1), 2.8 (t, 1), 2.48 (m, 1).

Example 12

Preparation of Compound II-02

Following the general SPS procedure as described in Example 8, (50a) (50 mg) was reacted with 1-benzyl-4-piperidone to provide 9 mg of the desired compound which had the following physical properties: HPLC: $R_t$=21.36 min. (Method D). MS: 500 (M+H). $^1$HNMR (DMSOd$_6$): δ 11.13 (s, 1H), 9.40 (d, J=7.57 Hz, 1H), 8.57 (s, 1H), 7.95 (d, J=7.81 Hz, 1H), 7.6–7.11 (series of m, 11H), 4.90 (s, 2H), 4.88 (s, 1H), 4.49 (s br, 2H), 3.66–1.03 (series of m, 8H).

Example 13

Preparation of Compound II-03

Following the general SPS procedure as described in Example 8, (50a) (50 mg) was reacted with tetrahydro-4H-pyranone to provide 11 mg of the desired compound which had the following physical properties: HPLC: $R_t$=23.85 min. (Method D). MS: 411 (M+H). $^1$HNMR (DMSOd$_6$): δ 11.07 (s, 1H), 9.42 (d, J=7.59 Hz, 1H), 8.52 (s, 1H), 7.9–7.22 (series of m, 7H), 4.89 (s, 2H), 4.39 (s, 1H), 3.6–0.83 (series of m, 8H).

Example 14

Preparation of Compound II-04

Following the general SPS procedure as described in Example 8, (50a) (50 mg) was reacted with 5-chloro-pentan-2-one to provide 10 mg of the desired compound as a set of diastereomers which had the following physical properties: HPLC: $R_t$=32.1 min, and 33.0 min. (Method A). MS: 395 (M+H).

Example 15

Preparation of Compound II-05

Following the general SPS procedure as described in Example 8, (50a) (50 mg) was reacted with methyl 2-keto-hexonoate [which was prepared according to a literature procedure of E. J. Corey, et. al., *Tett. Letters*, 1985, 3919–22], to provide 6 mg of the desired compound as a set of diastereomers which had the following physical properties: HPLC: $R_t$=25.5 min, and 26.0 min. (Method A). MS: 409 (M+H), 431 (M+Na).

Example 16

Preparation of Compound II-06

Following the general SPS procedure as described in Example 8, (50a) (50 mg) was reacted with methyl 2-keto-pentanoate [which was prepared according to a literature procedure of C. Hershburg, *Org. Syn.*, 1955, 627], to provide 6 mg of the desired compound as a set of diastereomers which had the following physical properties: HPLC: $R_t$=24.1 min, and 25.6 min. (Method A). MS: 395 (M+H).

Example 17

Preparation of Compound II-07

Following the general SPS procedure as described in Example 8, (50a) (50 mg) was reacted with 4-chlorobutyraldehyde [which was prepared according to a literature procedure of M. E. Kuehene et. al., *J. Org. Chem.* 1981, 46, 2002–09], to provide 6.9 mg of the desired compound as a set of diastereomers which had the following physical properties: HPLC: $R_t$=28.6 min, and 30.0 min. (Method A). MS: 381 (M+H).

Example 18

Preparation of Compound II-08

Following the general SPS procedure as described in Example 8, (50a) (50 mg) was reacted with 4-chloro-4'-fluorobutyrophenone to provide 10.1 mg of the desired compound as a set of diastereomers which had the following physical properties: HPLC: $R_t$=32.8 min, and 35.0 min. (Method A). MS: 475 (M+H).

Example 19

Preparation of Compound II-09

Following the general SPS procedure as described in Example 8, (50a) (50 mg) was reacted with 4-chloro-(2-thiophinyl)butyronone to provide 7.6 mg of the desired compound as a set of diastereomers which had the following physical properties: HPLC: $R_t$=31.5 min, and 34.8 min. (Method A). MS: 463 (M+H).

Example 20

Preparation of Compound II-10

Following the general SPS procedure as described in Example 8, (50a) (50 mg) was reacted with 1-methyl-4-piperidone to provide 6 mg of the desired compound which had the following physical and spectral properties: HPLC: $R_t$=16.66 min. (Method D). MS: 424(M+H). $^1$HNMR (DMSO$d_6$): δ 11.16 (s, 1H), 9.45 (d, J=7.73 Hz, 1H), 8.62 (s, 1H), 8.01 (d, J=7.62 Hz, 1H), 7.7–7.25 (series of m, 6H), 4.94 (s, 2H), 4.54 (s, 1H), 3.8–1.9 (s and series of m, 11H).

Example 21

Preparation of Compound II-11

Following the general SPS procedure as described in Example 8, (50a) (50 mg) was reacted with 3,4-epoxytetrahydrothiophene to provide 7 mg of the desired compound as a set of diastereomers which had the following physical and spectral properties: HPLC: $R_t$ (major diastereomer)=27.19 min, $R_t$ (minor diastereomer)=27.34 min. (Method D). Diastereomeric Ratio: ~60:40. MS: 413(M+H). $^1$HNMR (DMSO $d_6$) δ 11.21 & 11.1 (2s, 1H), 9.43(m, 1H), 8.55(2s, 1H), 7.96–7.11 (series of m, 7H), 4.89 (s, 2H), 4.67 (s, 1H), 3.00–1.3 (series of m, 6H).

Example 22

Preparation of Compound II-12

Following the general SPS procedure as described in Example 8, (50a) (50 mg) was reacted with 6-bromo-hexan-2-one [which was prepared according to a literature procedure of Flannery et. al., *J. Org. Chem.* 1972, 37, 2803] and the crude product was purified by preparative TLC to provide 2.5 mg of the desired product as a set of diastereomers which had the following physical properties: HPLC: $R_t$=33.9 min, and 34.1 min. (Method A). MS: 409 (M+H).

Example 23

Preparation of Compound II-13

Following the general SPS procedure as described in Example 8, (50a) (50 mg) was reacted with 5-bromopentan-1-al [which was prepared according to a literature procedure of M. E. Kuehene et. al., *J. Org. Chem.* 1981, 46, 2002–09], to provide 8.8 mg of the desired compound as a set of diastereomers which had the following physical properties: HPLC: $R_t$=31.3 min, and 35.4 min. (Method A). MS: 395 (M+H).

Example 24

Preparation of Compound II-14

Following the general SPS procedure as described in Example 8, (50a) (50 mg) was reacted with tetrahydrothiopyran-4-one to provide 8.8 mg of the desired compound which had the following physical properties: HPLC: $R_t$=28.21 min. (Method D). MS: 427(M+H)

Example 25

Preparation of Compound II-15

Following the general SPS procedure as described in Example 8, (50a) (50 mg) was reacted with β-tetralone to provide 8 mg of the desired compound as a set of diastereomers which had the following physical properties: HPLC: $R_t$ (major diastereomer)=32.83 min., $R_t$ (minor diastereomer)=32.38 min. (Method D). Diastereomeric Ratio ~55:45. MS: 457(M+H)

Example 26

Preparation of Compound II-16

Following the general SPS procedure as described in Example 8, (50a) (50 mg) was reacted with 1-ethyl-3-piperidone to provide 8 mg of the desired compound as a set of diastereomers which had the following physical and spectral properties: HPLC: $R_t$ (major diastereomer)=18.36 min, $R_t$ (minor diastereomer)=17.83 min. (Method D). Diastereomeric Ratio: 57:43. MS: 438(M+H). $^1$HNMR (DMSO $d_6$): δ 11.32 & 11.16 (s, 1H), 9.46(m, 1H), 8.7 (m, 1H), 8.01 (d, J=7.71 Hz, 1H), 7.78–7.25 (series of m, 6H), 4.95 (overlapping s, 2H), 4.60 & 4.57 (2s, 1H), 3.8–0.8 (series of m, 13H).

Example 27

Preparation of Compound II-17

Following the general SPS procedure as described in Example 8, (50a) (50 mg) was reacted with 2-(N-morpholinomethyl)cyclopentanone to provide 8 mg of the desired compound as a set of diastereomers which had the following physical and spectral properties: HPLC: $R_t$ (major diastereomer)=18.37 min., $R_t$ (minor diastereomer)=19.81 min. (Method D). Diastereomeric Ratio: 80:20. MS: 494(M+H). $^1$HNMR (Major, DMSO $d_6$): δ 11.07 (s, 1H), 9.44 (d, J=7.63 Hz, 1H), 8.59 (s, 1H), 7.99–7.09(series of m, 7H), 4.93 (s, 2H), 4.68 (s, 1H), 4.0–1.1(series of m, 17H).

Example 28

Preparation of Compound II-18

Following the general SPS procedure as described in Example 8, (50a) (50 mg) was reacted with cyclobutanone to provide 6 mg of the desired which had the following physical and spectral properties: HPLC: $R_t$=27.42 min. (Method D). MS: 381(M+H). $^1$HNMR (DMSO $d_6$): δ 11.07 (s, 1H), 9.43 (d, J=7.68 Hz, 1H), 8.52 (s, 1H), 7.93 (d, J=7.78 Hz, 1H), 7.79 (d, J=7.44 Hz, 1H), 7.67 (d, J=8.08 Hz, 1H), 7.4–7.14 (m, 4H), 4.89 (s, 2H), 4.36 (s, 1H), 2.7–0.8 (series of m, 6H).

Example 29

Preparation of Compound II-19

Following the general SPS procedure as described in Example 8, (50a) (50 mg) was reacted with 1,7-dichloro heptan-4-one to provide 7.6 mg of the desired compound as a set of diastereomers which had the following physical properties: HPLC: $R_t$=34.0 min, and 35.3 min. (Method A). MS: 457/459 (M+H).

Example 30

Preparation of Compound II-20 and II-32

Following the general SPS procedure as described in Example 8, (50a) (50 mg) was reacted with 5-chloro-(1-pivalyl)-pentan-2-one [which was prepared according to a literature procedure of P. Knochel et. al., *J. Org. Chem.* 1993, 58, 588–99] and the crude product was titurated with acetonitrile to provide 5.3 mg of the desired compound as a set of diastereomers which had the following physical properties: HPLC: $R_t$=34.4 min, and 35.9 min. (Method A). MS: 495 (M+H).

The acetonitrile mother liquor was purified via chromatography (reverse phase C-8 column w/60% MeCN-40% water containing 0.1% TFA to provide II-32 (R18=Et). HPLC: $R_t$=35.3 min (Method A). MS: 545 (M+H).

Example 31

Preparation of Compound II-21

A solution of the product II-20 (20 mg) in THF (2 mL) was treated with a solution of LiBH$_4$ in THF (0.5 mL, 2M solution) at room temperature for 30 min. The reaction mixture was quenched with 1N HCl (2 mL), EtOAc was added and the reaction mixture was stirred for 1.5 h. The reaction mixture was neutralized with aq. NaHCO$_3$ solution, and the organic phase was separated, washed with brine, dried over anhydrous Na$_2$SO$_4$ and concentrated in vacuo. The residue was taken up in toluene with minimal amounts of THF to provide a clear solution which was filtered through a pad of silica and eluted with 50% THF-toluene and evaporated to provide II-21 as a mixture of diastereomers which had the following physical properties: HPLC: $R_t$=24.9 min, and 26.7 min. (Method A). MS: 411 (M+H).

Example 32

Preparation of Compound II-22

To a solution of the alcohol II-21 (5 mg), in CH$_2$Cl$_2$ (2 mL) was added Et$_3$N (15 µL), acetic anhydride (10 µL), and a crystal of N,N-dimethylaminopyridine. The reaction mixture was stirred at room temperature for 30 min, quenched with aq. NaHCO$_3$ solution and extracted into EtOAc. The organic layer was washed with 1N HCl solution, brine and then dried over anhydrous MgSO$_4$. Concentration in vacuo provided II-22 as a mixture of diastereomers which had the following physical properties: HPLC: $R_t$=29.2 min, and 30. min. (Method A). MS: 453 (M+H) and 475 (M+Na).

Example 33

Preparation of Compound II-23

Following the general SPS procedure as described in Example 8, (50a) (50 mg) was reacted with diethoxy butyraldehyde [which was prepared according to a literature procedure of L. A. Paquette et. al., *J. Am. Chem. Soc.*, 1997, 119, 9662] to provide 6.2 mg of the desired compound which had the following physical properties: HPLC: $R_t$=23.2 min. (Method A). MS: 397 (M+H).

Example 34

Preparation of Compound II-24

Following the general SPS procedure as described in Example 8, (50a) (50 mg) was reacted with 1-actetyl-4-piperidone to provide 6 mg of the desired compound which had the following physical and spectral properties: HPLC: $R_t$=21.06 min. (Method D). MS: 452(M+H). $^1$HNMR (DMSO $d_6$): δ 11.06 (2s, 1H), 9.41 (d, J=7.53 Hz, 1H), 8.53 (s, 1H), 7.94 (d, J=7.59 Hz, 1H), 7.7–7.1 (a series of m, 7H), 4.89 (s, 2H), 4.5–0.5 (a series of s and m, 12H).

Example 35

Preparation of Compound II-25

To a solution of ethyl vinyl ether (3.0 mL) in THF (14 mL) at −78C under argon atm. was added tert-BuLi (12.0 mL, 1.7 M in pentane). The reaction mixture was warmed to −40C for 10 min., then to room temperature for 5 min, recooled to −78C and was added to a suspension of CuBr.DMS (2.05 g) in THF (7 mL) kept at −40C. After 30 min., 1,3-dichloroisobutene (3.0 mL) was added rapidly, and the reaction was allowed gradually to warm to room temperature and stirred for 4 h. The reaction mixture was quenched with 10% NH$_4$Cl solution. This mixture was filtered and the solid was washed with ether. The organic layer was washed with aq. NaHCO$_3$ solution, brine and dried over MgSO$_4$, and concentrated in vacuo. The residue was taken up in methanol (15 mL) and treated with HCl (0.4 mL). When no starting material was apparent by TLC, solvent was removed in vacuo, the residue was treated with aq. NaHCO$_3$ and the mixture was extracted with ether (3×30 mL). The ether layer was washed with brine and dried over anhydrous MgSO$_4$ and concentrated in-vacuo. The residual material was purified over silica gel and eluted with 20% EtOAc in hexane to yield 3-acetyl-4-chloro-isobutene.

Following the general SPS procedure as described in Example 8, (50*a*) (50 mg) was reacted with 3-acetyl-4-chloro-isobutene (as described above) to provide 2.15 mg of the desired compound which had the following physical properties: HPLC: R$_t$=34.0 min. and 34.9 min. (Method A). MS: 407 (M+H).

Example 36

Preparation of Compound II-26

A suspension of resin-bound compound II-25 (prior to cleavage of product II-25 with TFA) in THF (10 mL) was treated with OsO$_4$ solution (100 μL of 0.1 M solution in CCl$_4$) n-methyl morpholine N-oxide (50 mg) and water (100 μL). After stirring overnight, the reaction mixture was quenched with 10% NH$_4$Cl solution, the resin was washed, and product released from resin as described in Example 8, to yield compound II-26 as a mixture of diastereomers which had the following physical properties: HPLC: R$_t$=20.0 min. and 21.2 min. (Method A). MS: 441 (M+H).

Example 37

Preparation of Compound II-27

A portion of the product II-26 (2 mg) was taken up in THF (4 mL), and was treated with water (1.5 mL) and NaIO$_4$ (50 mg) at room temperature for ~16 h. The reaction was quenched with aq. NaHCO$_3$ solution and extracted into EtOAc. The organic layer was dried over MgSO$_4$, filtered and concentrated in vacuo to provide II-27 as a mixture of diastereomers which had the following physical properties: HPLC: R$_t$=27.3 min. and 28.2 min. (Method A). MS: 431 (M+Na).

Example 38

Preparation of Compound II-28

To a mixture of N,O-dimethyl hydroxyl amine hydrochloride (13.0 g) in CH$_2$Cl$_2$ (500 mL) at 0° C. was added Et$_3$N ( 36 mL) and 5-chlorovaleryl chloride. The reaction mixture was warmed to room temperature and stirred for 2 h. The reaction was quenched with aq. NaHCO$_3$ solution, washed with 1N HCl solution and brine. The organic layer was dried over anhydrous MgSO$_4$, filtered, concentrated in vacuo and the residue distilled @ 0.1 mm of Hg (78–81° C.). To a solution of the amide (2.0 g). in THF (15 mL) at −78° C. was added a solution of vinyl magnesium bromide (17 mL, 1M solution), the mixture was warmed to 0° C. for 1 h and then stirred at room temperature for 30 min. The reaction mixture was recooled to 0° C. and quenched with ice cold 1N HCl. The product was extracted with ether, dried over MgSO$_4$, filtered and concentrated to ~8 mL volume.

Following the general SPS procedure as described in Example 8, (50*a*) (50 mg) was reacted with the ether solution of the 6-chloro-3-hex-1-eneone (as described above) to provide 5.2 mg of the desired compound II-28 as a mixture of diastereomers which had the following physical properties: HPLC: R$_t$=32.4 min. and 35.6 min. (Method A). MS: 407 (M+H).

Example 39

Preparation of Compound II-29

A suspension of resin-bound compound II-28 (prior to cleavage of product II-27 with TFA) in THF (10 mL) was treated with OsO$_4$ solution (100 μL of 0.1 M solution in CCl$_4$) n-methyl morpholine N-oxide (50 mg) and water (100 μL). The reaction mixture was protected from light with aluminum foil and stirred overnight. The reaction mixture was quenched with 10% NH$_4$Cl solution and the resin was washed and product was released from resin as described in Example 8. The crude diol was purified via preparative thin layer chromatography (60% THF in toluene) to provide the product, II-29, which had the following physical properties: HPLC: R$_t$=21.6 min. (Method A). MS: 441 (M+H) and 463 (M+Na).

Example 40

Preparation of Compounds II-30a and II-30b

Compound (II-04) (two diastereomers) was purified as described previously, and each diastereomer was isolated by preparative HPLC as described in the General Synthesis. One diastereomer had HPLC R$_t$=32.1 min (Method A) and MS=395 (M+H); the other had a HPLC R$_t$=33.0 min (Method A) and MS=395 (M+H).

Example 41

Preparation of Compound II-31

Following the general SPS procedure as described in Example 8, (50*a*) (50 mg) was reacted with ethyl 5,7,9-trioxa-3-oxo-decanoate [which was prepared according to a literature procedure according to O. Kalinnkovick et. al., *Tett. Lett.*, 1996, 10956] to provide 16 mg of the lactones II-31 as a mixture of diastereomers which had the following physical properties: HPLC: R$_t$=24.1 min. and 25.2 min. (Method A). MS: 469 (M+H) and 491 (M+Na).

Example 42

Preparation of Compound II-33

A portion (10 mg) of the MOM-ether (II-31) was taken up in methanol (4 mL), treated with several drops of 6N HCl solution and was warmed to 55 C for 2 h. Solvent was removed by rotary evaporation and the crude product was purified by preparative TLC with 50% THF/toluene to provide 1 mg of hydroxy lactones (II-33) as a mixture of diastereomers which had the following physical properties: HPLC: R$_t$=19.6 min. and 19.8 min. (Method A). MS: 425 (M+H) and 447 (M+Na).

Example 43

Preparation of Compound II-34

To a solution of the pivalate II-32 (5 mg) in THF (5 mL) was added a solution of LiBH$_4$ in THF (1 mL, 2M solution) and the reaction mixture was stirred at room temperature for 5 h, quenched with 1N HCl (2 mL) and taken up in EtOAc. The reaction mixture was neutralized with aq. NaHCO$_3$ solution, the organic phase was separated, washed with brine, dried over anhydrous Na$_2$SO$_4$, filtered and concentrated in vacuo. The residue was taken in toluene with minimal amounts of THF to provide a clear solution and was purified by column chromatography on silica gel (eluted with 55% THF in toluene) to provide II-34 (3.34 mg) which had the following physical properties: HPLC: R$_t$=25.3 min. (Method A). MS: 439 (M+H).

Example 44

Preparation of Compound II-35 and II-36

Following the general SPS procedure as described in Example 8, (50a) (500 mg) was reacted with 5-chloro-(1-pivalyl)-pentan-2-one [see preparation of II-20, above] and the crude product purified and the individual diastereomers were separated via semi-preparative HPLC (C-8 reverse phase column, eluted with 60% MeCN in water containing 0.1% TFA). Minor isomer (HPLC: R$_t$=33.7 min.) and major isomer (HPLC: R$_t$=35.23 min.) (Method A). MS: 495 (M+H). A small amount of the R18=Et analog II-32 (HPLC: R$_t$=37.0 min) was also isolated.

The minor isomer (3.7 mg) in THF (1 mL) was treated with a solution of LiBH$_4$ (0.5 mL, 2M) and stirred at room temperature overnight. The reaction mixture was extracted with EtOAc, the organic layer was washed with 1N NaOH solution, brine and dried over anhydrous MgSO$_4$. Following filtration and solvent removal by rotary evaporation, the alcohol II-35 (2.4 mg) was isolated which had the following physical properties: HPLC: R$_t$=25.2 min. (Method A). MS: 411 (M+H).

The major isomer (39.5 mg) in THF (2 mL) was treated with a solution of LiBH$_4$ (2 mL, 2M) and stirred at room temperature overnight. The reaction mixture was extracted with EtOAc, the organic layer was washed with 1N NaOH solution, brine and dried over anhydrous MgSO$_4$. Following filtration and solvent removal by rotary evaporation, the alcohol II-36 (27.3 mg) was isolated which had the following physical properties: HPLC: R$_t$=23.7 min. (Method A). MS: 411 (M+H).

Example 45

Preparation of Compound II-37

Following the general SPS procedure as described in Example 8, (50a) (25 mg) was reacted with 5-chloro-pentan-2-one to provide 2.3 mg of the desired product as a mixture of diastereomers which had the following physical properties: HPLC: R$_t$=32.2 min, and 33.2 min. (Method A). MS: 395 (M+H).

Example 46

Preparation of Compound II-38

Following the general SPS procedure as described in Example 8, (50a) (50 mg) was reacted with diethoxybutyraldehyde [similar to procedure described for II-23]. The crude product following TFA treatment was purified by C-8 reverse phase column chromatography, and underwent hydrolysis upon sitting in the HPLC solvent [55% MeCN-45% water w/0.1% TFA]. Solvent was removed via rotary evaporation to provide a product which had HPLC: R$_t$=22.3 min. (Method A). MS: 397 (M+H).

Example 47

Preparation of Compound II-39

To a stirred suspension of (47a) (87 mg, 0.280 mmol) in acetonitrile (20 mL) at room temperature under nitrogen was added 2-chloromethylcyclobutanone (39.9 mg, 0.336 mmol) followed by DBU (46.1 mL, 0.308 mmol). The reaction mixture was heated to reflux for 42 h. DMF was added to solubilize the reaction mixture and 2-chloromethylcyclobutanone (1 eq.) was added and the mixture heated to reflux for 30 min. An additional 1 eq. of 2-chloromethylcyclobutanone was added and the reaction mixture heated to reflux overnight, cooled to room temperature, diluted with ethyl acetate (50 mL) then washed with water (4×25 mL). The organic layer was dried (MgSO$_4$), filtered and concentrated in vacuo to yield a thin film, which upon further drying solidified (90 mg, 82% yield). MS (ES$^+$): m/e 415 (M+Na)$^+$; $^1$H NMR (CDCl$_3$, 300 MHz): δ 1.93 (m, 1H), 2.28 (m, 1H), 3.09 (dd, 2H), 3.74 (m, 4H), 3.88 (m, 1H), 4.46 (d, 1H, J=17.1), 4.68 (d, 1H, J=17.1), 7.21–0.7.48 (m, 6H), 7.63 (d, 1H), 8.43 (s, 1H), 9.35 (1H, d).

Example 48

Preparation of Compound II-40a and II-40b

The reaction was carried out as described for II-38, except the crude product (after cleavage from resin) was purified via column chromatography on silica gel (2:1 toluene/EtOAc). Two isomeric ethyl acetals, II-40a and II-40b, were isolated and had the following physical properties: HPLC R$_t$=32.3 and 30.4 min., respectively (Method A). MS: 425 (M+H).

Example 49

Preparation of Compound II-41

To a stirred solution of II-39 (63 mg, 0.161 mmol) in THF (8 mL) under nitrogen at 0° C. was added lithium borohydride (96 mL, 0.193 mmol) dropwise. The reaction was stirred at 0° C. for 30 min. then warmed to room temperature for 2 h. The reaction was cooled to 0° C. and quenched with methanol. The mixture was stirred for 30 min. at room temperature. The solvent was removed in vacuo leaving an off-white solid. The product was isolated by flash chromatography on silica gel using EtOAc (100%) to give a white residue (5 mg, 8% yield). MS (ES$^+$): m/e 394 (M+H); $^1$H NMR (CDCl$_3$, 300 MHz): δ 2.34 (m, 2H), 3.43 (m, 1H), 3.60 (dd, 1H), 3.83 (dd, 1H), 3.89 (s, 2H), 3.98 (d, 2H), 4.26–4.34 (m, 2H), 4.75 (s, 2H), 7.31–7.60 (m, 6H), 7.72 (d, 1H), 8.54 (s, 1H), 9.38 (dd, 1H).

Example 50

Preparation of Compound II-42

Following the general SPS procedure as described in Example 8, (50a) (50 mg) was reacted with γ-lactone to provide 4.5 mg of the desired product which had the following physical properties: HPLC: R$_t$=14.1 min, (mixture of diastereomers) (Method C). MS: 379 (M–OH)$^+$.

Example 51

Preparation of Compound II-43

Following the general SPS procedure as described in Example 8, (50a) (50 mg) was reacted with 3,4-oxo-tetrahydrofuran [which was prepared according to the literature procedure of Hawkins et.al. *J. Chem. Soc.* 1959, 248] and the crude product was purified by semi-preparative HPLC to provide 1 mg of the desired compound which had the following physical properties: HPLC: $R_t$=14.7 min, (mixture of diastereomers) (Method C). MS: 395 (M+H).

Example 52

Preparation of Compound II-44

Following the general SPS procedure as described in Example 8, (50a) (50 mg) was reacted with 1,5-dichloropentan-2-one [which was prepared according to the literature procedure of L. Hart et.al. *J. Org. Chem.* 1959, 24, 1261] to provide 6.5 mg of chloromethyltetrahydrofuran derivative II-44 as a mixture of diastereomers which had the following physical properties: HPLC: $R_t$=15.3 min, (mixture of diastereomers) (Method C). MS: 429 (M+H).

Example 53

Preparation of Compound II-45a, II-45b and II-46

Following the general SPS procedure as described in Example 8, (50a) (50 mg) was reacted with 2-formyl-3,5-dimethoxy-benzyl chloride [which was prepared according to the literature procedure of G. M. Makara et.al.. *J. Org. Chem.* 1995, 60, 717] to provide a crude product which was purified (and the diastereomers were separated) by semi-preparative HPLC to yield indivisual diastereomers II-45a (6.8 mg) and II-45b (5.9 mg) respectively. These product had the following physical properties: .HPLC: $R_t$=13.8 min (II-45a) and 15.9 min (II-45b) (Method C). MS: 511 (M+Na).

In addition, an ethyl transfer product, II-46 (R18=Et analog), was also isolated and had the following physical properties: HPLC: $R_t$=15.0 min (Method C). MS: 539 (M+Na).

Example 54

Preparation of Compound II-47

Following the general SPS procedure as described in Example 8, (50a) (50 mg) was reacted with 3,3-dimethyl-4-oxo-γ-lactone to provide 10.1 mg of the desired product as a mixture of diastereomers which had the following physical properties: HPLC: $R_t$=13.2 min. and 14.3 min, (Method C). MS: 439 (M+H)$^+$.

Example 55

Preparation of Compound II-48

Following the general SPS procedure as described in Example 8, (50a) (50 mg) was reacted with 2,3-O-isopropylidene-D-erythronolactone to provide 4.1 mg of the desired product as a mixture of diastereomers which had the following physical properties: HPLC: $R_t$=12.9 min. and 13.6 min, (Method C). MS: 469 (M+H)$^+$.

Example 56

Preparation of Compound II-49

Following the general SPS procedure as described in Example 8, (50a) (125 mg) was reacted with 3-formyl-N,N-dimethylpropionamide and 20 mg of the hydroxy amide intermediate was isolated in the usual manner from the solid-phase reaction. This alcohol (10 mg) was oxidized with Dess-Martin periodinane (105 mg) in dichloromethane (5 mL) at 0° C. for 30 min. The reaction mixture was washed with aq. $Na_2S_2O_3$, aq. $NaHCO_3$, and brine, and dried over anhydrous $MgSO_4$ before filtration and concentration in vacuo. The resulting keto-amide was taken up in methanol (5 mL) and hydrazine hydrate (1 mL) was added and the mixture was heated to reflux for 2 h. After the solvent was removed in vacuo, the residue was taken up in $CH_2Cl_2$ and washed with water, brine, and dried over anhydrous $MgSO_4$. After filtration and solvent removal by rotary evaporation, 4.9 mg of the desired product, II-49 was obtained which had the following physical properties: HPLC: $R_t$=10.3 min. (Method C). MS: 407 (M+H)$^+$.

Example 57

Preparation of Compound II-50

Following the general SPS procedure as described in Example 8, (50a) (50 mg) was reacted with 1,4-dioxaspiro [4,5] decan-one to provide 4.1 mg of the desired product as a mixture of diastereomers which had the following physical properties: HPLC: $R_t$=14.0 min. (Method C). MS: 409 (M+H).

Example 58

Preparation of Compound II-51 a, II-51bc, II-51d

Preparation of (1,1-Diethoxyethoxy)Acetone

To a cold (0° C.) suspension of NaH (2.68 g, 60%) in THF (150 mL) was added a solution of 1,1-diethoxyethanol [which was prepared according to the literature procedure of Zirkle, C. L. et. al. *J. Org. Chem.* 1961, 26, 395–407] (9.00 g) in THF (20 mL), and the reaction mixture was stirred at room temperature for 1 hour before adding methallyl chloride (8.0 mL). The reaction mixture was heated to reflux overnight, cooled and filtered through a plug of celite. Solvent was removed by rotary evaporation, and the residue purified by column chromatography (silica, 20% ether/hexane) to give 1,1-diethoxyethylmethallyl ether (11.5, 90%). Ozonolysis of a chilled (−30° C.) solution of this ether (6.00 g) in EtOAc (80 mL) was carried out until no starting material was detectable by TLC (1 hour). At this time, the reaction was purged with oxygen, treated with Pd(OH)$_2$ (150 mg) and stirred under an atmosphere of hydrogen overnight. The catalyst was filtered away, and the filtrate was concentrated by rotary evaporation. The resulting residue was purified by column chromatography (silica, 20% EtOAc/hexane) to afford (1,1-diethoxy-ethoxy)acetone (4.53 g, 82%).

Following the general SPS procedure as described in Example 8, (50a) (50 mg) was reacted with (1,1-diethoxyethoxy)acetone [as described above]. A portion of the product (6.5 mg) was fractionated by semi-preparative HPLC (C-8 reverse phase, and eluted with 65% MeCN-water containing 0.1% TFA). The isomeric products isolated were:

II-51a (0.53 mg, HPLC: $R_t$=15.0 min.) MS: 455 (M+H), II-51bc (1.25 mg, HPLC: $R_t$=15.3 min and 15.4 min.) MS: 477 (M+Na) and II-51d (1.31 mg, HPLC: $R_t$=15.8 min.) (Method C) MS: 477 (M+Na).

Example 59

Preparation of Compound II-52

The crude reaction products (10.5 mg), obtained according to the preparation of II-40a and II-40b, were taken up in methylene chloride (20 mL) and treated with $BF_3$ etherate (20 μL). After stirring for 2.5 hours, the solution was washed with saturated aqueous $NaHCO_3$ and brine prior to drying over $MgSO_4$. After filtration and solvent removal by rotary evaporation, the residue was taken in THF (2 mL) and treated with NBS (4.5 mg). After stirring overnight additional NBS (4.5 mg) was added and the reaction stirred for another 2.5 h. The crude product was filtered thru a short C-18 column (SEP-PAK cartridge) and eluted with a 5% incremental step gradients of 65% –75% MeCN-water containing 0.1% TFA. The appropriate fractions were pooled, neutralized with aq. $NaHCO_3$ and extracted with $CH_2Cl_2$ and dried over anhydrous $MgSO_4$. After filtration and solvent removal by rotary evaporation provided a mixture of bromides (5 mg). To the mixtures of the bromides (5 mg) in methoxyethanol (2 mL) was added $Et_3N$ (37 μL) and $PdCl_2(Ph_3P)_2$ (1.5 mg), and the mixture was heated in carbon monoxide atmosphere for 30 min. The reaction mixture was cooled and extracted with EtOAc, and organic layer washed with water. The aqueous layer was extracted several times with EtOAc, and the combined organic layers were washed with brine, aq. $NaHCO_3$, 1N HCl, and brine, and dried over $MgSO_4$. Filtration and concentration in vacuo yielded=1.1 mg of II-52 as a mixture of diastereomers. HPLC: $R_t$=13.97 min. and 14.12 min. (Method C). MS: 557 (M+H), 579 (M+Na).

Example 60

Preparation of Compound II-53

Following the general SPS procedure as described in Example 8, (50a) (50 mg) was reacted with 5-chloro-(1-pivalyl)-pentan-2-one [as described above for II-20] and the major product, a single diastereomer, was isolated via semi-preparative HPLC (C-8 reverse phase column, eluted with 75% MeCN in water containing 0.1% TFA). HPLC: $R_t$=17.2 min. (Method A).

The pivalate (5 mg) in THF (2 mL) was treated with a solution of $LiBH_4$ (2 mL, 2 M) and the reaction mixture was stirred at room temperature overnight. Reaction mixture was quenched with 1N HCl and extracted with EtOAc. The organic layer was washed with 1N NaOH soln., brine and dried over anhydrous $MgSO_4$. Filtration and concentration in vacuo provided the alcohol II-53 (3.2 mg). HPLC: $R_t$=12.0 min. (Method A). MS: 441 (M+H).

Example 61

Preparation of Compound II-54

Following the general SPS procedure as described in Example 8, (50a) (50 mg) was reacted with diethoxybutyraldehyde. This experiment protocol is similar to that used for the preparation of compounds II-23, II-40a and II-40b, as described above. The crude product (following TFA treatment) was purified by C-8 reverse phase column chromatography, the appropriate fractions were pooled and neutralized with solid $NaHCO_3$ before being extracted into EtOAc. The organic layer was washed with brine and dried over $MgSO_4$, filtered and concentrated in vacuo to yield=17.2 mg. HPLC $R_t$=14.8 min. (Method C). MS: 455 (M+H).

Example 62

Preparation of Compound II-55a and II-55b

Following the general SPS procedure as described in Example 8, (50a) (145 mg) was reacted with 2-ethoxycarbonyl-2-cyclopentenone [which was prepared according to the literature procedure of H. J. Reich et. al. *J. Am. Chem. Soc.* 1975, 97, 5434–47]. The crude product was purified by semi-preparative HPLC (C8, 65% $CH_3CN$-35% water containing 0.1% TFA) to give II-55a (1.98 mg) HPLC: $R_t$=12.1 min. (Method C). MS: 465 (M+H) and II-55b (7.35 mg) HPLC: $R_t$=14.1 min. and 15.6 min.(Method C). MS: 465 (M+H).

Example 63

Preparation of Compound II-56

A sample from example II-55a (7 mg) was treated with sodium cyanide in DMSO at (145° C.) for 1 h to yield the imide derivative II-56. Yield: (4.93 mg). HPLC: $R_t$=13.6 min. (Method C). MS: 519.

Example 64

Preparation of Compound II-57

To a THF solution (10 mL) of II-01a (200 mg, 0.54 mmol) was added NBS (116 mg, 0.65 mmol). The reaction was stirred at room temperature for 24 h. Solvent was removed via rotary evaporation and the remaining brown solid was stirred with methanol (5 mL) for 0.5 h. The suspension was filtered and washed with methanol leaving 215 mg (0.48 mmol, 89%) of the desired product which had the following spectral properties: 300 MHz $^1$H NMR (DMSO $d_6$) δ 9.52 (d, 1), 8.65 (s, 1), 8.621 (s, 1), 8.15 (s, 1), 7.78–7.62 (m, 2), 7.44–7.38 (m, 2), 5.20 (m, 1), 4.95 (s, 2), 4.74 (dd, 1), 4.50 (s, 2), 3.53 (m, 1), 2.8 (t, 1), 2.48 (m, 1).

Example 65

Preparation of Compound II-58

To a suspension of (47a) (1 g, 3.2 mmol) in THF (40 mL) was added NBS (632 mg, 3.5 mmol). The reaction was stirred at room temperature for 18 h. The solvent was removed under vacuum and the resultant yellow-orange solid was suspended in methanol (50 mL). The slurry was filtered and the solid washed with more methanol. After drying, the bromo compound (R3=Br) (1.09 g, 2.8 mmol, 88% yield) was recovered as a pale yellow solid: (ESI (M+H) 388.2, 390.2 m/e).

To a solution of the above bromide (1.09 g, 2.8 mmol) was added 4,4'-dimethoxybenzhydrol (818 mg, 3.4 mmol) and p-toluenesulfonic acid (532 mg, 2.8 mmol) in benzene (60 mL) and N-methylpyrrolidinone (6 mL) were heated to reflux. After 24 h the reaction was allowed to cool to room temperature and diluted with ethyl acetate (200 mL). The organic layer was washed with $NaHCO_3$ (2×), $H_2O$ (2×), and Brine(2x), dried over anhydrous MgSO$_4$, filtered and the solvent removed in vacuo. The crude material was purified via column chromatography (10% EtOAc-Hexane) to provide the desired DMB protected 3-bromoindole derivative (1.5 g, 2.4 mmol, 87% yield) as an orange solid: (ESII-MS (M+H) 616.5 m/e).

A 250 mL sealable tube was charged with the DMB protected 3-bromo compound (1.5 g, 2.4 mmol), bis(triphenylphosphinyl)palladium dichloride (100 mg, 0.14 mmol), anhydrous sodium acetate (3.9 g, 4.8 mmol), and methoxyethanol (50 mL). The tube was alternately evacuated and filled with CO, leaving it under an atmosphere of CO. It was then lowered into an oil bath at 150° C. After 4 h the tube was cooled to room temperature and recharged with CO. This was repeated once more with the reaction going a total of 10 h. The reaction was diluted with ethyl acetate (250 mL), washed with water, dried over anhydrous MgSO$_4$, filtered and dried in vacuo. The residue was triturated with methanol to give the 3-carboxy compound (1.29 g, 2.02 mmol, 84% yield) as a yellow solid: ESII-MS (M+H) 639.6 m/e.

To a solution of the above ester (1.2 g, 1.9 mmol) in of methylene chloride (20 mL) was added thioanisole (1 mL) followed by TFA (4 mL). After stirring for 1 h at room temperature, the reaction mixture was evaporated to dryness and the residue was suspended in diethylether. The suspension was filtered and the solid was washed with diethylether until the filtrate was colorless. The deprotected ester (636 mg, 1.54 mmol) was isolated as an off-white solid (ESII-MS (M+H) 413.4 m/e.

The above ester (500 mg, 1.2 mmol) was suspended in methylene chloride (15 mL) and a solution of diisobutylaluminumhydride in methylene chloride (5.5 mL, 5.5 mmol, 1.0 M) was added. After 2 h at room temperature the reaction was quenched with methanol. Solvent was removed by rotary evaporation and water was added to the residue. The slurry was filtered and the solid allowed to dry. The desired product [A$_1$,A$_2$=H$_2$, B$_1$,B$_2$=O, R3=CH$_2$OH, R4=R5=R6=H, Q=NH] (367 mg, 1.08 mmol) was obtained as a pale yellow solid: ESII-MS (M+H) 341.3 m/e.

To a suspension of the above alcohol (430 mg, 1.2 mmol) in 2-methoxyethylalcohol (25 mL), in a sealable tube was added trifluoroacetic anhydride (340 µL, 2.4 mmol). The reaction mixture was heat at 70° C. for 15 h. The tube was cooled and water was added to the reaction vessel. After stirring for 1 h the suspension was filtered providing the desired ether [A$_1$,A$_2$=H$_2$, B$_1$,B$_2$=O, R3=CH$_2$OCH$_2$CH$_2$OCH$_3$, R4=R5=R6=H, Q=NH] (370 mg, 0.93 mmol, 77% yield) as an orange solid: ESII-MS (M+H) 399.5 m/e.

The above ether (370 mg, 0.93 mmol) was dissolved in DMF (20 mL). The solvent was reduced in vacuo to ~50% (30 mmHg). Sodium hydride (45 mg, 0.93 mmol of a 60% dispersion in mineral oil) was added in one portion and the reaction was stirred for 1 h at room temperature. Glycidil mesylate (170 mg, 1.1 mmol) was then added and the reaction was stirred an additional 18 h at 60° C. The crude reaction mixture was stirred at room temperature for 4 h, filtered and concentrated. Column chromatography (50% EtOAc-hexane to 10% MeOH-EtOAc) provided the desired product II-58 (90 mg, 0.2 mmol, 22%). 300 MHz $^1$H NMR (DMSO d$_6$) δ 9.50 (d, 1), 8.60 (s, 1), 7.95 (s, 1), 7.80–7.31 (m, 5), 5.18 (m, 1), 4.90 (s, 2), 4.74 (dd, 1), 4.65 (s, 2), 4.50 (s, 2), 3.62 (d, 2), 3.53 (m, 1), 3.50 (d, 2), 3.25 (s, 3), 2.8 (t, 1), 2.48 (m, 1).

Example 66

Preparation of Compound II-59 [FIG. 16]

To a well stirred solution of (49a) (1.4 g, 4.1 mmol) in 260 mL of benzene was added MnO$_2$ (2.16 g, 24.8 mmol) and the mixture was heated to reflux for 18 h. The hot reaction mixture was filtered through a pad of celite, washed with hot THF (5x20 mL) and the filtrate was concentrated in vacuo. The crude product was triturated with MeOH, filtered, washed with cold MeOH and dried to obtain the indanone derivative (68a) (1.13 g, 85% yield). HPLC (Method C) Rt=17.24 min.

To a magnetically stirred suspension of (68a) (0.05 g, 0.09 mmol) in anhydrous THF (10 mL) was added cyclopentylmagnesium bromide (2M solution in Et$_2$O), (0.079 g, 5 mmol) at 0° C. under argon atmosphere. After 15 min., the reaction mixture was quenched with saturated aqueous NH$_4$Cl solution and the phases were separated. The aqueous phase was extracted with EtOAc (3x7 mL), the combined organic extracts were washed with water and brine, dried over MgSO$_4$ and concentrated in vacuo to afford the addition product. HPLC (Method C) Rt=17.36 min.; MS=621 (M+H); 643 (M+Na).

To a well stirred solution of the product (0.035 g, 0.056 mmol) in a mixture of CH$_2$Cl$_2$ (10 mL) and Et$_3$SiH (6 mL) was added trifluoroacetic acid (1 mL) at room temperature. After 1 h, the reaction mixture was concentrated in vacuo to furnish the crude product. Purification of the crude product by flash chromatography on silica gel afforded II-59 (9.1 mg, 42% yield). HPLC (Method C) Rt=15.96 min.; MS: 379 (M+H).

Example 67

Preparation of Compound II-60 [FIG. 16]

To a magnetically stirred solution of lithium bis(trimethylsilyl)amide (1M solution in THF), (0.21 mL, 1.26 mmol) in anhydrous THF (5 mL) was added γ-butyrolactone (100 mg, 1.26 mmol) at −78° C. under argon atmosphere. After stirring for 45 min at −78° C., the. solution of the enolate was transferred via a cannula to a solution of (68a) (70 mg, 0.12 mmol) in anhydrous THF (5 mL) at −78° C. Following the addition of the enolate solution, the temperature of the reaction was raised to 0° C. over a period of 2 h. The cold 0° C. reaction mixture was quenched with saturated aqueous NH$_4$Cl solution, and the phases were separated. The aqueous phase was extracted with EtOAc (3x25 mL), and the combined organic extracts were washed with water, brine, dried over MgSO$_4$ and concentrated in vacuo to give the crude product. The crude product was triturated with EtOAc, filtered and washed with EtOAc. Purification of the solid by flash chromatography on silica gel gave the addition product (16 mg, 18% yield). HPLC (Method C) Rt=15.47 min.; MS: 637 (M+H), 659 (M+Na)

To a well stirred solution of above product (15 mg, 0.023 mmol) in a mixture of CH$_2$Cl$_2$ (5 mL) and Et$_3$SiH (5 mL) was added trifluoroacetic acid (0.6 mL) at room temperature. After 1 h, the reaction mixture was concentrated in vacuo to yield the crude product. The crude product was repeatedly evaporated from EtOAc (3x10 mL). The crude product was titurated with hexane and the solid was filtered and washed with hexane, and dried to provide II-60 (9 mg, 100% yield). HPLC (Method C) Rt=11.00 min.; MS: Obs: 433 (M+K).

Example 68

Preparation of Compound II-61

The alcohol [$A_1,A_2$=$H_2$, $B_1,B_2$=O, R3=$CH_2OH$, R4=R5=R6=H, Q=NH] intermediate described for the synthesis of compound II-58, (360 mg, 0.9 mmol) was placed in a sealable tube with ethanol (15 mL). To this suspension was added trifluoroacetic anhydride (254 µL, 1.8 mmol). The reaction was heat at 70° C. for 15 h. The tube was cooled and the contents transferred to an RB-flask. The solvent was evaporated and the solid was triturated with methanol to provide the desired ether (239 mg, 0.65 mmol, 72% yield) as an orange solid. (ESII-MS (M+H) 369.3 m/e).

Compound II-61 was prepared using the same procedure as described above for II-58 using the ether [$A_1A_2$=$H_2$, $B_1,B_2$=O, R3=$CH_2OCH_2CH_3$, R4=R5=R6=H, Q=NH] (122 mg, 0.33 mmol), NaH (16 mg, 0.33 mmol), and glycidil mesylate (76 mg, 0.5 mmol) in DMF (10 mL). A total of 103 mg (0.24 mmol, 73%) of desired product was obtained which had the following spectral properties: 300 MHz $^1$H NMR (DMSO $d_6$) δ 9.52 (d, 1), 8.60 (s, 1), 8.60 (s, 1), 7.96 (s, 1), 7.78–7.62 (m, 2), 7.44–7.38 (m, 2), 5.20 (m, 1), 4.95 (s, 2), 4.78 (dd, 1), 4.62 (s, 2), 4.5 (s, 2), 3.54 (q, 2), 3.52 (t, 2), 2.78 (t, 1), 2.48 (m, 1), 1.20 (t, 3).

Example 69

Preparation of Compound II-62

To a solution of (47a) (290 mg, 0.94 mmol) in dry DMF (15 mL) was added sodium hydride (45 mg, 0.94 mmol of a 60% dispersion in mineral oil) in one portion. After stirring at RT for 1 h, 2-tetrahydrofurfuryl mesylate (200 mg, 1.1 mmol) was added and the reaction stirred for 24 h at room temperature. The reaction was heated to 60° C. (oil bath temperature) for 24 h and then stirred at room temperature for 72 h. The reaction was filtered and the precipitate was washed with diethyl ether. The solvents were concentrated and the residue was triturated with 1:1 diethyl ether/methanol and the solid was collected. The resultant tan solid was purified by column chromatography (20% EtOAc—$CH_2Cl_2$) to give the desired product (140 mg): mp >250° C., $^1$H NMR (300 MHz, DMSO-$d_6$) δ 9.52 (d, 1), 8.58 (s, 1), 8.01 (d, 1), 7.76 (d, 1), 7.68 (d, 1), 7.50 (dd, 1), 7.44–7.31 (m, 3), 4.95 (m, 1), 4.80 (m, 2), 4.50 (s, 2), 4.23 (m, 2) 3.75 (q, 1), 3.56 (q, 1), 1.80 (m, 4); MS (ES$^+$) 395(M+1).

Example 70

Preparation of Compound II-63

This compound was prepared by essentially the same procedure as described for II-62 from (47a) (280 mg, 0.9 mmol), sodium hydride (60% dispersion in mineral oil) (42 mg, 0.9 mmol) and 2-tetrahydrofurfuryl mesylate (200 mg, 1.1 mmol). Additional NaH (10 mg) and mesylate (50 mg) were added after 72 h at room temperature and the reaction was heated to 100° C. for 24 h. The crude mixture was filtered, and the precipitate was washed with DMF. The solvents were concentrated and the resulting solid triturated with methanol and collected. The crude product was purified by HPLC (60% $CH_3CN$—$H_2O$ 0.1% TFA) to give the desired product: mp >250° C., $^1$H NMR (300 MHz, DMSO-$d_6$) δ 9.54 (d, 1), 8.61 (s, 1), 8.05 (d, 1), 7.80 (d, 1), 7.70 (d, 1), 7.58 (dd, 1), 7.44–7.31 (m, 3), 4.95 (m, 1), 4.75 (m, 2), 4.56 (s, 2), 4.00 (m, 2) 3.6 (m, 2), 1.95 (m, 1), 1.80 (m, 2); ESI MS (ES$^+$) 395 (M+1).

Example 71

Preparation of Compound II-64

Following the general SPS procedure as described in Example 8, (50a) (50 mg) was reacted with sorbic aldehyde, except the resin was not treated with TFA, to provide the resin bound aldol product (50d). To a suspension of 4-Phenyl-1,2,4-triazoline-3,5-dione (100 mg, 0.57 mmol) in 1 mL of tetrahydrofaran: dichloromethane (1:1) at −60° C., was added the resin (50d) (0.025 mmol). The reaction mixture was stirred for in cold bath for 1 h; the cooling bath was removed and the mixture was stirred at room temperature for additional 0.5 h. The resin was filtered and worked up as described in Example 8, to provide compound II-64, [crystalline solid (15 mg)], as a mixture of diastereomers. HPLC (Method D) Rt=24.9, 25.7, 26.4, 27.6, 28.2, 28.6, 29.2 min.; MS: 582 (M+H).

Example 72

Preparation of Compound II-65

To the resin (50a) (50 mg, 0.025 mmol) in 0.25 mL anhydrous tetrahydrofuran under argon was added a 1.0 M solution of ethylmagnesium bromide (0.8 mL, 0.8 mmol) in tetrahydrofuran at room temperature. The reaction mixture was agitated gently with magnetic stirring for 45 min. Hexamethylphosphoramide (1.0 mL) was added by syringe over one minute and stirring was continued for additional 10 min. (Bromomethyl)cyclopropane (1.0 mL, large excess) was added by syringe in one portion and the reaction was stirred for 3 h. The reaction was then heated to reflux for 16 h. The reaction was quenced by the addition of saturated ammonium chloride solution (5 mL). The resin was removed from the supernatant by filtration onto filter paper (Coors funnel) and was washed successively with (3×10 mL portion of) water, N,N-dimethylformamide, tetrahydrofuran, isopropanol, ethyl ether, and dichloromethane. The resulting resin was permitted to dry briefly in the air stream and was then transferred to a round bottom flask and treated with a 1% solution of trifluoroacetic acid in dichloromethane (10 mL) with stirring for one hour. Organics were separated from the spent resin by filtration employing (10 mL) dichloromethane as a chaser. The organics were concentrated; anhydrous toluene (10 mL) was added to the flask and residual water was removed by a second concentration. The solid was dried in vacuo to afford compound II-65, 12 mg as a yellow glass. HPLC (Method D) Rt=25.1 min.; MS: 419 (M+H).

Example 73

Preparation of Compound II-66

Compound (47a) (50 mg, 0.16 mmol) was dissolved in anhydrous N,N-dimethylformamide (10 mL) in a flame dried round bottom flask fitted with a short-path distillation apparatus. Approximately 3 mL of the DMF were removed by distillation at 40° C. employing high vacuum (1–2 mm Hg) to remove any contaminating water. The solution was cooled to room temperature and sodium hydride (7.0 mg, 0.18 mmol, 60% dispersion in mineral oil) was added. The mixture was heated to 50° C. for 30 min. to ensure complete anion generation. 1-Cyano-1-(p-toluenesulfonyloxymethyl) cyclopropane (45 mg, 0.177 mmol) prepared from the tosylation of 1-cyano-1-hydroxymethylcyclopropane (employing p-toluenesulfonic anhydride and pyridine in dichloromethane) was added and heating was continued at 50–60° C. for 18 h. The reaction was quenced by the addition of several drops of water and was concentrated in vacuo. The resulting solid was redissolved in N,N-dimethylformamide (1 mL) and was filtered through a cotton plug. Preparative high performance liquid chromatography on a C8 reverse phase column (55% acetonitrile:water) afforded 6 mg of the desired compound II-66. HPLC (Method C) Rt=13.5 min.; MS: 390 (M+H).

Example 74

Preparation of Compound II-67 (via scheme 20)

A mixture of Compound (47a) (1.5 g, 4.8 mmol), tert-butyl acrylate (1.5 mL, 10 mmol), DBU (11 drops), and tert-butanol (2 mL) in anhydrous acetonitrile (50 mL) was refluxed under argon for 5 days. The reaction mixture was cooled to room temperature and ether (27 mL) was added the reaction mixture was cooled to 0° C., filtered, washed with ether (3×10 mL), and dried to provide the Micheal addition product (96a) [$R^{18}$=$R^{23}$=H, R'=tert-Butyl], (1.55 g, 73% Yield). HPLC (method D): Rt: 31.54.

To a well stirred suspension of the tert-butyl ester (96a) (1.55 g, 3.5 mmol) in 2 mL of methylene chloride was added trifluoroacetic acid (15 mL) at room temperature. The mixture was further stirred for 1 h at room temperature and TFA and methylene chloride were removed under vacuum and azeotrophed with toluene (3×15 mL) and dried under vacuum to obtain the acid (97a) [$R^{18}$=$R^{23}$=H], (1.4 g, 99% Yield). HPLC (method D): Rt=22.89 min.

To a well stirred mixture of BOP (0.165 g, 0.37 mmol), HOBt (0.040 g, 0.029 mmol) in DMF (8 mL) was cooled to 5° C., $Et_3N$ (24 drops) and the acid (97a) (0.1 g, 0.26 mmol) were added. The resulted mixture was further stirred at 5° C. for 30 min., then benzyl mercaptan (15 drops) was added. The reaction mixture was further stirred at room temperature for 15 h and quenched with water (50 mL). The solid was filtered, washed with water (3×10 mL), and dried to provide the thio-ester (98a) [$R^{18}$=$R^{23}$=H, R"=Bn], (0.145 g, 99% Yield), HPLC (method D): Rt=32.22 min. MS: 489 (M+H) and 511 (M+Na).

To a well stirred solution of the thio-ester (98a) (40 mg, 0.081 mmol) in a mixture of NMP (6 mL) and acetone (6 mL) were added Pd/C (10%), (100 mg) and $Et_3SiH$ (1 mL). The reaction mixture was heated to 55° C. for 45 min., filtered from a pad of celite, and washed with acetone and the filtrate was concentrated to give crude aldehyde (99a) [$R^{18}$=$R^{23}$=H] (10 mg, 33% Yield), HPLC (method D): Rt=23.50 min. The crude aldehyde (99a) was used directly for the next reaction. To a well stirred mixture of aldehyde (99a) (10 mg, 0.027 mmol) and cysteine methyl ester hydrochloride (20 mg, 0.116 mmol) in 1-Methyl-2-pyrrolidinone (3 mL) was added triethylamine (20 drops) at room temperature. The mixture was stirred at ambient temperature for 24 h, then quenched with 2 M sodium bicarbonate solution (10 mL) and extracted with ethyl acetate (3×7 mL). The combined organic layer was washed with water, brine, dried over anhydrous $Na_2SO_4$ and concentrated in vacuo to provide a crude product, which was purified by semi-Prep-HPLC method to provide compound II-67, 2.6 mg, 16% Yield., 95% purity, HPLC (method D): Rt=23.14 min.; MS: 484 (M+H) and 506 (M+Na).

Example 75

Preparation of Compounds II-68 and II-69

To a solution of II-35 and II-36 (2 mg, mixture of diastereomers) in THF (1 mL) was added ethyl isocyanate (30 μL). After stirring overnight, the mixture was quenched with methanol (1 mL), and solvent removed by evaporation. The resulting residue was purified by preparative TLC ( toluene/EtOAc, 1/1) and two bands were isolated. The least polar band provided compound II-68 [HPLC: $R_t$=17.01 min (method A), MS: 553 (M+H) and 575 (M+Na)] and the polar band provided compound II-69 [HPLC: $R_t$=14.74 min (method A), MS: 482 (M+H) and 520 (M+Na)].

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the Formula I:

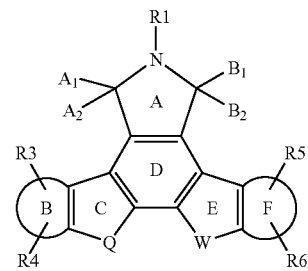

wherein:
ring B and ring F, independently, and each together with the carbon atoms to which they are attached, are selected from the group consisting of:
  a) an unsaturated 6-membered carbocyclic aromatic ring in which from 1 to 3 carbon atoms may be replaced by nitrogen atoms;
  b) an unsaturated 5-membered carbocyclic aromatic ring; and
  c) an unsaturated 5-membered carbocyclic aromatic ring in which either
    1) one carbon atom is replaced with an oxygen, nitrogen, or sulfur atom;
    2) two carbon atoms are replaced with a sulfur and a nitrogen atom, an oxygen and a nitrogen atom, or two nitrogen atoms; or
    3) three carbon atoms are replaced with three nitrogen atoms;

$R^1$ is selected from the group consisting of:
  a) H, substituted or unsubstituted alkyl having from 1 to 4 carbons, substituted or unsubstituted aryl, substituted or unsubstituted arylalkyl, substituted or unsubstituted heteroaryl, or substituted or unsubstituted heteroarylalkyl;
  b) —C(=O)$R^9$, where $R^9$ is selected from the group consisting of alkyl, aryl and heteroaryl;
  c) —O$R^{10}$, where $R^{10}$ is selected from the group consisting of H and alkyl having from 1 to 4 carbons;

d) —C(=O)NH$_2$, —NR$^{11}$R$^{12}$, —(CH$_2$)$_p$NR$^{11}$R$^{12}$, —(CH$_2$)$_p$OR$^{10}$, —O(CH$_2$)$_p$OR$^{10}$ and —O(CH$_2$)$_p$NR$^{11}$R$^{12}$, wherein p is from 1 to 4; and wherein either
  1) R$^{11}$ and R$^{12}$ are each independently selected from the group consisting of H and alkyl having from 1 to 4 carbons; or
  2) R$^{11}$ and R$^{12}$ together form a linking group of the formula —(CH$_2$)$_2$—X$^1$—(CH$_2$)$_2$—, wherein X$^1$ is selected from the group consisting of —O—, —S—, and —CH$_2$—;

R$^2$ is selected from the group consisting of H, alkyl having from 1 to 4 carbons, —OH, alkoxy having from 1 to 4 carbons, —OC(=O)R$^9$, —OC(=O)NR$^{11}$R$^{12}$, —O(CH$_2$)$_p$NR$^{11}$R$^{12}$, —O(CH$_2$)$_p$OR$^{10}$, substituted or unsubstituted arylalkyl having from 6 to 10 carbons, and substituted or unsubstituted heteroarylalkyl;

R$^3$, R$^4$, R$^5$ and R$^6$ are each independently selected from the group consisting of:
  a) H, aryl, heteroaryl, F, Cl, Br, I, —CN, CF$_3$, —NO$_2$, —OH, —OR$^9$, —O(CH$_2$)$_p$NR$^{11}$R$^{12}$, —OC(=O)R$^9$, —OC(=O)NR$^{11}$R$^{12}$, —O(CH$_2$)$_p$OR$^{10}$, —CH$_2$OR$^{10}$, —NR$^{11}$R$^{12}$, —NR$^{10}$S(=O)$_2$R$^9$, —NR$^{10}$C(=O)R$^9$,
  b) —CH$_2$OR$^{14}$, wherein R$^{14}$ is the residue of an amino acid after the hydroxyl group of the carboxyl group is removed;
  c) —NR$^{10}$C(=O)NR$^{11}$R$^{12}$, —CO$_2$R$^2$, —C(=O)R$^2$, —C(=O)NR$^{11}$R$^{12}$, —CH=NOR$^2$, —CH=NR$^9$, —(CH$_2$)$_p$NR$^{11}$R$^{12}$, —(CH$_2$)$_p$NHR$^{14}$, or —CH=NNR$^2$R$^{2A}$ wherein R$^{2A}$ is the same as R$^2$;
  d) —S(O)$_y$R$^2$, —(CH$_2$)$_p$S(O)$_y$R$^9$, —CH$_2$S(O)$_y$R$^{14}$ wherein y is 0, 1 or 2;
  e) alkyl having from 1 to 8 carbons, alkenyl having from 2 to 8 carbons, and alkynyl having 2 to 8 carbons, wherein
    1) each alkyl, alkenyl, or alkynyl group is unsubstituted; or
    2) each alkyl, alkenyl or alkynyl group is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$NR$^{11}$R$^{12}$, —X$^2$(CH$_2$)$_p$C(=O)NR$^{11}$R$^{12}$, —X$^2$(CH$_2$)$_p$OC(=O)NR$^{11}$R$^{12}$, —X$^2$(CH$_2$)$_p$CO$_2$R$^9$, X$^2$(CH$_2$)$_p$S(O)$_y$R$^9$, —X$^2$(CH$_2$)$_p$NR$^{10}$C(=O)NR$^{11}$R$^{12}$, —OC(=O)R$^9$, —OCONHR$^2$, —O-tetrahydropyranyl, —NR$^{11}$R$^{12}$, —NR$^{10}$CO$_2$R$^9$, —NR$^{10}$C(=O)NR$^{11}$R$^{12}$, —NHC(=NH)NH$_2$, NR$^{10}$C(=O)R$^9$, —NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{2A}$, —CH=NOR$^2$, —CH=NR$^9$, —CH=NNHCH(N=NH)NH$_2$, —S(=O)$_2$NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

X$^2$ is O, S, or NR$^{10}$;

R$^7$ is heteroaryl or

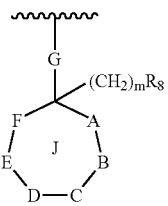

wherein:
m is 0–4;
G is a bond; or alkylene having 1 to 4 carbons, wherein the alkylene group is unsubstituted, or substituted with NR$^{11A}$R$^{12A}$ or OR$^{19}$;
R$^{11A}$ and R$^{12A}$ are the same as R$^{11}$ and R$^{12}$;
R$^{19}$ is selected from the group consisting of H, alkyl, acyl, and C(=O)NR$^{11A}$R$^{12A}$;
R$^8$ is selected from the group consisting of O(C=O)NR$^{11}$R$^{12}$, —CN, acyloxy, alkenyl, —O—CH$_2$—O—(CH$_2$)$_2$—O—CH$_3$, halogen and R$^{14}$ wherein R$^{14}$ is the same as R$^1$;
A and B are independently selected from the group consisting of O, N, S, CHR$^{17}$, C(OH)R$^{17}$, C(=O), and CH$_2$=C; or A and B together can form —CH=CH—;
C and D are independently selected from the group consisting of a bond, O, N, S, CHR$^{17}$, C(OH)R$^{17}$, C(=O) and CH$_2$=C;
E and F are independently selected from the group consisting of a bond, O, N, S, C(=O), and CH(R$^{17}$);
R$^{17}$ is selected from the group consisting of H, substituted or unsubstituted alkyl, alkoxycarbonyl, and substituted or unsubstituted alkoxy;
wherein:
  1) ring J contains 0 to 3 ring heteroatoms;
  2) any two adjacent hydroxyl groups of ring J can be joined in a dioxolane ring;
  3) any two adjacent ring carbon atoms of ring J can be joined to form a fused aryl or heteroaryl ring;
  4) any two adjacent ring nitrogen atoms of ring J can be joined to form a fused heterocyclic ring which can be substituted with 1 to 3 alkyl or aryl groups;
provided that:
  1) one of A, B, C, D, E, or F contains at least one carbon atom that is saturated;
  2) ring J not contain two adjacent ring O atoms;
  3) ring J contains a maximum of two ring C(=O) groups;
Q is selected from the group consisting of O, S, NR$^{13}$, NR$^{7A}$ wherein R$^{7A}$ is the same as R$^7$, CHR$^{15}$, X$^3$CH(R$^{15}$), and CH(R$^{15}$)X$^3$, wherein X$^3$ is selected from the group consisting of —O—, —S—, —CH$_2$—, NR$^{7A}$, and NR$^{13}$;
W is selected from the group consisting of CR$^{18}$R$^7$ and CHR$^2$;
R$^{13}$ is selected from the group consisting of H, —SO$_2$R$^9$, —CO$_2$R$^9$, —C(=O)R$^9$, —C(=O)NR$^{11}$R$^{12}$, alkyl of 1–8 carbons, alkenyl having 2–8 carbons, and alkynyl having 2–8 carbons; and either
  1) the alkyl, alkenyl, or alkynyl group is unsubstituted; or
  2) the alkyl, alkenyl, or alkynyl group independently is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxyalkylthio, F, Cl, Br, I, —CN, —NO$_2$, —OH, —OR$^9$, —X$^2$(CH$_2$)$_p$NR$^{11}$R$^{12}$, —X$^2$(CH$_2$)$_p$C(=O)NR$^{11}$R$^{12}$, —X$^2$(CH$_2$)$_p$OC(=O)NR$^{11}$R$^{12}$, —X$^2$(CH$_2$)$_p$CO$_2$R$^9$, X$^2$(CH$_2$)$_p$S(O)$_y$R$^9$, —X$^2$(CH$_2$)$_p$NR$^{10}$C(=O) NR$^{11}$R$^{12}$, —OC(=O) R$^9$, —OCONHR$^2$, —O-tetrahydropyranyl, —NR$^{11}$R$^{12}$, —NR$^{10}$CO$_2$R$^9$, —NR$^{10}$C (=O)NR$^{11}$R$^{12}$, —NHC(=NH)NH$_2$, NR$^{10}$C(=O)R$^9$, —NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{2A}$, —CH=NOR$^2$, —CH=NR$^9$, —CH=NNHCH(N=NH)NH$_2$, —S(=O)$_2$NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;

R$^{15}$ is selected from the group consisting of H, OR$^{10}$, SR$^{10}$, R$^{7A}$, and R$^{16}$;

R$^{16}$ is selected from the group consisting of alkyl of 1 to 4 carbons; phenyl; naphthyl; arylalkyl having 7 to 15 carbons, —SO$_2$R$^9$, —CO$_2$R$^9$, —C(=O)R$^9$, alkyl having 1–8 carbons; alkenyl having 2 to 8 carbons, and alkynyl having 2 to 8 carbons, wherein
1) each alkyl, alkenyl, or alkynyl group is unsubstituted; or
2) each alkyl, alkenyl, or alkynyl group is substituted with 1 to 3 groups selected from the group consisting of aryl having from 6 to 10 carbons, heteroaryl, arylalkoxy, heterocycloalkoxy, hydroxyalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$NR$^{11}$R$^{12}$, —X$^2$(CH$_2$)$_p$C(=O)NR$^{11}$R$^{12}$, —X$^2$(CH$_2$)$_p$OC(=O)NR$^{11}$R$^{12}$, —X$^2$(CH$_2$)$_p$CO$_2$R$^9$, X$^2$(CH$_2$)$_p$S(O)$_y$R$^9$, —X$^2$(CH$_2$)$_p$NR$^{10}$C(=O) NR$^{11}$R$^{12}$, —OC(=O)R$^9$, —OCONHR$^2$, —O-tetrahydropyranyl, —NR$^{11}$R$^{12}$, —NR$^{10}$CO$_2$R$^9$, —NR$^{10}$C(=O)NR$^{11}$R$^{12}$, —NHC(=NH)NH$_2$, NR$^{10}$C(=O)R$^9$, —NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{2A}$, —CH=NOR$^2$, —CH=NR$^9$, —CH=NNHCH(N=NH)NH$_2$, —S(=O)$_2$NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from 1 to 4 carbons;

R$^{18}$ is selected from the group consisting of R$^2$, thioalkyl of 1–4 carbons, and halogen;

A$^1$ and A$^2$ are selected from the group consisting of H, H; H, OR$^2$; H, —SR$^2$; H, —N(R$^2$)$_2$; and a group wherein A$^1$ and A$^2$ together form a moiety selected from the group consisting of =O, =S, and =NR$^2$;

B$^1$ and B$^2$ are selected from the group consisting of H, H; H, —OR$^2$; H, —SR$^2$; H, —N(R$^2$)$_2$; and a group wherein B$^1$ and B$^2$ together form a moiety selected from the group consisting of =O, =S, and =NR$^2$; with the proviso that at least one of the pairs A$^1$ and A$^2$, or B$^1$ and B$^2$, form =O;

with the proviso that when Q is NH or NR$^{7A}$, and in any R$^7$ or R$^{7A}$ group m is 0 and G is a bond, R$^8$ is H, and R$^7$ or R$^{7A}$ contains one ring hetero oxygen atom at position A in a 5- or 6-membered ring, then B cannot be CHR$^{17}$ where R$^{17}$ is substituted or unsubstituted alkyl;

with the further proviso that the compound of Formula I contains one R$^7$ or R$^{7A}$ group or both an R$^7$ and R$^{7A}$ group; and with the further proviso that when Q is NR$^{13}$, W is CR$^{18}$R$^7$, rings B and F are phenyl, and A, B, C, and D are selected from the group consisting of O, CHR$^{17}$, C(OH)R$^{17}$, C(=O), and CH$_2$=C, then E and F are not a bond, O, C(=O), or CH(R$^{17}$)).

2. The compound of claim 1 wherein:

A and B are independently selected from the group consisting of O, N, S, CHR$^{17}$, C(OH)R$^{17}$, C(=O), and CH$_2$=C;

R$^{17}$ is selected from the group consisting of H, substituted or unsubstituted alkyl, and substituted or unsubstituted alkoxy; wherein:
1) ring J contains 0 to 3 ring heteroatoms;
2) any two adjacent hydroxyl groups of ring J can be joined in a dioxolane ring;
3) any two adjacent ring carbon atoms of ring J can be joined to form a fused aryl or heteroaryl ring;
provided that:
1) one of A, B, C, D, E, or F contains at least one carbon atom that is saturated;
2) ring J does not contain two adjacent ring O atoms;
3) ring J contains a maximum of two ring C(=O) groups; and R$^8$ is selected from the group consisting of O(C=O) NR$^{11}$R$^{12}$, acyloxy, alkenyl, —O—CH$_2$—O—(CH$_2$)$_2$—O—CH$_3$, halogen and R$^{1A}$ wherein R$^{1A}$ is the same as R$^1$.

3. The compound of claim 2 wherein R$^1$, R$^4$ and R$^6$ are H.

4. The compound of claim 2 wherein one of A$_1$,A$_2$ or B$_1$,B$_2$ is H,H and the other is =O.

5. The compound of claim 3 wherein one of A$_1$,A$_2$ or B$_1$,B$_2$ is H,H and the other is =O.

6. The compound of claim 2 wherein R$^1$, R$^4$, R$^5$, R$^6$ and R$^8$ are H.

7. The compound of claim 2 wherein R$^3$ and R$^5$ are independently selected from the group consisting of H, alkoxy, halogen, alkoxyalkyl, alkoxy-alkoxyalkyl and alkoxy-alkoxycarbonyl.

8. The compound of claim 2 wherein Q is NR$^{13}$ or NR$^{7A}$.

9. The compound of claim 8 wherein Q is NR$^{7A}$.

10. The compound of claim 8 wherein R$^{13}$ is H.

11. The compound of claim 2 wherein W is CH$^2$ or CR$^{18}$R$^7$.

12. The compound of claim 11 wherein W is CR$^{18}$R$^7$.

13. The compound of claim 12 wherein R$^{18}$ is H or lower alkyl.

14. The compound of claim 2 wherein R$^7$ is a 3-, 4-, 5- or 6-membered carbocyclic ring, or a 5- or 6-membered heterocyclic ring which contains one or two ring O, N, or S atoms.

15. The compound of claim 14 wherein R$^7$ is a heterocyclic ring having one ring O, N, or S hetero atom.

16. The compound of claim 15 wherein R$^7$ is a heterocyclic ring which contains one ring O atom.

17. The compound of claim 2 wherein G is a bond or CH$_2$.

18. The compound of claim 2 wherein m is 0 or 1.

19. The compound of claim 2 wherein R$^8$ is H, OH, halogen, ethenyl, acyloxy, alkoxy, substituted or unsubstituted phenyl, substituted or unsubstituted heteroaryl, or hydroxyalkyl.

20. The compound of claim 19 wherein $R^8$ is H or OH.

21. A pharmaceutical composition comprising a compound of claim 1 and a pharmaceutically acceptable carrier.

22. The compound of claim 1 wherein $R^7$ is pyridyl.

23. A compound having the formula:

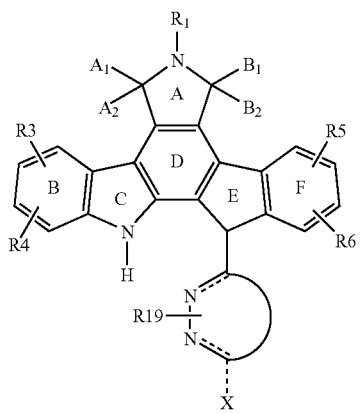

wherein:
  $A^1$ and $A^2$ are selected from the group consisting of H, H; H, $OR^2$; H, $-SR^2$; H, $-N(R^2)_2$; and a group wherein $A^1$ and $A^2$ together form a moiety selected from the group consisting of =O, =S, and =$NR^2$;
  $B^1$ and $B^2$ are selected from the group consisting of H, H; H, $-OR^2$; H, $-SR^2$; H, $-N(R^2)_2$; and a group wherein $B^1$ and $B^2$ together form a moiety selected from the group consisting of =O, =S, and =$NR^2$; with the proviso that at least one of the pairs $A^1$ and $A^2$, or $B^1$ and $B^2$, form =O;
  $R^1$ is selected from the group consisting of:
  a) H, substituted or unsubstituted alkyl having from 1 to 4 carbons, substituted or unsubstituted aryl, substituted or unsubstituted arylalkyl, substituted or unsubstituted heteroaryl, or substituted or unsubstituted heteroarylalkyl;
  b) $-C(=O)R^9$, where $R^9$ is selected from the group consisting of alkyl, aryl and heteroaryl;
  c) $-OR^{10}$, where $R^{10}$ is selected from the group consisting of H and alkyl having from 1 to 4 carbons;
  d) $-C(=O)NH_2$, $-NR^{11}R^{12}$, $-(CH_2)_pNR^{11}R^{12}$, $-(CH_2)_pOR^{10}$, $-O(CH_2)_pOR^{10}$ and $-O(CH_2)_pNR^{11}R^{12}$, wherein p is from 1 to 4; and wherein either
    1) $R^{11}$ and $R^{12}$ are each independently selected from the group consisting of H and alkyl having from 1 to 4 carbons; or
    2) $R^{11}$ and $R^{12}$ together form a linking group of the formula $-(CH_2)_2-X^1-(CH_2)_2-$, wherein $X^1$ is selected from the group consisting of $-O-$, $-S-$, and $-CH_2-$; and
  e) a protecting group or a polymeric support;
  $R^2$ is selected from the group consisting of H, alkyl having from 1 to 4 carbons, $-OH$, alkoxy having from 1 to 4 carbons, $-OC(=O)R^9$, $-OC(=O)NR^{11}R^{12}$, $-O(CH_2)_pNR^{11}R^{12}$, $-O(CH_2)_pOR^{10}$, substituted or unsubstituted arylalkyl having from 6 to 10 carbons, and substituted or unsubstituted heteroarylalkyl;
  $R^3$, $R^4$, $R^5$ and $R^6$ are each independently selected from the group consisting of:
  a) H, aryl, heteroaryl, F, Cl, Br, I, $-CN$, $CF_3$, $-NO_2$, $-OH$, $-OR^9$, $-O(CH_2)_pNR^{11}R^{12}$, $-OC(=O)R^9$, $-OC(=O)NR^{11}R^{12}$, $-O(CH_2)_pOR^{10}$, $-CH_2OR^{10}$, $-NR^{11}R^{12}$, $-NR^{10}S(=O)_2R^9$, $-NR^{10}C(=O)R^9$,
  b) $-CH_2OR^{14}$, wherein $R^{14}$ is the residue of an amino acid after the hydroxyl group of the carboxyl group is removed;
  c) $-NR^{10}C(=O)NR^{11}R^{12}$, $-CO_2R^2$, $-C(=O)R^2$, $-C(=O)NR^{11}R^{12}$, $-CH=NOR^2$, $-CH=NR^9$, $-(CH_2)_pNR^{11}R^{12}$, $-(CH_2)_pNHR^{14}$, or $-CH=NNR^2R^{24}$ wherein $R^{24}$ is the same as $R^2$;
  d) $-S(O)_yR^2$, $-(CH_2)_pS(O)_yR^9$, $-CH_2S(O)_yR^{14}$ wherein y is 0, 1 or 2;
  e) alkyl having from 1 to 8 carbons, alkenyl having from 2 to 8 carbons, and alkynyl having 2 to 8 carbons, wherein
    1) each alkyl, alkenyl, or alkynyl group is unsubstituted; or
    2) each alkyl, alkenyl or alkynyl group is substituted with 1 to 3 groups selected from the group consisting of aryl having from 6 to 10 carbons, heteroaryl, arylalkoxy, heterocycloalkoxy, hydroxylalkoxy, alkyloxy-alkoxy, hydroxyalkylthio, alkoxy-alkylthio, F, Cl, Br, I, $-CN$, $-NO_2$, $-OH$, $-OR^9$, $-X^2(CH_2)_pNR^{11}R^{12}$, $-X^2(CH_2)_p C(=O)NR^{11}R^{12}$, $-X^2(CH_2)_pOC(=O)NR^{11}R^{12}$, $-X^2(CH_2)_pCO_2R^2$, $X^2(CH_2)_pS(O)_yR^9$, $-X^2(CH_2)_pNR^{10}C(=O)NR^{11}R^{12}$, $-OC(=O)R^9$, $-OCONHR^2$, $-O-$tetrahydropyranyl, $-NR^{11}R^{12}$, $-NR^{10}CO_2R^9$, $-NR^{10}C(=O)NR^{11}R^{12}$, $-NHC(=NH)NH_2$, $NR^{10}C(=O)R^9$, $-NR^{10}S(O)_2R^9$, $-S(O)_yR^9$, $-CO_2R^2$, $-C(=O)NR^{11}R^{12}$, $-C(=O)R^2$, $-CH_2OR^{10}$, $-CH=NNR^2R^{24}$, $-CH=NOR^2$, $-CH=NR^9$, $-CH=NNHCH(N=NH)NH_2$, $-S(=O)_2NR^2R^{24}$, $-P(=O)(OR^{10})_2$, $-OR^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;
    $X^2$ is O, S, or $NR^{10}$;
  $R^{19}$ is selected from the group consisting of H, alkyl, acyl, and $C(=O)NR^{11A}R^{12A}$; and
  X is H or O.

24. A compound of claim 23 having the formula:

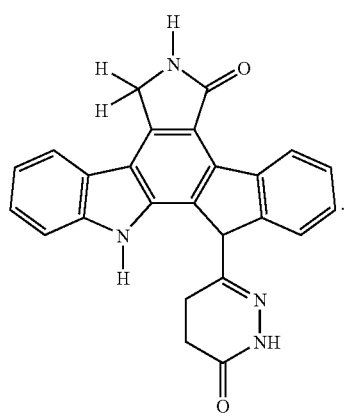

25. A compound having the formula:

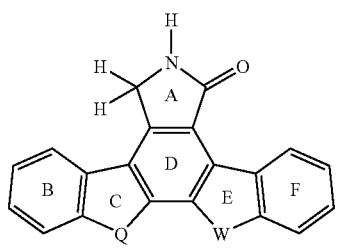

wherein the constituent variables of the compounds of the above formula are selected in accordance with the following table:

| Q | W |
|---|---|
| NH | CH (with HO-CH group attached to a ring system containing N-N bonded cycle with CH₃, C=O, N-phenyl, C=O) |
| N—CH₂-cyclopropyl | CH—CH₂-cyclopropyl |
| N (linked via CH₂ to cyclopropyl bearing NC) | CH₂ |
| N (linked via CH₂CH₂ to thiazolidine with NH and C(=O)OCH₃) | CH₂ |

* * * * *